(12) United States Patent
Haberman et al.

(10) Patent No.: US 12,187,142 B2
(45) Date of Patent: **\*Jan. 7, 2025**

(54) ENERGY SOURCE SUPPLY SYSTEMS, ENERGY SOURCE SUPPLY DEVICES, AND RELATED METHODS

(71) Applicant: A3 Labs LLC, Oakland, CA (US)

(72) Inventors: David Haberman, Delray Beach, FL (US); Elaine Mau, Berkeley, CA (US)

(73) Assignee: A3 LABS, LLC, Oakland, CA (US)

( * ) Notice: Subject to any disclaimer, the term of this patent is extended or adjusted under 35 U.S.C. 154(b) by 588 days.

This patent is subject to a terminal disclaimer.

(21) Appl. No.: 17/399,935

(22) Filed: Aug. 11, 2021

(65) Prior Publication Data

US 2021/0370784 A1  Dec. 2, 2021

Related U.S. Application Data

(63) Continuation of application No. 16/687,423, filed on Nov. 18, 2019, now Pat. No. 11,097,627, which is a
(Continued)

(51) Int. Cl.
*B60L 53/14* (2019.01)
*B23P 19/04* (2006.01)
(Continued)

(52) U.S. Cl.
CPC .............. *B60L 53/14* (2019.02); *B23P 19/04* (2013.01); *B60K 3/02* (2013.01);
(Continued)

(58) Field of Classification Search
CPC .... B60K 15/03006; B60K 2015/03019; B60K 2015/03026; B60K 3/02; B60L 53/14;
(Continued)

(56) References Cited

U.S. PATENT DOCUMENTS 4,931,947 A   6/1990   Werth et al.
5,409,046 A   4/1995   Swenson et al.
(Continued)

FOREIGN PATENT DOCUMENTS

CN   102347612 A   2/2012
CN   105375045 A   3/2016
(Continued)

OTHER PUBLICATIONS

International Search Report and Written Opinion for PCT/US2018/021341, dated Jun. 15, 2018. Jun. 15, 2018.

*Primary Examiner* — Victoria H Lynch
(74) *Attorney, Agent, or Firm* — BRYAN CAVE LEIGHTON PAISNER LLP

(57) ABSTRACT

Some embodiments include an appliance energy source supply system for an energy source supply appliance. The appliance energy source supply system can comprise a first thermal control device and a second thermal control device. The appliance energy source supply system can be configured so that a hydrogen fuel energy source is selectively received by one of the first thermal control device or the second thermal control device before the hydrogen fuel energy source is made available to a receiver vehicle. Other embodiments of related systems, devices, and methods also are provided.

26 Claims, 14 Drawing Sheets

Related U.S. Application Data continuation of application No. 15/882,632, filed on Jan. 29, 2018, now Pat. No. 10,478,929.

(60) Provisional application No. 62/468,520, filed on Mar. 8, 2017.

(51) Int. Cl.

| | |
|---|---|
| *B60K 3/02* | (2006.01) |
| *B60K 15/03* | (2006.01) |
| *B60L 53/35* | (2019.01) |
| *B60L 53/60* | (2019.01) |
| *B60L 53/66* | (2019.01) |
| *B60L 58/10* | (2019.01) |
| *B60L 58/30* | (2019.01) |
| *C07C 213/02* | (2006.01) |
| *C07C 231/10* | (2006.01) |
| *G05D 23/19* | (2006.01) |
| *H01M 8/04858* | (2016.01) |
| *H01M 8/10* | (2016.01) |
| *H01M 16/00* | (2006.01) |
| *H01M 8/04298* | (2016.01) |

(52) U.S. Cl.
CPC ........ *B60K 15/03006* (2013.01); *B60L 53/35* (2019.02); *B60L 53/60* (2019.02); *B60L 53/66* (2019.02); *B60L 58/10* (2019.02); *B60L 58/30* (2019.02); *C07C 213/02* (2013.01); *C07C 231/10* (2013.01); *G05D 23/1904* (2013.01); *H01M 8/04925* (2013.01); *H01M 8/10* (2013.01); *H01M 16/006* (2013.01); *B60K 2015/03019* (2013.01); *B60K 2015/03026* (2013.01); *C07B 2200/09* (2013.01); *F17C 2265/061* (2013.01); *H01M 8/04298* (2013.01); *H01M 2220/20* (2013.01); *H01M 2250/20* (2013.01); *Y02B 90/10* (2013.01); *Y02E 60/32* (2013.01); *Y02T 10/70* (2013.01); *Y02T 90/40* (2013.01)

(58) Field of Classification Search
CPC .......... B60L 53/35; B60L 53/60; B60L 53/66; B60L 58/10; B60L 58/30; C07C 213/02; C07C 231/10; H01M 16/006; H01M 2220/20; H01M 2250/20; H01M 8/04298; H01M 8/04925; H01M 8/10
See application file for complete search history.

(56) References Cited

U.S. PATENT DOCUMENTS

| | | |
|---|---|---|
| 6,198,245 B1 | 3/2001 | Du et al. |
| 6,619,336 B2 | 9/2003 | Cohen et al. |
| 6,745,105 B1 | 6/2004 | Fairlie et al. |
| 6,755,225 B1 | 6/2004 | Niedwiecki et al. |
| 6,810,925 B2 | 11/2004 | Graham et al. |
| 6,886,609 B2 | 5/2005 | Cohen et al. |
| 7,052,671 B2 | 5/2006 | McClaine et al. |
| 7,178,565 B2 | 2/2007 | Eichelberger et al. |
| 8,159,823 B2 | 4/2012 | Murakami |
| 8,291,944 B2 | 10/2012 | Allidieres |
| 8,492,047 B2 | 7/2013 | Hwang et al. |
| 8,557,461 B2 | 10/2013 | Kazuno et al. |
| 8,791,589 B2 | 7/2014 | Colello et al. |
| 8,963,481 B2 | 2/2015 | Prosser et al. |
| 9,132,742 B2 | 9/2015 | Dai et al. |
| 9,136,549 B2 | 9/2015 | Vollmer et al. |
| 9,261,238 B2 | 2/2016 | Cohen et al. |
| 9,863,583 B2 | 1/2018 | Youlio et al. |
| 10,059,215 B1 | 8/2018 | Haberman et al. |
| 2004/0005486 A1 | 1/2004 | Baker |
| 2004/0163731 A1 | 8/2004 | Eichelberger et al. |
| 2004/0182470 A1 | 9/2004 | White |
| 2004/0187950 A1 | 9/2004 | Cohen et al. |
| 2005/0007144 A1 | 1/2005 | Freeman et al. |
| 2006/0115693 A1 | 6/2006 | Toth et al. |
| 2006/0118201 A1 | 6/2006 | Li et al. |
| 2006/0174965 A1 | 8/2006 | Hobbs |
| 2006/0180240 A1 | 8/2006 | Niedzwiechi et al. |
| 2007/0062116 A1 | 3/2007 | Edlund et al. |
| 2007/0113921 A1 | 5/2007 | Capizzo |
| 2007/0274904 A1 | 11/2007 | Popham et al. |
| 2008/0138674 A1 | 6/2008 | Pez et al. |
| 2008/0185068 A1 | 8/2008 | Cohen et al. |
| 2008/0209916 A1 | 9/2008 | White |
| 2008/0222954 A1 | 9/2008 | Adams et al. |
| 2008/0302504 A1 | 12/2008 | Handa |
| 2009/0014546 A1 | 1/2009 | Yasuo |
| 2009/0068512 A1 | 3/2009 | Gofer et al. |
| 2009/0155642 A1 | 6/2009 | Popham |
| 2009/0164852 A1 | 6/2009 | Purrington et al. |
| 2009/0187416 A1 | 7/2009 | Baer et al. |
| 2009/0212626 A1 | 8/2009 | Snyder et al. |
| 2009/0290625 A1 | 11/2009 | Riddle et al. |
| 2009/0315330 A1 | 12/2009 | Dederick |
| 2010/0021353 A1 | 1/2010 | Edlund et al. |
| 2010/0248063 A1 | 9/2010 | Dwang et al. |
| 2010/0323279 A1 | 12/2010 | Fujiuchi et al. |
| 2011/0246013 A1 | 10/2011 | Yee et al. |
| 2012/0141891 A1 | 6/2012 | Kwon et al. |
| 2012/0271758 A1 | 10/2012 | Jammer |
| 2012/0316712 A1 | 12/2012 | Simonini et al. |
| 2013/0022888 A1 | 1/2013 | Vollmer et al. |
| 2013/0166241 A1 | 6/2013 | Hamann et al. |
| 2013/0257145 A1 | 10/2013 | Caldeira et al. |
| 2014/0007975 A1 | 1/2014 | Cohen et al. |
| 2014/0091564 A1 | 4/2014 | Brown |
| 2014/0311454 A1 | 10/2014 | Pursifull et al. |
| 2015/0155724 A1 | 6/2015 | Han et al. |
| 2015/0306974 A1 | 10/2015 | Mardall et al. |
| 2015/0378404 A1 | 12/2015 | Ogawa et al. |
| 2016/0091338 A1 | 3/2016 | Abuelsaad et al. |
| 2016/0129793 A1 | 5/2016 | Cronie |
| 2016/0207374 A1 | 7/2016 | Gauthier et al. |
| 2016/0207375 A1 | 7/2016 | Gauthier et al. |
| 2016/0207417 A1 | 7/2016 | Gauthier et al. |
| 2016/0225105 A1 | 8/2016 | Hill |
| 2016/0300170 A1 | 10/2016 | Sun et al. |
| 2016/0321740 A1 | 11/2016 | Hill |
| 2017/0096073 A1 | 4/2017 | Mardall et al. |
| 2017/0146194 A1 | 5/2017 | Youlio et al. |
| 2017/0254479 A1 | 9/2017 | Petersen et al. |
| 2017/0363432 A1 | 12/2017 | Hall et al. |
| 2019/0032849 A1 | 1/2019 | Seki et al. |
| 2019/0086031 A1 | 3/2019 | Fujisawa et al. |

FOREIGN PATENT DOCUMENTS

| | | |
|---|---|---|
| EP | 1555706 | 7/2005 |
| EP | 1517079 | 12/2007 |
| JP | 3470909 | 11/2003 |
| JP | 2008539683 A | 11/2008 |
| JP | 2012208686 | 10/2012 |
| KR | 20120139558 | 12/2012 |
| WO | 2010038069 | 4/2010 |
| WO | 2014186240 | 11/2014 |
| WO | 2016131132 | 10/2016 |
| WO | 2016180425 | 11/2016 |

ENERGY SOURCE SUPPLY SYSTEMS, ENERGY SOURCE SUPPLY DEVICES, AND RELATED METHODS

CROSS-REFERENCE TO RELATED APPLICATIONS

This application is a Continuation of U.S. patent application Ser. No. 16/687,423, filed on Nov. 18, 2019, which is a Continuation of U.S. patent application Ser. No. 15/882,632, filed on Jan. 29, 2018, which application claims the benefit of U.S. Provisional Application No. 62/468,520, filed Mar. 8, 2017. U.S. patent application Ser. No. 16/687,423, U.S. patent application Ser. No. 15/882,632, and U.S. Provisional Application No. 62/468,520 are incorporated herein by reference in their entirety.

FIELD OF THE INVENTION

This disclosure relates generally to energy source supply systems and energy source supply devices, and relates more particularly to mobile energy source supply devices configured to make available one or more energy sources to one or more vehicles, energy source supply systems implementing such mobile energy source supply devices, and related methods.

DESCRIPTION OF THE BACKGROUND

Due to an unavailability of an energy source in a particular region, it may not be possible in the region to operate a vehicle that uses the energy source for motive power. For example, unavailability in a region of hydrogen energy sources and/or electrical energy sources may prevent operation of hydrogen electric, plug-in electric, and/or hybrid electric vehicles in the region. Accordingly, a need or potential for benefit exists for systems, devices, and methods that can allow a vehicle to be operated in a region that lacks sufficient or any access to an energy source that the vehicle uses for motive power.

BRIEF DESCRIPTION OF THE DRAWINGS

To facilitate further description of the embodiments, the following drawings are provided in which.

Figure 1:
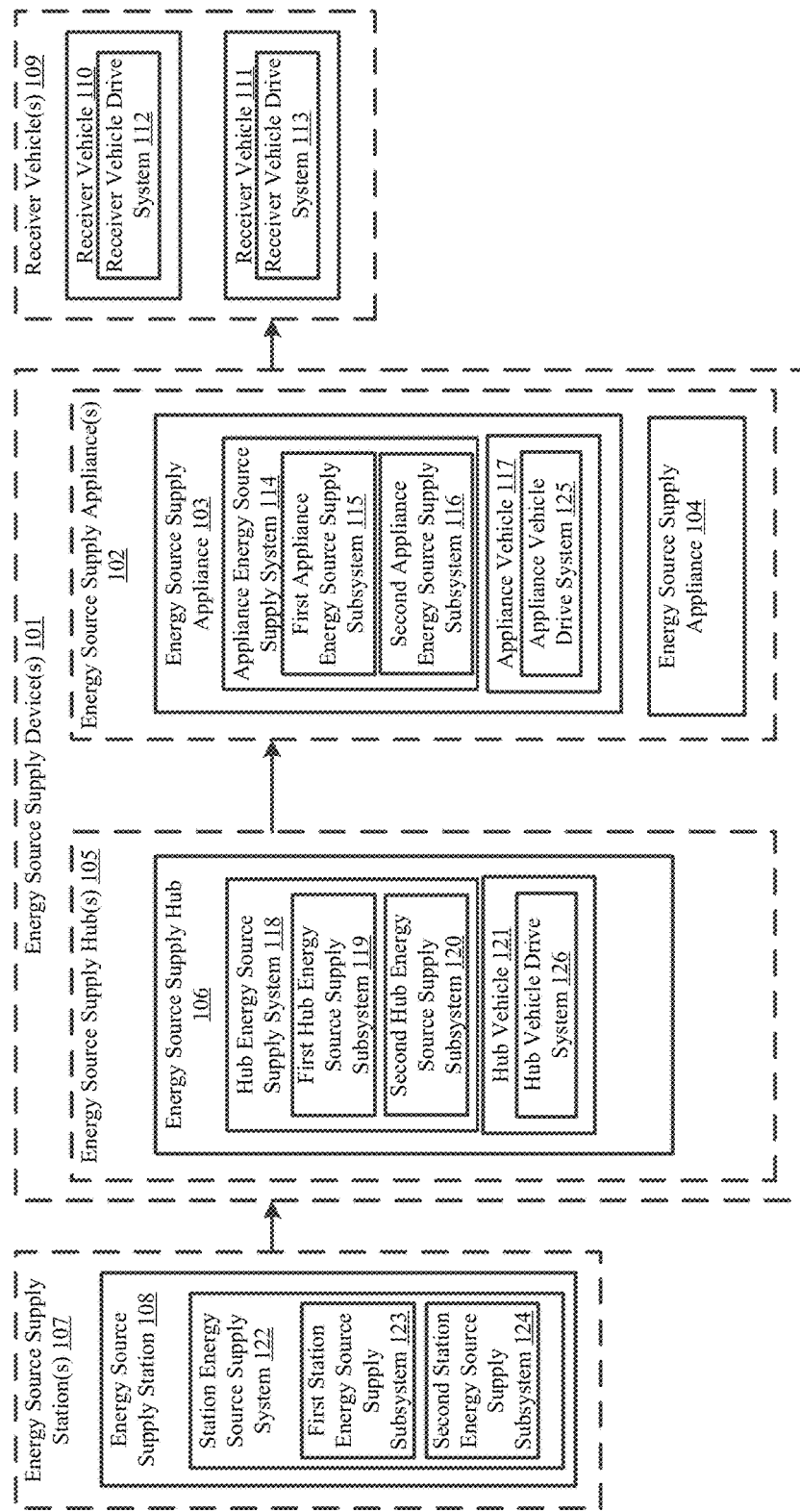
FIG. 1 illustrates an exemplary block diagram for a system, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled together, but not be mechanically or otherwise coupled together; two or more mechanical elements may be mechanically coupled together, but not be electrically or otherwise coupled together; two or more electrical elements may be mechanically coupled together, but not be electrically or otherwise coupled together. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

DETAILED DESCRIPTION OF EXAMPLES OF EMBODIMENTS

Some embodiments include a system. The system can comprise an energy source supply hub and an energy source supply appliance. The energy source supply hub can comprise a hub energy source supply system and a hub vehicle configured to transport the hub energy source supply system. Further, the hub energy source supply system can comprise a first hub energy source supply subsystem configured to receive a first energy source. Meanwhile, the energy source supply appliance can comprise an appliance energy source supply system and an appliance vehicle configured to transport the appliance energy source supply system. Further, the appliance energy source supply system can comprise a first appliance energy source supply subsystem configured to receive the first energy source from the first hub energy source supply subsystem and to make available the first energy source received from the first hub energy source supply subsystem to a receiver vehicle. Also, the receiver vehicle can comprise a drive system configured to use the first energy source received by the receiver vehicle to motively power the receiver vehicle.

Further embodiments include a method of providing a system. The method can comprise: providing an energy source supply hub; and providing an energy source supply appliance. Meanwhile, providing the energy source supply hub can comprise providing a hub energy source supply system, and the hub energy source supply system can be configured to be transported by a hub vehicle. Further, providing the hub energy source supply system can comprise providing a first hub energy source supply subsystem configured to receive a first energy source. Meanwhile, providing the energy source supply appliance can comprise providing an appliance energy source supply system, and the appliance energy source supply system can be configured to be transported by an appliance vehicle. Further, providing the appliance energy source supply system can comprise providing a first appliance energy source supply subsystem configured to receive the first energy source from the first hub energy source supply subsystem and to make available the first energy source received from the first hub energy source supply subsystem to a receiver vehicle. Also, the receiver vehicle can comprise a drive system configured to use the first energy source received by the receiver vehicle to motively power the receiver vehicle.

Further embodiments include a method. The method can comprise: moving an energy source supply appliance proximal to an energy source supply hub, the energy source supply hub comprising a hub energy source supply system that is configured to be transported by a hub vehicle, and the hub energy source supply system comprising a first hub energy source supply subsystem configured to make available a hydrogen fuel energy source; after moving the energy source supply appliance proximal to the energy source supply hub, receiving the hydrogen fuel energy source from the energy source supply hub at an appliance energy source supply subsystem of an appliance energy source supply system of the energy source supply appliance; after receiving the hydrogen fuel energy source at the appliance energy source supply subsystem, moving the energy source supply appliance proximal to a receiver vehicle; and after moving the energy source supply appliance proximal to the receiver vehicle, supplying the hydrogen fuel energy source from the appliance energy source supply subsystem to the receiver vehicle, the receiver vehicle comprising a drive system, and the drive system being configured to use the first energy source received by the receive vehicle to motively power the receiver vehicle.

Further embodiments include a system. The system can comprise an energy source supply hub and an energy source supply appliance. The energy source supply hub can comprise a hub energy source supply system and a hub vehicle configured to transport the hub energy source supply system. Further, the hub energy source supply system can comprise a first hub energy source supply subsystem configured to receive a first energy source. Meanwhile, the energy source supply appliance can comprise an appliance energy source supply system and an appliance vehicle configured to transport the appliance energy source supply system. Further, the appliance energy source supply system can comprise a first appliance energy source supply subsystem configured to receive the first energy source from the first hub energy source supply subsystem, and a second appliance energy source supply subsystem configured to receive the first energy source from the first appliance energy source supply subsystem, to convert the first energy source received from the first appliance energy source supply subsystem to a second energy source, and to make available the second energy source to a receiver vehicle. Also, the receiver vehicle can comprise a drive system configured to use the first energy source received by the receiver vehicle to motively power the receiver vehicle.

Some embodiments include an energy source supply appliance. The energy source supply appliance can comprise an appliance energy source supply system, which in turn can comprise a first appliance energy source supply subsystem and a second appliance energy source supply subsystem. The first appliance energy source supply subsystem can be configured to receive a first energy source. Meanwhile, the second appliance energy source supply subsystem can be configured to make available a second energy source to a first receiver vehicle, and the second energy source can be different from the first energy source. Further, the first receiver vehicle can comprise a first drive system, and the first drive system can be configured to use the second energy source received by the first receiver vehicle to motively power the first receiver vehicle.

Further embodiments include a method of providing an energy source supply appliance. The method can comprise providing an appliance energy source supply system. Meanwhile, providing the appliance energy source supply system can comprise: providing a first appliance energy source supply subsystem; and providing a second appliance energy source supply subsystem. The first appliance energy source supply subsystem can be configured to receive a first energy source. Meanwhile, the second appliance energy source supply subsystem can be configured to make available a second energy source to a first receiver vehicle, and the second energy source can be different from the first energy source. Further, the first receiver vehicle can comprise a first drive system, and the first drive system can be configured to use the second energy source received by the first receiver vehicle to motively power the first receiver vehicle.

Further embodiments include a method. The method can comprise: using a first appliance energy source supply subsystem of an appliance energy source supply system to make available a first energy source to a first receiver vehicle. The first receiver vehicle can comprise a first drive system configured to use the first energy source received by the first receiver vehicle to motively power the first receiver vehicle. The method also can comprise using a second appliance energy source supply subsystem of the appliance energy source supply system to make available a second energy source to a second receiver vehicle. The second receiver vehicle can comprise a second drive system configured to use the second energy source received by the second receiver vehicle to motively power the second receiver vehicle. The first energy source can comprise a hydrogen fuel energy source, and the second energy source can comprise an electrical energy source.

Some embodiments include an energy source supply appliance. The energy source supply appliance can comprise an appliance energy source supply system. The appliance energy source supply system can comprise a first thermal control device and a second thermal control device. The appliance energy source supply system can be configured to receive a hydrogen fuel energy source and to make available the hydrogen fuel energy source to a receiver vehicle, and the receiver vehicle can comprise a drive system configured to use the hydrogen fuel energy source received by the receiver vehicle to motively power the receiver vehicle. Meanwhile, the appliance energy source supply system can be configured so that the hydrogen fuel energy source is selectively received by one of the first thermal control device or the second thermal control device before the hydrogen fuel energy source is made available to the receiver vehicle, the first thermal control device can be configured to receive the hydrogen fuel energy source and to cause a first temperature reduction of the hydrogen fuel energy source when the first thermal control device receives the hydrogen fuel energy source, the second thermal control device can be configured to receive the hydrogen fuel energy source and to cause a second temperature reduction of the hydrogen fuel energy source when the second thermal control device receives the hydrogen fuel energy source, and the first temperature reduction is different than the second temperature reduction.

Some embodiments include an energy source supply appliance. The appliance energy source supply system can comprise an appliance energy source supply subsystem, and the appliance energy source supply subsystem can comprise a pressure regulator, a first thermal control device, and a second thermal control device. The appliance energy source supply subsystem can be configured to receive a hydrogen fuel energy source and to make available the hydrogen fuel energy source to a receiver vehicle, and the receiver vehicle can comprise a drive system configured to use the hydrogen fuel energy source received by the receiver vehicle to motively power the receiver vehicle. Meanwhile, the appliance energy source supply subsystem can be configured so that the hydrogen fuel energy source is received by the pressure regulator before the hydrogen fuel energy source is made available to the receiver vehicle, and the pressure regulator is configured to receive the hydrogen fuel energy source and to limit the hydrogen fuel energy source to a predetermined pressure when the pressure regulator receives the hydrogen fuel energy source. Further, the appliance energy source supply subsystem can be configured so that the hydrogen fuel energy source is selectively received by one of the first thermal control device or the second thermal control device before the hydrogen fuel energy source is made available to the receiver vehicle and after the hydrogen fuel energy source is received by the pressure regulator, the first thermal control device can be configured to receive the hydrogen fuel energy source and to cause a first temperature reduction of the hydrogen fuel energy source when the first thermal control device receives the hydrogen fuel energy source, the second thermal control device can be configured to receive the hydrogen fuel energy source and to cause a second temperature reduction of the hydrogen fuel energy source when the second thermal control device receives the hydrogen fuel energy source, and the first temperature reduction is different than the second temperature reduction.

Some embodiments include an appliance energy source supply system for an energy source supply appliance. The appliance energy source supply system can comprise a first thermal control device and a second thermal control device. The appliance energy source supply system can be configured so that a hydrogen fuel energy source is selectively received by one of the first thermal control device or the second thermal control device before the hydrogen fuel energy source is made available to a receiver vehicle. The first thermal control device can be configured to receive the hydrogen fuel energy source and to cause a first temperature reduction of the hydrogen fuel energy source when the first thermal control device receives the hydrogen fuel energy source. The second thermal control device can be configured to receive the hydrogen fuel energy source and to cause a second temperature reduction of the hydrogen fuel energy source when the second thermal control device receives the hydrogen fuel energy source. The first temperature reduction can be different than the second temperature reduction.

Further embodiments include a method of manufacturing an energy source supply appliance. The method can comprise providing an appliance energy source supply system. Meanwhile, providing the appliance energy source supply system can comprise providing an appliance energy source supply subsystem, and providing the appliance energy source supply subsystem can comprise: providing a pressure regulator; providing a first thermal control device; and providing a second thermal control device. The appliance energy source supply subsystem can be configured to receive a hydrogen fuel energy source and to make available the hydrogen fuel energy source to a receiver vehicle, and the receiver vehicle can comprise a drive system configured to use the hydrogen fuel energy source received by the receiver vehicle to motively power the receiver vehicle. Meanwhile, the appliance energy source supply subsystem can be configured so that the hydrogen fuel energy source is received by the pressure regulator before the hydrogen fuel energy source is made available to the receiver vehicle, and the pressure regulator is configured to receive the hydrogen fuel energy source and to limit the hydrogen fuel energy source to a predetermined pressure when the pressure regulator receives the hydrogen fuel energy source. Further, the appliance energy source supply subsystem can be configured so that the hydrogen fuel energy source is selectively received by one of the first thermal control device or the second thermal control device before the hydrogen fuel energy source is made available to the receiver vehicle and after the hydrogen fuel energy source is received by the pressure regulator, the first thermal control device can be configured to receive the hydrogen fuel energy source and to cause a first temperature reduction of the hydrogen fuel energy source when the first thermal control device receives the hydrogen fuel energy source, the second thermal control device can be configured to receive the hydrogen fuel energy source and to cause a second temperature reduction of the hydrogen fuel energy source when the second thermal control device receives the hydrogen fuel energy source, and the first temperature reduction is different than the second temperature reduction.

Some embodiments include a method. The method can comprise providing an appliance energy source supply system. Providing the appliance energy source supply system can include: providing a first thermal control device, and providing a second thermal control device. The appliance energy source supply system can be configured so that a hydrogen fuel energy source is selectively received by one of the first thermal control device or the second thermal control device before the hydrogen fuel energy source is made available to a receiver vehicle. Meanwhile, the first thermal control device can be configured to receive the hydrogen fuel energy source and to cause a first temperature reduction of the hydrogen fuel energy source when the first thermal control device receives the hydrogen fuel energy source. The second thermal control device can be configured to receive the hydrogen fuel energy source and to cause a second temperature reduction of the hydrogen fuel energy source when the second thermal control device receives the hydrogen fuel energy source. The first temperature reduction can be different than the second temperature reduction.

Further embodiments include a method. The method can comprise: receiving a hydrogen fuel energy source at an appliance energy source supply subsystem, wherein the appliance energy source supply subsystem comprises a first thermal control device and a second thermal control device; after receiving the hydrogen fuel energy source at the appliance energy source supply subsystem, limiting the hydrogen fuel energy source to a predetermined pressure; selecting one of the first thermal control device or the second thermal control device to receive the hydrogen fuel energy source, wherein the first thermal control device is configured to receive the hydrogen fuel energy source and to cause a first temperature reduction of the hydrogen fuel energy source when the first thermal control device receives the hydrogen fuel energy source, the second thermal control device is configured to receive the hydrogen fuel energy source and to cause a second temperature reduction of the hydrogen fuel energy source when the second thermal control device receives the hydrogen fuel energy source, and the first temperature reduction is different than the second temperature reduction; and after limiting the hydrogen fuel energy source to the predetermine pressure, and after selecting the one of the first thermal control device or the second thermal control device, making available the hydrogen fuel energy source to a receiver vehicle, wherein the receiver vehicle comprises a drive system configured to use the hydrogen fuel energy source received by the receiver vehicle to motively power the receiver vehicle, and making available the hydrogen fuel energy source to the receiver vehicle comprises receiving the hydrogen fuel energy source at the one of the first thermal control device or the second thermal control device.

A number of embodiments can include another method. The method can comprise receiving a hydrogen fuel energy source at an appliance energy source supply system. The appliance energy source supply system can comprise a first thermal control device and a second thermal control device. The method further can include selecting one of the first thermal control device or the second thermal control device to receive the hydrogen fuel energy source. The first thermal control device can be configured to receive the hydrogen fuel energy source and to cause a first temperature reduction of the hydrogen fuel energy source when the first thermal control device receives the hydrogen fuel energy source. The second thermal control device can be configured to receive the hydrogen fuel energy source and to cause a second temperature reduction of the hydrogen fuel energy source when the second thermal control device receives the hydrogen fuel energy source. The first temperature reduction can be different than the second temperature reduction. In addition, the method can, after selecting the one of the first thermal control device or the second thermal control device, include making available the hydrogen fuel energy source to a receiver vehicle. Making available the hydrogen fuel energy source to the receiver vehicle can comprise receiving the hydrogen fuel energy source at the one of the first thermal control device or the second thermal control device, as selected, before receiving the hydrogen fuel energy source at the receiver vehicle.

Turning to the drawings, FIG. 1 illustrates an exemplary block diagram for system 100, according to an embodiment. System 100 is merely exemplary and is not limited to the embodiments presented herein. System 100 can be employed in many different embodiments or examples not specifically depicted or described herein.

As described in greater detail below, in many embodiments, system 100 can be configured to make available one or more energy sources to one or more vehicles (e.g., receiver vehicle(s) 109), and in some embodiments, system 100 can be configured to make available multiple different energy sources to the vehicle(s). In these or other embodiments, system 100 can include one or more energy source supply devices (e.g., energy source supply device(s) 101) that are configured to make available the energy source(s) to the vehicle(s). Accordingly, in many embodiments, system 100 and the energy storage supply device(s) of system 100 can permit one or more vehicles to be operated in one or more regions that lack sufficient or any access to one or more energy sources that the vehicle(s) make use of to provide motive power to the vehicle(s), and in further embodiments, can optimally make available the energy source(s) to the vehicle(s).

In many embodiments, system 100 comprises one or more energy source supply devices 101. Energy source supply device(s) 101 can comprise one or more energy source supply appliances 102 (e.g., energy source supply appliance 103 and/or energy source supply appliance 104) and/or one or more energy source supply hubs 105 (e.g., energy source supply hub 106). Further, system 100 can comprise one or more energy source supply stations 107 (e.g., energy source supply station 108) and/or one or more receiver vehicles 109 (e.g., receiver vehicle 110 and/or receiver vehicle 111). In some embodiments, one or more of energy source supply hub(s) 105 (e.g., energy source supply hub 106), one or more of energy source supply station(s) 107 (e.g., energy source supply station 108), and/or one or more of receiver vehicle(s) 109 (e.g., receiver vehicle 110 and/or receiver vehicle 111) can be omitted.

In many embodiments, each of receiver vehicle(s) 109 (e.g., receiver vehicle 110 and/or receiver vehicle 111) are configured to receive an energy source, and each comprise a receiver vehicle drive system (e.g., receiver vehicle drive system 112 and/or receiver vehicle drive system 113) configured to motively power that receiver vehicle of receiver vehicle(s) 109 by using the energy source received by the receiver vehicle. For example, the term "motively power" can mean to cause to move or to change position, to cause locomotion, or to propel. Accordingly, in many embodiments, the receiver vehicle drive system of a receiver vehicle of receiver vehicle(s) 109 can refer to a propulsion system of the receiver vehicle. Further, in many embodiments, a receiver vehicle of receiver vehicle(s) 109 can use the energy source received by the receiver vehicle to motively power the receiver vehicle by converting the energy source that is received into mechanical energy and using the mechanical energy to do work that moves the receiver vehicle.

In some embodiments, when receiver vehicle(s) 109 comprise multiple receiver vehicles, the energy sources received by the multiple receiver vehicles can be the same for two or more receiver vehicles of the multiple receiver vehicles and/or different for two or more receiver vehicles of the multiple receiver vehicles. Accordingly, two or more receiver vehicles of receiver vehicle(s) 109 and their respective receiver vehicle drive systems can be similar or identical to each other, such as, for example, when the energy sources received by the two or more receiver vehicles are the same; and/or two or more receiver vehicles of receiver vehicle(s) 109 and their receiver vehicle drive systems can be different than each other, such as, for example, when the energy sources received by the two or more receiver vehicles are different.

In many embodiments, receiver vehicle(s) 109 can be any type or types of vehicles. Exemplary type(s) of vehicles can comprise a car, a truck, a motorcycle, a bicycle, a scooter, a boat, a train, an aircraft, a space craft, an airport ground support equipment, a material handling equipment (e.g., a fork-lift), etc. In some embodiments, two or more receiver vehicles of receiver vehicle(s) 109 can be the same type of vehicle as each other; and/or two or more receiver vehicles of receiver vehicle(s) 109 can be different types of vehicles than each other.

In many embodiments, receiver vehicle(s) 109 can comprise receiver vehicle 110 and/or receiver vehicle 111. Further, receiver vehicle 110 can comprise receiver vehicle drive system 112, and receiver vehicle 111 can comprise receiver vehicle drive system 113.

Receiver vehicle 110 is configured to receive a first energy source, and receiver vehicle drive system 112 is configured to motively power receiver vehicle 110 by using the first energy source received by receiver vehicle 110. For example, in some embodiments, the first energy source can comprise a fuel energy source. Accordingly, in these or other embodiments, receiver vehicle 110 can comprise a hydrogen fuel or hydrogen electric vehicle. In other embodiments, receiver vehicle 110 can comprise a natural gas vehicle.

In some embodiments, when the first energy source comprises a fuel energy source, receiver vehicle drive system 112 can comprise an internal combustion engine configured to motively power receiver vehicle 110 by combusting the fuel energy source. In these embodiments, the fuel energy source can comprise any fuel energy source suitably configured to be combusted by an internal combustion engine to motively power receiver vehicle 110. For example, when receiver vehicle drive system 112 comprises an internal combustion engine configured to motively power receiver vehicle 110 by combusting a fuel energy source, the fuel energy source can comprise a petroleum-based fuel (e.g., gasoline, petroleum diesel, autogas, natural gas (e.g., compressed or liquefied natural gas), aviation fuel, fuel oil, etc.), a coal-based fuel (e.g., gasoline, petroleum diesel, etc.), a vegetable oil, wood gas, a biofuel (e.g., biobutanol, biodiesel, dimethyl ether, bioethanol, biomethanol, biogas, etc.), hydrogen, or the like.

In other embodiments, when the first energy source comprises a fuel energy source, receiver vehicle drive system 112 can comprise one or more fuel cells and one or more electric motors electrically coupled to the one or more fuel cells. Further, the fuel cell(s) of receiver vehicle drive system 112 can convert the fuel energy source into electricity and can make available the electricity to the electric motor(s) of receiver vehicle drive system 112 to motively power receiver vehicle 110. In these embodiments, the fuel energy source can comprise any fuel energy source suitably configured to be converted into electricity by the fuel cell(s) of receiver vehicle drive system 112. For example, when receiver vehicle drive system 112 comprises one or more fuel cells configured to convert the fuel energy source into electricity and to make available the electricity to the electric motor(s) of receiver vehicle drive system 112 to motively power receiver vehicle 110, the fuel energy source can comprise hydrogen, methanol, natural gas (e.g., compressed or liquefied natural gas), methane, propane, butane, hexane, octane, salt water, or the like.

Meanwhile, receiver vehicle 111 is configured to receive a second energy source, and receiver vehicle drive system 113 is configured to motively power receiver vehicle 111 by using the second energy source received by receiver vehicle 111. In many embodiments, the second energy source that receiver vehicle 111 is configured to receive can be different than the first energy source that receiver vehicle 110 is configured to receive. For example, in some embodiments, the second energy source can comprise an electrical energy source (i.e., electricity). Accordingly, in these or other embodiments, receiver vehicle 111 can comprise a full electric or hybrid electric vehicle.

In some embodiments, when the second energy source comprises an electrical energy source, receiver vehicle drive system 113 can comprise one or more rechargeable energy storage systems and one or more electric motors electrically coupled to the rechargeable energy storage system(s). For example, in these embodiments, the rechargeable energy storage system(s) of receiver vehicle drive system 113 can store the electrical energy source and can make available the electrical energy source to the electric motor(s) of receiver vehicle drive system 113 to motively power receiver vehicle 110. Further, in these embodiments, the rechargeable energy storage system(s) can comprise (a) one or more electrochemical cells (e.g., one or more batteries), (b) one or more capacitive energy storage systems (e.g., super capacitors such as electric double-layer capacitors), and/or (c) one or more inertial energy storage systems (e.g., one or more flywheels).

In many embodiments, energy source supply appliance(s) 102 comprise energy source supply appliance 103. Further, when energy source supply appliance(s) 102 comprise multiple energy source supply appliances, energy source supply appliance(s) 102 also can comprise energy source supply appliance 104. In some embodiments, when energy source supply appliance(s) 102 comprise multiple energy source supply appliances, one or more energy source supply appliances of the multiple energy source supply appliances can be similar or identical to one or more other energy source supply appliances of the multiple energy source supply appliances. In these or other embodiments, one or more energy source supply appliances of the multiple energy source supply appliances can be different than one or more other energy source supply appliances of the multiple energy source supply appliances. For example, in some embodiments, energy source supply appliance 104 and/or one or more other energy source supply appliances of energy source supply appliance(s) 102 can be similar or identical to energy source supply appliance 103.

Energy source supply appliance(s) 102 (e.g., energy source supply appliance 103 and/or energy source supply appliance 104) each can be configured to make available one or more energy sources to receiver vehicle(s) 109 (e.g., receiver vehicle 110 and/or receiver vehicle 111). In many embodiments, at least one energy source supply appliance of energy source supply appliance(s) 102 (e.g., energy source supply appliance 103 and/or energy source supply appliance 104) can be configured to make available multiple different energy sources to receiver vehicle(s) 109, such as, for example, when receiver vehicle(s) 109 comprise two or more receiver vehicles configured to receive different energy sources. As defined herein, a "unary energy source supply appliance" can refer to an energy source supply appliance of energy source supply appliance(s) 102 that is configured to make available one energy source to receiver vehicle(s) 109, and a "binary energy source supply appliance" can refer to an energy source supply appliance of energy source supply appliance(s) 102 that is configured to make available two different energy sources to receiver vehicle(s) 109.

In many embodiments, energy source supply appliance 103 comprises an appliance energy source supply system 114. Appliance energy source supply system 114 comprises first appliance energy source supply subsystem 115. In some embodiments, appliance energy source supply system 114 also can comprise second appliance energy source supply subsystem 116. In further embodiments, part or all of second appliance energy source supply subsystem 116 can be part of first appliance energy source supply subsystem 115, and vice versa. In other embodiments, second appliance energy source supply subsystem 116 can be omitted.

In many embodiments, energy source supply appliance 103 can be mobile. For example, in some embodiments, energy source supply appliance 103 can comprise appliance vehicle 117, and appliance energy source supply system 114 can be transportable by appliance vehicle 117. In many embodiments, appliance vehicle 117 can be any type of vehicle suitable to transport appliance energy source supply system 114, such as, for example, a car, a truck, a boat, a train, an aircraft, a space craft, etc. In some embodiments, energy source supply system 114 can be separated from appliance vehicle 117, such as when energy source supply system 114 is on a trailer that is pulled by appliance vehicle 117. In other embodiments, energy source supply system 114 is integrated with and is not separable from appliance vehicle 117. Additional details of appliance vehicle 117 are described below.

In some embodiments, first appliance energy source supply subsystem 115 can make available the first energy source to one or more receiver vehicles of receiver vehicle(s) 109 (e.g., receiver vehicle 110) that are configured to receive the first energy source. In these or other embodiments, first appliance energy source supply subsystem 115 can make available the first energy source to second appliance energy source supply subsystem 116, such as, for example, so that second appliance energy source supply subsystem 116 can convert (e.g., electrochemically convert) the first energy source to the second energy source as described in greater detail below. In other embodiments, first appliance energy source supply subsystem 115 can make available the first energy source to second appliance energy source supply subsystem 116 but not to receiver vehicle(s) 109.

In many embodiments, first appliance energy source supply subsystem 115 can be configured to receive the first energy source so that first appliance energy source supply subsystem 115 can make available the first energy source to (i) the one or more receiver vehicles of receiver vehicle(s) 109 (e.g., receiver vehicle 110) that are configured to receive the first energy source and/or (ii) second appliance energy source supply subsystem 116. For example, in some embodiments, first appliance energy source supply subsystem 115 can be configured to receive the first energy source from energy source supply hub(s) 105 (e.g., energy source supply hub 106) and/or energy source supply station(s) 107 (e.g., energy source supply station 108), as further described below.

In these or other embodiments, first appliance energy source supply subsystem 115 can be configured to produce (e.g., generate) the first energy source at first appliance energy source supply subsystem 115 so that first appliance energy source supply subsystem 115 can make available the first energy source to (i) the one or more receiver vehicles of receiver vehicle(s) 109 (e.g., receiver vehicle 110) that are configured to receive the first energy source and/or (ii) second appliance energy source supply subsystem 116. In some embodiments, such as, for example, when the first energy source comprises a hydrogen fuel energy source, first appliance energy source supply subsystem 115 can be configured to produce (e.g., generate) the first energy source at first appliance energy source supply subsystem 115 from water, such as, for example, using electrolysis. In these embodiments, first appliance energy source supply subsystem 115 can be configured to receive water in order to produce the hydrogen fuel energy source at first appliance energy source supply subsystem 115. In other embodiments, such as, for example, when the first energy source comprises an electrical energy source (i.e., electricity), first appliance energy source supply subsystem 115 can be configured to produce (e.g., generate) the first energy source at first appliance energy source supply subsystem 115 from a power plant, such as, for example, a solar energy power plant or a wind energy power plant. In these embodiments, first appliance energy source supply subsystem 115 can comprise the power plant. In still other embodiments, first appliance energy source supply subsystem 115 can be configured to receive but not to produce (e.g., generate) the first energy source made available by first appliance energy source supply subsystem 115 to (i) the one or more receiver vehicles of receiver vehicle(s) 109 (e.g., receiver vehicle 110) that are configured to receive the first energy source and/or (ii) second appliance energy source supply subsystem 116.

In many embodiments, first appliance energy source supply subsystem 115 can be configured to store the first energy source so that first appliance energy source supply subsystem 115 can make available the first energy source to (i) the one or more receiver vehicles of receiver vehicle(s) 109 that are configured to receive the first energy source (e.g., receiver vehicle 110) and/or (ii) second appliance energy source supply subsystem 116. In some embodiments, first appliance energy source supply subsystem 115 can comprise an appliance first energy source storage capacity. In these or other embodiments, when the first energy source comprises a fuel energy source, first appliance energy source supply subsystem 115 can be configured to store the first energy source under a pressure greater than atmospheric pressure so that first appliance energy source supply subsystem 115 can store more of the first energy source in a smaller space.

Further, second appliance energy source supply subsystem 116 can make available the second energy source to one or more receiver vehicles of receiver vehicle(s) 109 (e.g., receiver vehicle 111) that are configured to receive the second energy source. In some embodiments, second appliance energy source supply subsystem 116 can be configured to receive the second energy source so that second appliance energy source supply subsystem 116 can make available the second energy source to the one or more receiver vehicles of receiver vehicle(s) 109 that are configured to receive the second energy source (e.g., receiver vehicle 111). In these or other embodiments, second appliance energy source supply subsystem 116 can be configured to convert (e.g., electrochemically convert) the first energy source to the second energy source so that second appliance energy source supply subsystem 116 can make available the second energy source to the one or more receiver vehicles of receiver vehicle(s) 109 (e.g., receiver vehicle 111) that are configured to receive the second energy source. For example, in some embodiments, the first energy source can comprise a hydrogen fuel energy source or a natural gas fuel energy source, the second energy source can comprise an electrical energy source (i.e., electricity), and second appliance energy source supply subsystem 116 can convert (e.g., electrochemically convert) the hydrogen fuel energy source or natural gas energy fuel energy source to the electrical energy source, such as, for example, using one or more fuel cells. In other embodiments, the first energy source can comprise an electrical energy source (i.e., electricity), the second energy source can comprise a hydrogen fuel energy source or a natural gas energy fuel energy source, and second appliance energy source supply subsystem 116 can convert (e.g., electrochemically convert) the electrical energy source to the hydrogen fuel energy source or natural gas energy fuel energy source, such as, for example, using electrolysis or other electrochemical conversion.

In many embodiments, second appliance energy source supply subsystem 116 can be configured to receive the second energy source so that second appliance energy source supply subsystem 116 can make available the second energy source to the one or more receiver vehicles of receiver vehicle(s) 109 (e.g., receiver vehicle 111) that are configured to receive the second energy source. For example, in some embodiments, second appliance energy source supply subsystem 116 can be configured to receive the first energy source from first appliance energy source supply subsystem 115, energy source supply hub(s) 105 (e.g., energy source supply hub 106), and/or energy source supply station(s) 107 (e.g., energy source supply station 108), as further described below. In further embodiments, second appliance energy source supply subsystem 116 can be configured to receive the second energy source from energy source supply hub(s) 105 (e.g., energy source supply hub 106) and/or energy source supply station(s) 107 (e.g., energy source supply station 108), as further described below.

In these or other embodiments, second appliance energy source supply subsystem 116 can be configured to produce (e.g., generate) the second energy source at second appliance energy source supply subsystem 116 so that second appliance energy source supply subsystem 116 can make available the second energy source to (i) the one or more receiver vehicles of receiver vehicle(s) 109 (e.g., receiver vehicle 111) that are configured to receive the second energy source. In some embodiments, such as, for example, when the second energy source comprises a hydrogen fuel energy source, second appliance energy source supply subsystem 116 can be configured to produce (e.g., generate) the second energy source at second appliance energy source supply subsystem 116 from water, such as, for example, using electrolysis. In these embodiments, second appliance energy source supply subsystem 116 can be configured to receive water in order to produce the hydrogen fuel energy source at second appliance energy source supply subsystem 116. In other embodiments, such as, for example, when the second energy source comprises an electrical energy source (i.e., electricity), second appliance energy source supply subsystem 116 can be configured to produce (e.g., generate) the second energy source at second appliance energy source supply subsystem 116 from a power plant, such as, for example, a solar energy power plant or a wind energy power plant. In these embodiments, second appliance energy source supply subsystem 116 can comprise the power plant. In still other embodiments, second appliance energy source supply subsystem 116 can be configured to receive but not to produce (e.g., generate) the second energy source made available by second appliance energy source supply subsystem 116 to the one or more receiver vehicles of receiver vehicle(s) 109 (e.g., receiver vehicle 111) that are configured to receive the second energy source.

In many embodiments, second appliance energy source supply subsystem 116 can be configured to store the second energy source so that second appliance energy source supply subsystem 116 can make available the second energy source to the one or more receiver vehicles of receiver vehicle(s) 109 (e.g., receiver vehicle 111) that are configured to receive the second energy source. In some embodiments, second appliance energy source supply subsystem 116 can comprise an appliance second energy source storage capacity. In these or other embodiments, when the second energy source comprises a fuel energy source, second appliance energy source supply subsystem 116 can be configured to store the second energy source under a pressure greater than atmospheric pressure so that second appliance energy source supply subsystem 116 can store more of the second energy source. As a specific example of an embodiment of first appliance energy source supply subsystem 115 and second appliance energy source supply subsystem 116, the first energy source delivered by first appliance energy source supply subsystem 115 to receiver vehicle 110 can be hydrogen or natural gas, and the second energy source deliver by second appliance energy source supply subsystem 116 to receiver vehicle 111 can be electricity.

Returning to other parts of appliance energy source supply appliance 103, appliance vehicle 117 can comprise appliance vehicle drive system 125, and appliance vehicle drive system 125 can be configured to motively power appliance vehicle 117. In some embodiments, appliance vehicle drive system 125 can be configured to receive at least one energy source of the one or more energy sources made available to receiver vehicle(s) 109 (e.g., receiver vehicle 110 and/or receiver vehicle 111) by energy source supply appliance 103 to motively power appliance vehicle 117. In other embodiments, appliance vehicle drive system 125 can use another energy source to motively power appliance vehicle 117.

In many embodiments, energy source supply hub(s) 105 can comprise energy source supply hub 106. In some embodiments, when energy source supply hub(s) 105 comprise multiple energy source supply hubs, one or more energy source supply hubs of the multiple energy source supply hubs can be similar or identical to one or more other energy source supply hubs of the multiple energy source supply hubs. In these or other embodiments, when energy source supply hub(s) 105 comprise multiple energy source supply hubs, one or more energy source supply hubs of the multiple energy source supply hubs can be different than one or more other energy source supply hubs of the multiple energy source supply hubs. In other embodiments, one or more other energy source supply hubs of energy source supply hub(s) 105 can be similar or identical to energy source supply hub 106.

Energy source supply hub(s) 105 (e.g., energy source supply hub 106) each can be configured to make available one or more energy sources to (i) one or more energy source supply appliances of energy source supply appliance(s) 102 (e.g., energy source supply appliance 103 and/or energy source supply appliance 104) and/or (ii) one or more receiver vehicles of receiver vehicle(s) 109 (e.g., receiver vehicle 110 and/or receiver vehicle 111). In some embodiments, at least one energy source supply hub of energy source supply hub(s) 105 (e.g., energy source supply hub 106) can be configured (i) to make available multiple different energy sources to energy source supply appliance(s) 102, such as, for example, when energy source supply appliance(s) 102 comprise one or more binary energy source supply appliances and/or two or more unary energy source supply appliances configured to make available different energy sources to receiver vehicle(s) 109, and/or (ii) to make available multiple different energy sources to receiver vehicle(s) 109. As defined herein, a "unary energy source supply hub" can refer to an energy source supply hub of energy source supply hub(s) 105 that is configured to make available one energy source to energy source supply appliance(s) 102 and/or receiver vehicle(s) 109, and a "binary energy source supply hub" can refer to an energy source supply hub of energy source supply hub(s) 105 that is configured to make available two different energy sources to energy source supply appliance(s) 102 and/or receiver vehicle(s) 109.

In many embodiments, energy source supply hub 106 comprises hub energy source supply system 118. Hub energy source supply system 118 comprises first hub energy source supply subsystem 119. In some embodiments, hub energy source supply system 118 also can comprise second hub energy source supply subsystem 120. In other embodiments, second hub energy source supply subsystem 120 can be omitted.

In many embodiments, energy source supply hub 106 can be mobile. For example, in some embodiments, energy source supply hub 106 can comprise a hub vehicle 121, and hub energy source supply system 118 can be transportable by hub vehicle 121. In many embodiments, hub vehicle 121 can be any type of vehicle suitable to transport hub energy source supply system 118, such as, for example, a car, a truck, a boat, a train, an aircraft, a space craft, etc. In some embodiments, energy source supply hub 106 can be larger than energy source supply appliance 103. In some embodiments, energy source supply hub 106 can be separated from hub vehicle 121, such as when energy source supply hub 106 is on a trailer that is pulled by hub vehicle 121. In other embodiments, energy source supply hub 106 is integrated with and is not separable from hub vehicle 106. Additional details of hub vehicle 126 are described below.

In some embodiments, first hub energy source supply subsystem 119 can make available the first energy source to (i) one or more energy source supply appliances of energy source supply appliance(s) 102 (e.g., energy source supply appliance 103 and/or energy source supply appliance 104) and/or (ii) one or more receiver vehicles of receiver vehicle(s) 109 that are configured to receive the first energy source (e.g., receiver vehicle 110). In these or other embodiments, first hub energy source supply subsystem 119 can make available the first energy source to second hub energy source supply subsystem 120, such as, for example, so that second hub energy source supply subsystem 120 can convert (e.g., electrochemically convert) the first energy source to the second energy source as described in greater detail below. In other embodiments, first hub energy source supply subsystem 119 can make available the first energy source to second hub energy source supply subsystem 120 but not (i) energy source supply appliance(s) 102 and/or (ii) receiver vehicle(s) 109.

In many embodiments, first hub energy source supply subsystem 119 can be configured to receive the first energy source so that first hub energy source supply subsystem 119 can make available the first energy source to (i) the one or more energy source supply appliances of energy source supply appliance(s) 102 (e.g., energy source supply appliance 103 and/or energy source supply appliance 104), (ii) the one or more receiver vehicles of receiver vehicle(s) 109 that are configured to receive the first energy source (e.g., receiver vehicle 110), and/or (iii) second hub energy source supply subsystem 120. For example, in some embodiments, first hub energy source supply subsystem 119 can be configured to receive the first energy source from energy source supply station(s) 107 (e.g., energy source supply station 108), as further described below.

In these or other embodiments, first hub energy source supply subsystem 119 can be configured to produce (e.g., generate) the first energy source at first hub energy source supply subsystem 119 so that first hub energy source supply subsystem 119 can make available the first energy source to (i) the one or more energy source supply appliances of energy source supply appliance(s) 102 (e.g., energy source supply appliance 103 and/or energy source supply appliance 104), (ii) the one or more receiver vehicles of receiver vehicle(s) 109 that are configured to receive the first energy source (e.g., receiver vehicle 110), and/or (iii) second hub energy source supply subsystem 120. In some embodiments, such as, for example, when the first energy source comprises a hydrogen fuel energy source, first hub energy source supply subsystem 119 can be configured to produce (e.g., generate) the first energy source at first hub energy source supply subsystem 119 from water, such as, for example, using electrolysis. In these embodiments, first hub energy source supply subsystem 119 can be configured to receive water in order to produce the hydrogen fuel energy source at first hub energy source supply subsystem 119. In other embodiments, such as, for example, when the first energy source comprises an electrical energy source (i.e., electricity), first hub energy source supply subsystem 119 can be configured to produce (e.g., generate) the first energy source at first hub energy source supply subsystem 119 from a power plant, such as, for example, a solar energy power plant or a wind energy power plant. In these embodiments, first hub energy source supply subsystem 119 can comprise the power plant. In still other embodiments, first hub energy source supply subsystem 119 can be configured to receive but not to produce (e.g., generate) the first energy source made available by first hub energy source supply subsystem 119 to (i) the one or more energy source supply appliances of energy source supply appliance(s) 102 (e.g., energy source supply appliance 103 and/or energy source supply appliance 104), (ii) the one or more receiver vehicles of receiver vehicle(s) 109 that are configured to receive the first energy source (e.g., receiver vehicle 110), and/or (iii) second hub energy source supply subsystem 120.

In many embodiments, first hub energy source supply subsystem 119 can be configured to store the first energy source so that first hub energy source supply subsystem 119 can make available the first energy source to (i) the one or more energy source supply appliances of energy source supply appliance(s) 102 (e.g., energy source supply appliance 103 and/or energy source supply appliance 104), (ii) the one or more receiver vehicles of receiver vehicle(s) 109 that are configured to receive the first energy source (e.g., receiver vehicle 110), and/or (iii) second hub energy source supply subsystem 120. In many embodiments, first hub energy source supply subsystem 119 can comprise a hub first energy source storage capacity. In further embodiments, the hub first energy source storage capacity can be greater than the appliance first energy source storage capacity described above with respect to energy source supply appliance 103 and first appliance energy source supply subsystem 115. For example, in some embodiments, the hub first energy source storage capacity can be approximately 6, 7, 8, 9, or 10 times greater than the appliance first energy source storage capacity. In these or other embodiments, when the first energy source comprises a fuel energy source, first hub energy source supply subsystem 119 can be configured to store the first energy source under pressure so that first hub energy source supply subsystem 119 can store more of the first energy source. In further embodiments, first hub energy source supply subsystem 119 can be configured to store the first energy source under a pressure greater than the pressure at which first appliance energy source supply subsystem 115 stores the first energy source.

Further, in some embodiments, second hub energy source supply subsystem 120 can make available the second energy source to (i) one or more energy source supply appliances of energy source supply appliance(s) 102 (e.g., energy source supply appliance 103 and/or energy source supply appliance 104) and/or (ii) one or more receiver vehicles of receiver vehicle(s) 109 that are configured to receive the second energy source (e.g., receiver vehicle 111). In some embodiments, second hub energy source supply subsystem 120 can be configured to receive the second energy source so that second hub energy source supply subsystem 120 can make available the second energy source to (i) the one or more energy source supply appliances of energy source supply appliance(s) 102 (e.g., energy source supply appliance 103 and/or energy source supply appliance 104) and/or (ii) the one or more receiver vehicles of receiver vehicle(s) 109 that are configured to receive the second energy source (e.g., receiver vehicle 111). In these or other embodiments, second hub energy source supply subsystem 120 can be configured to convert (e.g., electrochemically convert) the first energy source to the second energy source so that second hub energy source supply subsystem 120 can make available the second energy source to (i) the one or more energy source supply appliances of energy source supply appliance(s) 102 (e.g., energy source supply appliance 103 and/or energy source supply appliance 104) and/or (ii) the one or more receiver vehicles of receiver vehicle(s) 109 that are configured to receive the second energy source (e.g., receiver vehicle 111). For example, in some embodiments, the first energy source can comprise a hydrogen fuel energy source or a natural gas energy fuel energy source, the second energy source can comprise an electrical energy source (i.e., electricity), and second hub energy source supply subsystem 120 can convert (e.g., electrochemically convert) the hydrogen fuel energy source or the natural gas energy fuel energy source to the electrical energy source, such as, for example, using one or more fuel cells. In other embodiments, the first energy source can comprise an electrical energy source (i.e., electricity), the second energy source can comprise a hydrogen fuel energy source or a natural gas energy fuel energy source, and second appliance energy source supply subsystem 120 can convert (e.g., electrochemically convert) the electrical energy source to the hydrogen fuel energy source or the natural gas energy fuel energy source, such as, for example, using electrolysis or other electrochemical conversion.

In many embodiments, second hub energy source supply subsystem 120 can be configured to receive the second energy source so that second hub energy source supply subsystem 120 can make available the second energy source to the one or more receiver vehicles of receiver vehicle(s) 109 (e.g., receiver vehicle 111) that are configured to receive the second energy source. For example, in some embodiments, second hub energy source supply subsystem 120 can be configured to receive the first energy source from first hub energy source supply subsystem 119 and/or energy source supply station(s) 107 (e.g., energy source supply station 108), as further described below. In further embodiments, second hub energy source supply subsystem 120 can be configured to receive the second energy source from energy source supply station(s) 107 (e.g., energy source supply station 108), as further described below.

In these or other embodiments, second hub energy source supply subsystem 120 can be configured to produce (e.g., generate) the second energy source at second hub energy source supply subsystem 120 so that second hub energy source supply subsystem 120 can make available the second energy source to (i) the one or more energy source supply appliances of energy source supply appliance(s) 102 (e.g., energy source supply appliance 103 and/or energy source supply appliance 104) and/or (ii) the one or more receiver vehicles of receiver vehicle(s) 109 that are configured to receive the second energy source (e.g., receiver vehicle 111). In some embodiments, such as, for example, when the second energy source comprises a hydrogen fuel energy source, second hub energy source supply subsystem 120 can be configured to produce (e.g., generate) the second energy source at second hub energy source supply subsystem 120 from water, such as, for example, using electrolysis. In these embodiments, second hub energy source supply subsystem 120 can be configured to receive water in order to produce the hydrogen fuel energy source at second hub energy source supply subsystem 120. In other embodiments, such as, for example, when the second energy source comprises an electrical energy source (i.e., electricity), second hub energy source supply subsystem 120 can be configured to produce (e.g., generate) the second energy source at second hub energy source supply subsystem 120 from a power plant, such as, for example, a solar energy power plant or a wind energy power plant. In these embodiments, second hub energy source supply subsystem 120 can comprise the power plant. In still other embodiments, second hub energy source supply subsystem 120 can be configured to receive but not to produce (e.g., generate) the second energy source made available by second hub energy source supply subsystem 120 to (i) the one or more energy source supply appliances of energy source supply appliance(s) 102 (e.g., energy source supply appliance 103 and/or energy source supply appliance 104) and/or (ii) the one or more receiver vehicles of receiver vehicle(s) 109 that are configured to receive the second energy source (e.g., receiver vehicle 111).

In many embodiments, second hub energy source supply subsystem 120 can be configured to store the second energy source so that second hub energy source supply subsystem 120 can make available the second energy source to (i) the one or more energy source supply appliances of energy source supply appliance(s) 102 (e.g., energy source supply appliance 103 and/or energy source supply appliance 104) and/or (ii) the one or more receiver vehicles of receiver vehicle(s) 109 that are configured to receive the second energy source (e.g., receiver vehicle 111). In many embodiments, second hub energy source supply subsystem 120 can comprise a hub second energy source storage capacity. In further embodiments, the hub second energy source storage capacity can be greater than the appliance second energy source storage capacity described above with respect to energy source supply appliance 103 and second appliance energy source supply subsystem 116. For example, in some embodiments, the hub second energy source storage capacity can be approximately 6, 7, 8, 9, or 10 times greater than the appliance second energy source storage capacity. In these or other embodiments, when the second energy source comprises a fuel energy source, second hub energy source supply subsystem 120 can be configured to store the second energy source under pressure so that second hub energy source supply subsystem 120 can store more of the second energy source. In further embodiments, second hub energy source supply subsystem 120 can be configured to store the second energy source under a pressure greater than the pressure at which second appliance energy source supply subsystem 116 stores the second energy source.

Returning to other parts of energy source supply hub 106, hub vehicle 121 can comprise hub vehicle drive system 126, and hub vehicle drive system 126 can be configured to motively power hub vehicle 121. In some embodiments, hub vehicle drive system 126 can be configured to receive at least one energy source of the one or more energy sources made available to energy source supply appliance(s) 102 (e.g., energy source supply appliance 103 and/or energy source supply appliance 104) and/or receiver vehicle(s) 109 (e.g., receiver vehicle 110 and/or receiver vehicle 111) by energy source supply hub 106 to be used to motively power hub vehicle 121. In other embodiments, hub vehicle drive system 126 can use another energy source to motively power hub vehicle 121.

In many embodiments, energy source supply station(s) 107 can comprise energy source supply station 108. In some embodiments, when energy source supply station(s) 107 comprise multiple energy source supply stations, one or more energy source supply stations of the multiple energy source supply stations can be similar or identical to one or more other energy source supply stations of the multiple energy source supply stations. In these or other embodiments, when energy source supply stations(s) 107 comprise multiple energy source supply stations, one or more energy source supply stations of the multiple energy source supply stations can be different than one or more other energy source supply stations of the multiple energy source supply stations. In other embodiments, one or more other energy source supply stations of energy source supply stations(s) 107 can be similar or identical to energy source supply station 108.

Energy source supply station(s) 107 (e.g., energy source supply station 108) each can be configured to make available one or more energy sources to (i) one or more energy source supply hubs of energy source supply hub(s) 105 (e.g., energy source supply hub 106), (ii) one or more energy source supply appliances of energy source supply appliance(s) 102 (e.g., energy source supply appliance 103 and/or energy source supply appliance 104) and/or (iii) one or more receiver vehicles of receiver vehicle(s) 109 (e.g., receiver vehicle 110 and/or receiver vehicle 111). In some embodiments, at least one energy source supply station of energy source supply station(s) 107 (e.g., energy source supply station 108) can be configured (i) to make available multiple different energy sources to energy source supply hub(s) 105, such as, for example, when energy source supply hub(s) 105 comprise one or more binary energy source supply hubs and/or two or more unary energy source supply hubs configured to make available different energy sources to energy source supply appliance(s) 102 and/or receiver vehicle(s) 109, (ii) to make available multiple different energy sources to energy source supply appliance(s) 102, such as, for example, when energy source supply appliance(s) 102 comprise one or more binary energy source supply appliances and/or two or more unary energy source supply appliances configured to make available different energy sources to receiver vehicle(s) 109, and/or (iii) to make available multiple different energy sources to receiver vehicle(s) 109. As defined herein, a "unary energy source supply station" can refer to an energy source supply station of energy source supply station(s) 107 that is configured to make available one energy source to energy source supply hub(s) 105, energy source supply appliance(s) 102, and/or receiver vehicle(s) 109, and a "binary energy source supply station" can refer to an energy source supply station of energy source supply station(s) 107 that is configured to make available two different energy sources to energy source supply hub(s) 105, energy source supply appliance(s) 102, and/or receiver vehicle(s) 109.

In many embodiments, energy source supply station 108 comprises station energy source supply system 122. Station energy source supply system 122 comprises first station energy source supply subsystem 123. In some embodiments, station energy source supply system 122 also can comprise second station energy source supply subsystem 124. In other embodiments, second station energy source supply subsystem 124 can be omitted.

In many embodiments, energy source supply station 108 can comprise a facility or plant configured to make available one or more energy sources to (i) one or more energy source supply hubs of energy source supply hub(s) 105 (e.g., energy source supply hub 106), (ii) one or more energy source supply appliances of energy source supply appliance(s) 102 (e.g., energy source supply appliance 103 and/or energy source supply appliance 104) and/or (iii) one or more receiver vehicles of receiver vehicle(s) 109 (e.g., receiver vehicle 110 and/or receiver vehicle 111). In some embodiments, the facility or plant can be stationary or permanently installed at a site (i.e., energy source supply station 108 can be stationary). In some embodiments, the facility or plant can be configured to generate the one or more energy sources made available to (i) one or more energy source supply hubs of energy source supply hub(s) 105 (e.g., energy source supply hub 106), (ii) one or more energy source supply appliances of energy source supply appliance(s) 102 (e.g., energy source supply appliance 103 and/or energy source supply appliance 104) and/or (iii) one or more receiver vehicles of receiver vehicle(s) 109 (e.g., receiver vehicle 110 and/or receiver vehicle 111).

First station energy source supply subsystem 123 can make available the first energy source to (i) one or more energy source supply hubs of energy source supply hub(s) 105 (e.g., energy source supply hub 106), (ii) one or more energy source supply appliances of energy source supply appliance(s) 102 (e.g., energy source supply appliance 103 and/or energy source supply appliance 104) and/or (iii) one or more receiver vehicles of receiver vehicle(s) 109 that are configured to receive the first energy source (e.g., receiver vehicle 110). In these or other embodiments, first station energy source supply subsystem 123 can make available the first energy source to second station energy source supply subsystem 124, such as, for example, so that second station energy source supply subsystem 124 can convert (e.g., electrochemically convert) the first energy source to the second energy source as described in greater detail below. In other embodiments, first station energy source supply subsystem 123 can make available the first energy source to second station energy source supply subsystem 124 but not (i) energy source supply hub(s) 105, (ii) energy source supply appliance(s) 102, and/or (iii) receiver vehicle(s) 109.

In many embodiments, first station energy source supply subsystem 123 can be configured to receive the first energy source so that first station energy source supply subsystem 123 can make available the first energy source to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104), (iii) the one or more receiver vehicles of receiver vehicle(s) 109 that are configured to receive the first energy source (e.g., receiver vehicle 110), and/or (iv) to second station energy source supply subsystem 124. In some embodiments, such as, for example, when the first energy source comprises an electrical energy source (i.e., electricity), first station energy source supply subsystem 123 can be configured to receive the first energy source from a utility electric grid.

In these or other embodiments, first station energy source supply subsystem 123 can be configured to produce (e.g., generate) the first energy source at first station energy source supply subsystem 123 so that first station energy source supply subsystem 123 can make available the first energy source to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104), (iii) the one or more receiver vehicles of receiver vehicle(s) 109 that are configured to receive the first energy source (e.g., receiver vehicle 110), and/or (iv) to second station energy source supply subsystem 124. In some embodiments, such as, for example, when the first energy source comprises a hydrogen fuel energy source, first station energy source supply subsystem 123 can be configured to produce (e.g., generate) the first energy source at first station energy source supply subsystem 123 from water, such as, for example, using electrolysis. In these embodiments, first station energy source supply subsystem 123 can be configured to receive water in order to produce the hydrogen fuel energy source at first station energy source supply subsystem 123. In other embodiments, such as, for example, when the first energy source comprises an electrical energy source (i.e., electricity), first station energy source supply subsystem 123 can be configured to produce (e.g., generate) the first energy source at first station energy source supply subsystem 123 from a power plant, such as, for example, a solar energy power plant or a wind energy power plant. In these embodiments, first station energy source supply subsystem 123 can comprise the power plant. In still other embodiments, first station energy source supply subsystem 123 can be configured to receive but not to produce (e.g., generate) the first energy source made available by first station energy source supply subsystem 123 to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104), (iii) the one or more receiver vehicles of receiver vehicle(s) 109 that are configured to receive the first energy source (e.g., receiver vehicle 110), and/or (iv) to second station energy source supply subsystem 124.

In many embodiments, first station energy source supply subsystem 123 can be configured to store the first energy source so that first station energy source supply subsystem 123 can make available the first energy source to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104), (iii) the one or more receiver vehicles of receiver vehicle(s) 109 that are configured to receive the first energy source (e.g., receiver vehicle 110), and/or (iv) to second station energy source supply subsystem 124. In many embodiments, first station energy source supply subsystem 123 can comprise a station first energy source storage capacity. In further embodiments, the station first energy source storage capacity can be greater than the hub first energy source storage capacity described above with respect to energy source supply hub 105 and first hub energy source supply subsystem 119. For example, in some embodiments, the station first energy source storage capacity can be approximately 5-20 times greater than the hub first energy source storage capacity. In these or other embodiments, when the first energy source comprises a fuel energy source, first station energy source supply subsystem 123 can be configured to store the first energy source under pressure so that first station energy source supply subsystem 123 can store more of the first energy source. In further embodiments, first station energy source supply subsystem 123 can be configured to store the first energy source under a pressure greater than the pressure at which first hub energy source supply subsystem 119 stores the first energy source.

Further, in some embodiments, second station energy source supply subsystem 124 can make available the second energy source to (i) one or more energy source supply hubs of energy source supply hub(s) 105 (e.g., energy source supply hub 106), (ii) one or more energy source supply appliances of energy source supply appliance(s) 102 (e.g., energy source supply appliance 103 and/or energy source supply appliance 104) and/or (iii) one or more receiver vehicles of receiver vehicle(s) 109 that are configured to receive the second energy source (e.g., receiver vehicle 111).

In some embodiments, second station energy source supply subsystem 124 can be configured to receive the second energy source so that second station energy source supply subsystem 124 can make available the second energy source to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104) and/or (iii) the one or more receiver vehicles of receiver vehicle(s) 109 that are configured to receive the second energy source (e.g., receiver vehicle 111). In some embodiments, such as, for example, when the second energy source comprises an electrical energy source (i.e., electricity), second station energy source supply subsystem 124 can be configured to receive the second energy source from a utility electric grid.

In these or other embodiments, second station energy source supply subsystem 124 can be configured to convert (e.g., electrochemically convert) the first energy source to the second energy source so that second station energy source supply subsystem 124 can make available the second energy source to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104) and/or (iii) the one or more receiver vehicles of receiver vehicle(s) 109 that are configured to receive the second energy source (e.g., receiver vehicle 111). For example, in some embodiments, the first energy source can comprise a hydrogen fuel energy source or a natural gas energy fuel energy source, the second energy source can comprise an electrical energy source (i.e., electricity), and second station energy source supply subsystem 124 can convert (e.g., electrochemically convert) the hydrogen fuel energy source or the natural gas energy fuel energy source to the electrical energy source, such as, for example, using one or more fuel cells. In other embodiments, the first energy source can comprise an electrical energy source (i.e., electricity), the second energy source can comprise a hydrogen fuel energy source or a natural gas energy fuel energy source, and second station energy source supply subsystem 124 can convert (e.g., electrochemically convert) the electrical energy source to the hydrogen fuel energy source or the natural gas energy fuel energy source, such as, for example, using electrolysis or other electrochemical conversion. In some embodiments, second station energy source supply subsystem 124 can be configured to receive the first energy source from first station energy source supply subsystem 123.

In these or other embodiments, second station energy source supply subsystem 124 can be configured to produce (e.g., generate) the second energy source at second station energy source supply subsystem 124 so that second station energy source supply subsystem 124 can make available the second energy source to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104), and/or (iii) the one or more receiver vehicles of receiver vehicle(s) 109 that are configured to receive the second energy source (e.g., receiver vehicle 111). In some embodiments, such as, for example, when the second energy source comprises a hydrogen fuel energy source, second station energy source supply subsystem 124 can be configured to produce (e.g., generate) the second energy source at second station energy source supply subsystem 124 from water, such as, for example, using electrolysis. In these embodiments, second station energy source supply subsystem 124 can be configured to receive water in order to produce the hydrogen fuel energy source at second station energy source supply subsystem 124. In other embodiments, such as, for example, when the second energy source comprises an electrical energy source (i.e., electricity), second station energy source supply subsystem 124 can be configured to produce (e.g., generate) the second energy source at second station energy source supply subsystem 124 from a power plant, such as, for example, a solar energy power plant or a wind energy power plant. In these embodiments, second station energy source supply subsystem 124 can comprise the power plant. In still other embodiments, second station energy source supply subsystem 124 can be configured to receive but not to produce (e.g., generate) the second energy source made available by second station energy source supply subsystem 124 to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104), and/or (iii) the one or more receiver vehicles of receiver vehicle(s) 109 that are configured to receive the second energy source (e.g., receiver vehicle 111).

In many embodiments, second station energy source supply subsystem 124 can be configured to store the second energy source so that second station energy source supply subsystem 124 can make available the second energy source to (i) the one or more energy source supply hubs of energy source supply hub(s) 105 (e.g., energy source supply hub 106), (ii) the one or more energy source supply appliances of energy source supply appliance(s) 102 (e.g., energy source supply appliance 103 and/or energy source supply appliance 104) and/or (iii) the one or more receiver vehicles of receiver vehicle(s) 109 that are configured to receive the second energy source (e.g., receiver vehicle 111). In many embodiments, second station energy source supply subsystem 124 can comprise a station second energy source storage capacity. In further embodiments, the station second energy source storage capacity can be greater than the hub second energy source storage capacity described above with respect to energy source supply hub 105 and second hub energy source supply subsystem 120. For example, in some embodiments, the station second energy source storage capacity can be approximately 5-15 times greater than the hub second energy source storage capacity. In these or other embodiments, when the second energy source comprises a fuel energy source, second station energy source supply subsystem 124 can be configured to store the second energy source under pressure so that second station energy source supply subsystem 124 can store more of the second energy source. In further embodiments, second station energy source supply subsystem 124 can be configured to store the second energy source under a pressure greater than the pressure at which second hub energy source supply subsystem 120 stores the second energy source.

In many embodiments, system 100 (e.g., energy source supply device(s) 101) can be configured to make available one or more energy sources to receiver vehicle(s) 109 in stages. For example, in some embodiments, system 100 (e.g., energy source supply device(s) 101) can be configured to make available one or more energy sources to receiver vehicle(s) 109 in two stages. In these embodiments, energy source supply appliance(s) 102 (e.g., energy source supply appliance 103 and/or energy source supply appliance 104) can receive at least one energy source from energy source supply station(s) 107 (e.g., energy source supply station 108) and, then, energy source supply appliance(s) 102 (e.g., energy source supply appliance 103 and/or energy source supply appliance 104) can make available one or more energy sources to receiver vehicle(s) 109 (e.g., receiver vehicle 110 and/or receiver vehicle 111).

In other embodiments, system 100 (e.g., energy source supply device(s) 101) can be configured to make available one or more energy sources to receiver vehicle(s) 109 in three stages. In these embodiments, energy source supply hub(s) 105 (e.g., energy source supply hub 106) can receive at least one energy source from energy source supply station(s) 107 (e.g., energy source supply station 108) and, then, energy source supply hub(s) 105 (e.g., energy source supply hub 106) can make available one or more energy sources to energy source supply appliance(s) 102 (e.g., energy source supply appliance 103 and/or energy source supply appliance 104) and, then, energy source supply appliance(s) 102 (e.g., energy source supply appliance 103 and/or energy source supply appliance 104) can make available one or more energy sources to receiver vehicle(s) 109 (e.g., receiver vehicle 110 and/or receiver vehicle 111).

Meanwhile, although system 100 (e.g., energy source supply device(s) 101) is generally described with respect to two and three stage implementations herein, in further embodiments, the principles of system 100 can be extended so that system 100 can be implemented with any suitable number of stages. In these embodiments, the energy source storage capacity, and in some embodiments, the storage pressures of energy source supply device(s) 101 can decrease as the stages approach vehicle(s) 109 and can increase as the stages approach energy source supply station(s) 107.

Further, although energy source supply device(s) 101 are generally described such that the first energy source, the second energy source, etc. remain consistent for each of energy source supply device(s) 101, in some embodiments, when energy source supply device(s) 101 comprise multiple energy source supply devices, the types of energy sources implemented for the first energy source, the second energy source, etc. can differ between two or more of the multiple energy source supply devices. For example, in some embodiments, energy source supply station 108 can implement a first energy source comprising an electrical energy source, and a second energy source comprising a hydrogen fuel energy source or a natural gas energy fuel energy source. Meanwhile, in these or other embodiments, one or more of energy source supply hub 106, energy source supply appliance 103, and/or energy source supply appliance 104 can implement a first energy source comprising the hydrogen fuel energy source or the natural gas energy fuel energy source, and a second energy source comprising the electrical energy source. Accordingly, in these embodiments, the one or more of energy source supply hub 106, energy source supply appliance 103, and/or energy source supply appliance 104 can receive the second energy source of energy source supply station 108 as the first energy source of the one or more of energy source supply hub 106, energy source supply appliance 103, and/or energy source supply appliance 104.

Because system 100 (e.g., energy source supply device(s) 101) can be configured to make available one or more energy sources to receiver vehicle(s) 109 in stages, system 100 (e.g., energy source supply device(s) 101) can advantageously permit vehicle(s) 109 to be operated in one or more regions that lack sufficient or any access to the energy source(s) to otherwise permit operation of vehicle(s) 109 therein (i.e., one or more unsupported regions). For example, in some embodiments, energy source supply station(s) 107 (e.g., energy source supply station 108) may be located too far from the unsupported region(s) for energy source supply station(s) 107 (e.g., energy source supply station 108) to directly make available the energy source(s) to vehicle(s) 109 when vehicle(s) 109 are being operating in the unsupported region(s). Additional factors, including local driving conditions, weather, current energy source availability at energy source supply station(s) 107, operating conditions of vehicle(s) 109, etc., also may contribute to defining the unsupported region(s). However, because system 100 (e.g., energy source supply device(s) 101) can be configured to make available the energy source(s) to receiver vehicle(s) 109 in stages, and because energy source supply device(s) 101 can be mobile, system 100 (e.g., energy source supply device(s) 101) can increase an effective service range of energy source supply station(s) 107 (e.g., energy source supply station 108) in order to make available the energy source(s) in the unsupported regions.

Further, because system 100 (e.g., energy source supply device(s) 101) can be configured to make available one or more energy sources to receiver vehicle(s) 109 in stages, and because energy source supply device(s) 101 can be mobile, system 100 (e.g., energy source supply device(s) 101) can advantageously permit vehicle(s) 109 to optimally make available the energy source(s) to receiver vehicle(s) 109. For example, in many embodiments, when multiple energy source supply device(s) 101 comprise multiple energy source supply devices, energy source supply device(s) 101 can be operated in multiple operating zones to optimally make available the energy source(s) to receiver vehicle(s) 109. Operating energy supply device(s) 101 in multiple operating zones can permit energy source supply device(s) 101 to more quickly, cost-effectively, and/or capably make available one or more energy sources to receiver vehicle(s) 109.

For example, when system 100 (e.g., energy source supply device(s) 101) is being implemented to make available one or more energy sources to receiver vehicle(s) 109 in three stages, and when energy source supply hub(s) 105 (e.g., energy source supply hub 106) are larger than energy source supply appliance(s) 102 (e.g., energy source supply appliance 103 and/or energy source supply appliance 104), energy source supply hub(s) 105 may not be able to access receiver vehicle(s) 109 as quickly as energy source supply appliance(s) 102 can or may not be able to access receiver vehicle(s) 109 at all, such as, for example, due to geography and/or road infrastructure. Accordingly, in these or other embodiments, energy source supply appliance(s) 102 (e.g., energy source supply appliance 103 and/or energy source supply appliance 104) can be operated in one or more appliance operating zones and energy source supply hub(s) 105 (e.g., energy source supply hub 106) can be operated in one or more hub operating zones. Further, the appliance operating zone(s) and the hub operating zone(s) can be positioned such that the appliance operating zone(s) are near enough to the hub operating zone(s) to permit energy source supply hub(s) 105 (e.g., energy source supply hub 106) to make available the one or more energy sources to energy source supply appliance(s) 102 (e.g., energy source supply appliance 103 and/or energy source supply appliance 104) while permitting energy source supply appliance(s) 102 (e.g., energy source supply appliance 103 and/or energy source supply appliance 104) to cover more territory than energy source supply hub(s) 105 (e.g., energy source supply hub 106) may be able to cover alone and/or while permitting energy source supply appliance(s) 102 (e.g., energy source supply appliance 103 and/or energy source supply appliance 104) to reach receiver vehicle(s) 109 more quickly within the appliance operating zone(s) than energy source supply hub(s) 105 (e.g., energy source supply hub 106) may be able to do.

In some embodiments, two or more of the multiple operating zones in which system 100 (e.g., energy source supply device(s) 101) is being operated can overlap each other. For example, in some embodiments, one or more appliance operating zones can overlap at least one hub operating zone. In these or other embodiments, two or more appliance operating zones can overlap each other. However, in other embodiments, one or more appliance zones may not or even no appliance zones may overlap any hub operating zone(s) and/or another appliance zone.

In these or other embodiments, the configuration or configurations (e.g., location, shape, overlap, etc.) of the multiple operating zones in which system 100 (e.g., energy source supply device(s) 101) is being operated can be determined according to one or more zone pattern factors. For example, the zone pattern factor(s) can be applied to one or more algorithms configured to define the configuration or configurations (e.g., location, shape, overlap, etc.) of the multiple operating zones in which system 100 (e.g., energy source supply device(s) 101) is being operated. Exemplary zone pattern factors can include traffic (e.g., actual and/or modeled), weather (e.g., actual and/or modeled), road placement, empirical testing, service requests from one or more operators of receiver vehicle(s) 109 (e.g., by voice, email, text message, or any other suitable communication media), observations submitted by one or more operators of receiver vehicle(s) 109 and/or energy source supply device(s) 101, etc. Further, in these or other embodiments, the zone pattern factor(s) can determine the position(s) of energy source supply device(s) 101 and/or the manner of operation of energy source supply device(s) 101 within the multiple operating zones in which system 100 (e.g., energy source supply device(s) 101) is being operated, and/or the travel time(s) to receiver vehicle(s) 109 based on the position(s). In some embodiments, when multiple zone pattern factor(s) are considered, two or more zone pattern factor(s) can be weighted the same or differently than each other. For example, in many embodiments, travel time(s) can be weighted more heavily than one or more other zone pattern factors. In some embodiments, the position(s) and/or travel time(s) of energy source supply device(s) 101 can be determined from telemetry provided by the energy source supply device(s) 101. In some embodiment, the configurations (e.g., locations, shapes, etc.) of the multiple operating zones in which system 100 (e.g., energy source supply device(s) 101) is being operated, the position(s) of energy source supply device(s) 101 within the multiple operating zones, and/or the manner of operation of energy source supply device(s) 101 within the multiple operating zones can be changed or updated in real time.

Figure 2:
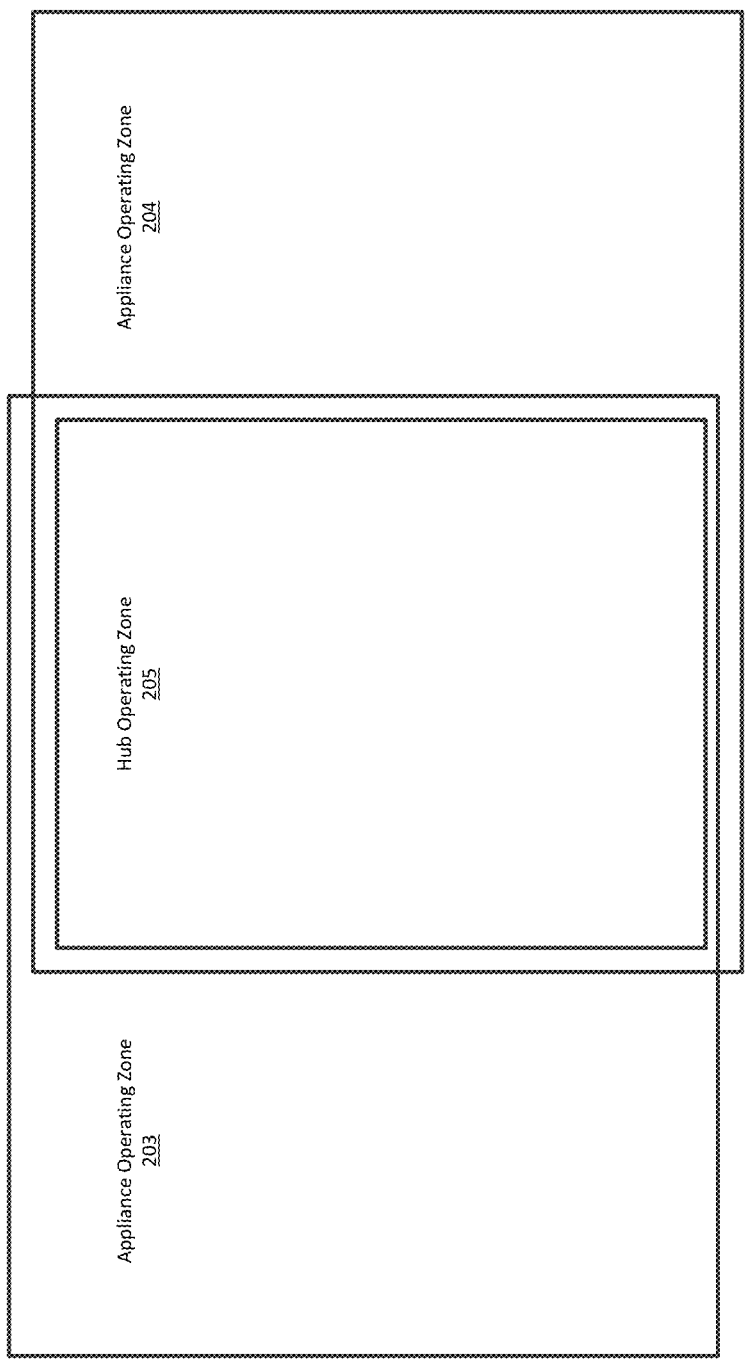
FIG. 2 illustrates a diagram of a first appliance operating zone, a second appliance operating zone, and a hub operating zone, according to an embodiment.

Turning ahead briefly in the drawings, FIG. 2 illustrates a diagram of appliance operating zone 203, appliance operating zone 204, and hub operating zone 205, according to an embodiment. In many embodiments, appliance operating zone 203 can correspond to a first energy source supply appliance, appliance operating zone 204 can correspond to a second energy source supply appliance, and hub operating zone 205 can correspond to an energy source supply hub. In one embodiment, the first energy source supply appliance can be similar or identical to energy source supply appliance 103 (FIG. 1); the second energy source supply appliance can be similar or identical to energy source supply appliance 104 (FIG. 1); and the energy source supply hub can be similar or identical to energy source supply hub 105 (FIG. 1). Further, appliance operating zone 203 and appliance operating zone 204 can be similar or identical to the appliance operating zones described above with respect to system 100 (FIG. 1), and hub operating zone 205 can be similar or identical to one of the hub operating zones described above with respect to system 100 (FIG. 1). The size, geography, area, and/or shape of appliance operating zones 203 and 204 can be similar or different from each other.

Turning again to FIG. 1, in many embodiments, implementing system 100 (e.g., energy source supply device(s) 101) to make available one or more energy sources to receiver vehicle(s) 109 in stages, and when applicable, in multiple operating zones, can be advantageous when one of the energy source(s) is a hydrogen energy source. For example, a humidity of the hydrogen energy source, a purity of the hydrogen energy source, a temperature of the hydrogen energy source, and a pressure of the hydrogen energy source (collectively, a fuel quality of the hydrogen energy source) can impact whether or not the hydrogen energy source can be successfully made available to receiver vehicle(s) 109. Because system 100 (e.g., energy source supply device(s) 101) can permit energy source supply device(s) 101 to more quickly and/or capably make available a hydrogen energy source to receiver vehicle(s) 109, a fuel quality of the hydrogen energy source can be better controlled. For example, by making available a hydrogen energy source to receiver vehicle(s) 109 more quickly and/or capably, there is less opportunity for the fuel quality of the hydrogen energy source to change (e.g., degrade) between energy source supply station(s) 107 and receiver vehicle(s) 109.

In many embodiments, when energy source supply device(s) 101 comprise multiple energy source supply devices, one or more energy source supply devices of the multiple energy source supply devices can be configured to make available one or more energy sources to one or more other energy source supply devices of the multiple energy source supply devices, and vice versa. Further, in these embodiments, one or more (e.g., all) of the other energy source supply device(s) of the multiple energy source supply devices can be configured to receive one or more of the energy source(s) from the energy source supply device(s) of the multiple energy source supply devices making available the energy source(s).

For example, in some embodiments, when energy source supply appliance(s) 102 comprise multiple energy source supply appliances (e.g., energy source supply appliance 103 and energy source supply appliance 104), one or more energy source supply appliances of the multiple energy source supply appliances (e.g., energy source supply appliance 103) can be configured to make available one or more energy sources to one or more other energy source supply appliances of the multiple energy source supply appliances (e.g., energy source supply appliance 104), and vice versa. Further, in these embodiments, one or more (e.g., all) of the other energy source supply appliance(s) of the multiple energy source supply appliances can be configured to receive one or more of the energy source(s) from the energy source supply appliance(s) of the multiple energy source supply appliances making available the energy source(s).

In these or other embodiments, when energy source supply hub(s) 105 comprise multiple energy source supply hubs, one or more energy source supply hubs of the multiple energy source supply hubs (e.g., energy source supply hub 106) can be configured to make available one or more energy sources to one or more other energy source supply hubs of the multiple energy source supply hubs, and vice versa. Further, in these embodiments, one or more (e.g., all) of the other energy source supply hub(s) of the multiple energy source supply hubs can be configured to receive one or more of the energy source(s) from the energy source supply hub(s) of the multiple energy source supply hubs making available the energy source(s).

In some embodiments, when energy source supply device(s) 101 comprise multiple energy source supply devices, an energy source supply device of energy source supply device(s) 101 (e.g., energy source supply appliance 104) receiving one or more energy sources from another energy source supply device of energy source supply device(s) 101 (e.g., energy source supply appliance 103) can simulate a receiver vehicle of receiver vehicle(s) 109 so that the energy source supply device supplying the one or more energy source(s) can be tested and/or calibrated. For example, in some embodiments, one or more sensors (e.g., one or more temperature sensors, one or more pressure sensors, one or more voltage sensors, one or more current sensors, etc.) of the energy source supply device of energy source supply device(s) 101 (e.g., energy source supply appliance 103) supplying the energy source(s) can be compared to one or more sensors (e.g., one or more temperature sensors, one or more pressure sensors, one or more voltage sensors, one or more current sensors, etc.) of the energy source supply device of energy source supply device(s) 101 (e.g., energy source supply appliance 104) receiving the energy source(s) to determine whether the sensor(s) of the energy source supply device supplying the energy source(s) provide the same or similar (e.g., within a range of error acceptable to the operator of system 100) measurement values to the sensor(s) of the energy source supply device receiving the energy source(s). In some embodiments, one or more (e.g., all) of energy source supply device(s) 101 can be tested and/or calibrated by one or more others of energy source supply device(s) 101, such as, for example, when at least one other energy source supply device of energy source supply device(s) 101 configured to make available the same energy source(s) as the energy source supply device(s) that are tested and/or calibrated is implemented with system 100. In further embodiments, an energy source supply device of energy source supply device(s) 101 that is configured to make available one or more but not all of the energy sources made available by the energy source supply device being tested and/or calibrated may, in some embodiments, be able to be used for testing and/or calibrating at least part of the energy source supply device being tested and/or calibrated.

Simulating a receiver vehicle of receiver vehicle(s) 109 with an energy source supply device of energy source supply device(s) 101 (e.g., energy source supply appliance 104) to test and/or calibrate another energy source supply device of energy source supply device(s) 101 (e.g., energy source supply appliance 103) rather than testing and/or calibrating the other energy source supply device with a receiver vehicle of receiver vehicle(s) 109 can be advantageous for one or more reasons. In some embodiments, simulating a receiver vehicle of receiver vehicle(s) 109 with an energy source supply device of energy source supply device(s) 101 (e.g., energy source supply appliance 104) to test and/or calibrate another energy source supply device of energy source supply device(s) 101 (e.g., energy source supply appliance 103) rather than testing and/or calibrating the other energy source supply device with a receiver vehicle of receiver vehicle(s) 109 advantageously may permit the energy source supply device of energy source supply device(s) 101 to be tested and/or calibrated over a wider range of sensed values (e.g., pressure, temperature, voltage, current, etc.) than may be possible when a receiver vehicle of receiver vehicle(s) 109 is used. For example, when a receiver vehicle of receiver vehicle(s) 109 is equipped with one or more devices configured to limit an operational range of the receiver vehicle, such as, for example, for purposes of safety and/or to mitigate wear on the receiver vehicle, and when the operational range of the receiver vehicle is smaller than an operational range of the energy source supply device of energy source supply device(s) 101 (e.g., energy source supply appliance 103) being tested and/or calibrated, simulating the receiver vehicle with another energy source supply device of energy source supply device(s) 101 (e.g., energy source supply appliance 104) can permit the energy source supply device of energy source supply device(s) 101 being tested and/or calibrated to be calibrated and/or tested outside of the limited operational range of the receiver vehicle. In these or other embodiments, simulating a receiver vehicle of receiver vehicle(s) 109 with an energy source supply device of energy source supply device(s) 101 (e.g., energy source supply appliance 104) to test and/or calibrate another energy source supply device of energy source supply device(s) 101 (e.g., energy source supply appliance 103) rather than testing and/or calibrating the other energy source supply device with a receiver vehicle of receiver vehicle(s) 109 advantageously may prevent damage to the receiver vehicle of receiver vehicle(s) 109.

Figure 3:
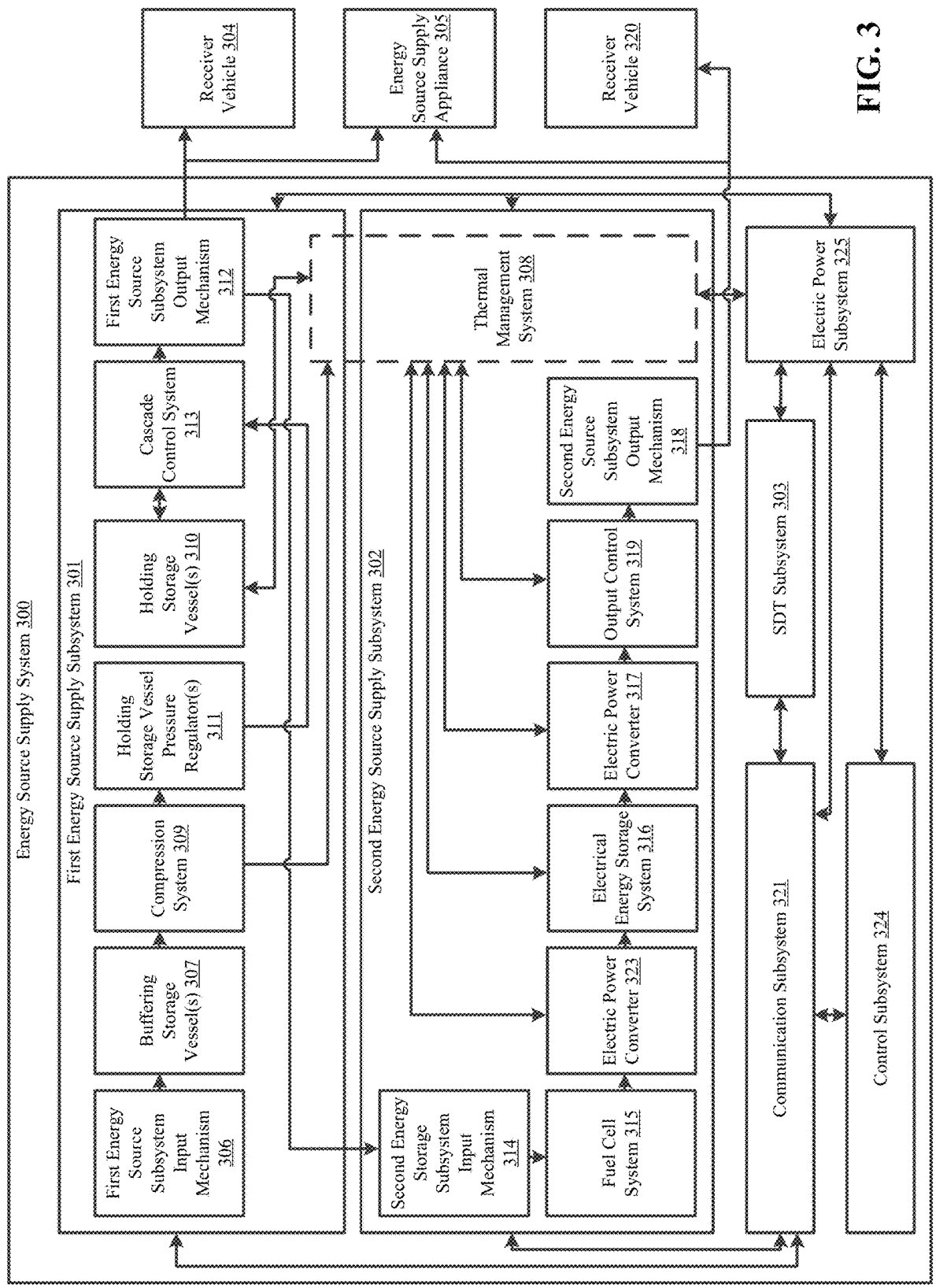
FIG. 3 illustrates an exemplary block diagram for an energy source supply system, according to an embodiment.

Turning ahead in the drawings, FIG. 3 illustrates an exemplary block diagram for energy source supply system 300, according to an embodiment. Energy source supply system 300 is merely exemplary and is not limited to the embodiments presented herein. Energy source supply system 300 can be employed in many different embodiments or examples not specifically depicted or described herein.

In some embodiments, energy source supply system 300 can be similar or identical to appliance energy source supply system 114 (FIG. 1), and vice versa. Accordingly, in these embodiments, energy source supply system 300 can be used to implement appliance energy source supply system 114 (FIG. 1) in system 100 (FIG. 1). In other embodiments, energy source supply system 300 can be similar or identical to hub energy source supply system 118 (FIG. 1), and vice versa. According, in these embodiments, energy source supply system 300 can be used to implement hub energy source supply system 118 (FIG. 1) in system 100 (FIG. 1).

In many embodiments, energy source supply system 300 can comprise first energy source supply subsystem 301. In further embodiments, energy source supply system 300 can comprise second energy source supply subsystem 302, safety, diagnostic, and telemetry (SDT) subsystem 303, communication subsystem 321, control subsystem 324, and/or electric power subsystem 325. However, in other embodiments, second energy source supply subsystem 302, SDT subsystem 303, communication subsystem 321, control subsystem 324, and/or electric power subsystem 325 can be omitted. Further, in some embodiments, part or all of second energy source supply subsystem 302 can be part of first energy source supply subsystem 301, and vice versa.

In some embodiments, such as, for example, when energy source supply system 300 is similar or identical to appliance energy source supply system 114 (FIG. 1), first energy source supply subsystem 301 can be similar or identical to first appliance energy source supply subsystem 115 (FIG. 1), and vice versa. In other embodiments, such as, for example, when energy source supply system 300 is similar or identical to hub energy source supply system 118 (FIG. 1), first energy source supply subsystem 301 can be similar or identical to first hub energy source supply subsystem 119 (FIG. 1), and vice versa.

For example, in some embodiments, first energy source supply subsystem 301 can be configured to make available a first energy source to second energy source supply subsystem 302, receiver vehicle 304, and/or energy source supply appliance 305. Further, the first energy source can comprise a hydrogen fuel energy source (e.g., a gaseous or liquid hydrogen fuel energy source), and the second energy source can comprise an electrical energy source. In many embodiments, receiver vehicle 304 can be similar or identical to one of receiver vehicle(s) 109 of FIG. 1 (e.g., receiver vehicle 110 (FIG. 1)). In these or other embodiments, energy source supply appliance 305 can be similar or identical to one of energy source supply appliances 102 of FIG. 1 (e.g., energy source supply appliance 103 (FIG. 1) and/or energy source supply appliance 104 (FIG. 1)). In other embodiments, first energy source supply subsystem 301 can make available the first energy source to second energy source supply subsystem 302 but not to receiver vehicle 304 and/or energy source supply appliance 305.

In these or other embodiments, first energy source supply subsystem 301 can comprise first energy source supply subsystem input mechanism 306, one or more buffering storage vessels 307, thermal management system 308, compression system 309, one or more holding storage vessels 310, one or more holding storage vessel pressure regulators 311, first energy source supply subsystem output mechanism 312, and cascade control system 313. In some embodiments, as described further herein, buffering storage vessel(s) 307, thermal management system 308, compression system 309, holding storage vessel pressure regulator(s) 311, and/or cascade control system 313 can be omitted.

In many embodiments, first energy source supply subsystem input mechanism 306 can be configured to receive the hydrogen fuel energy source. In implementation, first energy source supply subsystem input mechanism 306 can comprise one or more receptacles (e.g., one or more fittings) suitable to receive the hydrogen fuel energy source. In many embodiments, such as, for example, when energy source supply system 300 is similar or identical to hub energy source supply system 118 (FIG. 1), first energy source supply subsystem input mechanism 306 can receive the hydrogen fuel energy source from an energy storage supply station. Further, the energy storage supply station can be similar or identical to one of energy storage supply station(s) 107 of FIG. 1 (e.g., energy storage supply station 108 (FIG. 1)). In some embodiments, such as, for example, when energy source supply system 300 is similar or identical to appliance energy source supply system 114 (FIG. 1), first energy source supply subsystem input mechanism 306 can receive the hydrogen fuel energy source from an energy storage supply hub and/or the energy source supply station. Further, the energy storage supply hub can be similar or identical to one of energy storage supply hub(s) 105 of FIG. 1 (e.g., energy storage supply hub 106 (FIG. 1)).

In many embodiments, buffering storage vessel(s) 307 can be configured to receive the hydrogen fuel energy source from first energy source supply subsystem input mechanism 306 and to store the hydrogen fuel energy source. Accordingly, in some embodiments, buffering storage vessel(s) 307 can be coupled to first energy source supply subsystem input mechanism 306, such as, for example, by one or more conduits. In implementation, buffering storage vessel(s) 307 can comprise one or more tanks configured to store the hydrogen fuel energy source. In further embodiments, buffering storage vessel(s) 307 can store (e.g., temporarily store) the hydrogen fuel energy source until the hydrogen fuel energy source can be received by compression system 309.

In many embodiments, compression system 309 can be configured to receive the hydrogen fuel energy source from buffering storage vessel(s) 307. Accordingly, in some embodiments, compression system 309 can be coupled to buffering storage vessel(s) 307, such as, for example, by one or more conduits. Further, compression system 309 can be configured to compress the hydrogen fuel energy source to increase a pressure of the hydrogen fuel energy source and to provide the compressed hydrogen fuel energy source to holding storage vessel(s) 310. In implementation, compression system 309 can comprise a hydrogen compressor.

In many embodiments, holding storage vessel(s) 310 can be configured to receive and store the hydrogen fuel energy source. When buffering storage vessel(s) 307 and compression system 309 are implemented, holding storage vessel(s) 310 can be coupled to compression system 309, such as, for example, by one or more conduits, to receive the hydrogen fuel energy source from compression system 309 (e.g., after the hydrogen fuel energy source is compressed by compression system 309). Meanwhile, when buffering storage vessel(s) 307 and compression system 309 are omitted, holding storage vessel(s) 310 can be coupled (e.g., directly coupled) to first energy source supply subsystem input mechanism 306, such as, for example, by one or more conduits, to receive the hydrogen fuel energy source from first energy source supply subsystem input mechanism 306. Nonetheless, in many embodiments, implementing buffering storage vessel(s) 307 and compression system 309 can advantageously permit holding storage vessel(s) 310 to store more of the hydrogen fuel energy source.

In implementation, holding storage vessel(s) 310 can comprise one or more tanks configured to store the hydrogen fuel energy source. In many embodiments, holding storage vessel(s) 310 can comprise an aggregate storage capacity, and in some embodiments, each holding storage vessel of holding storage vessel(s) 310 can be configured to store the hydrogen fuel energy source approximately at or below a predetermined storage pressure. In some embodiments, the aggregate storage capacity of holding storage vessel(s) 310 can be greater than or equal to approximately 8 kilograms and less than or equal to approximately 73 kilograms. For example, the aggregate storage capacity of holding storage vessel(s) 310 can be approximately 8.4 kilograms. Further, in these or other embodiments, the predetermined storage pressure of holding storage vessel(s) 310 can be greater than or equal to approximately 34.47 Megapascals (gauge) and less than or equal to approximately 68.95 Megapascals (gauge).

In many embodiments, first energy source supply subsystem output mechanism 312 can be configured to receive the hydrogen fuel energy source from holding storage vessel(s) 310 and to make available the hydrogen fuel energy source to second energy source supply subsystem 302, receiver vehicle 304, and/or energy source supply appliance 305. Accordingly, in some embodiments, first energy source supply subsystem output mechanism 312 can be coupled to holding storage vessel(s) 310, such as, for example, by one or more conduits. In implementation, first energy source supply subsystem output mechanism 312 can comprise one or more hoses and/or nozzles suitable to receive the hydrogen fuel energy source and to make available the hydrogen fuel energy source to receiver vehicle 304 and/or energy source supply appliance 305. Further, when energy source supply system 300 comprises second energy source supply subsystem input 314, first energy source supply subsystem output mechanism 312 can comprise one or more conduits configured to make available the hydrogen fuel energy source to second energy source supply subsystem input 314, which is described further below. In some embodiments, first energy source supply subsystem output mechanism 312 can be configured to make available the hydrogen fuel energy source to second energy source supply subsystem 302 but not to receiver vehicle 304 and/or energy source supply appliance 305.

In many embodiments, holding storage vessel pressure regulator(s) 311 can be configured to limit a pressure of the hydrogen fuel energy source that is provided by compression system 309 to holding storage vessel(s) 310, such as, for example, via cascade control system 313. In implementation, holding storage vessel pressure regulator(s) 311 can comprise one or more pressure regulation valves. Further, holding storage vessel pressure regulator(s) 311 can be between compression system 309 and holding storage vessel(s) 310. Accordingly, in some embodiments, holding storage vessel pressure regulator(s) 311 can be coupled to compression system 309, such as, for example, by one or more conduits, and to cascade control system 313 or holding storage vessel(s) 310, such as, for example, by one or more conduits. In these or other embodiments, holding storage vessel pressure regulator(s) 311 can be implemented to prevent the pressure of the hydrogen fuel energy source being provided to holding storage vessel(s) 310 from exceeding the predetermined storage pressure of holding storage vessel(s) 310, thereby preventing damage to holding storage vessel(s) 310 and/or injury to the operator of energy source supply system 300. Nonetheless, in some embodiments, holding storage vessel pressure regulator(s) 311 can be omitted, such as, for example, when compression system 309 is omitted.

In many embodiments, cascade control system 313 can be implemented when holding storage vessel(s) 310 comprise multiple holding storage vessels. In particular, cascade control system 313 can be configured to control filling (e.g., by compression system 309 or first energy source supply subsystem input mechanism 306) of the multiple holding storage vessels with the hydrogen fuel energy source in a cascading manner and/or dispensing of the hydrogen fuel energy source (e.g., to first energy source supply subsystem output mechanism 312) from the multiple holding storage vessels in a cascading manner. In other embodiments, cascade control system 313 can be omitted, such as, for example, when holding storage vessel(s) 310 comprise only one holding storage vessel.

Although not illustrated in FIG. 3, in many embodiments, when energy source supply system 300 comprises cascade control system 313, cascade control system 313 can be between holding storage vessel(s) 310 and one of first energy source subsystem input mechanism 306, buffering storage vessel(s) 307, compression system 309, or holding storage vessel pressure regulator(s) 311. Accordingly, in some embodiments, cascade control system 313 can be coupled to holding storage vessel(s) 310 and at least one of first energy source subsystem input mechanism 306, buffering storage vessel(s) 307, compression system 309, or holding storage vessel pressure regulator(s) 311, such as, for example, by one or more conduits.

In other embodiments, when energy source supply system 300 comprises cascade control system 313, cascade control system 313 can be between holding storage vessel(s) 310 and first energy source subsystem output mechanism 312. Accordingly, in some embodiments, cascade control system 313 can be coupled to holding storage vessel(s) 310 and first energy source subsystem output mechanism 312, such as, for example, by one or more conduits.

In many embodiments, thermal management system 308 can be configured to thermally manage (e.g., cool) at least part of first energy source supply subsystem 301 (e.g., holding storage vessel(s) 310) to prevent or mitigate thermal stress on energy source supply system 300. In some embodiments, thermally managing (e.g., cooling) holding storage vessel(s) 310 can prevent holding storage vessel(s) 310 from overheating when holding storage vessel(s) 310 are supplying the hydrogen fuel energy source to first energy source supply subsystem output mechanism 312. For example, in many embodiments, thermal management system 308 can be in thermal communication with holding storage vessel(s) 310.

In implementation, thermal management system 308 can comprise any suitable device or devices configured to thermally manage (e.g., cool) at least part of first energy source supply subsystem 301 (e.g., holding storage vessel(s) 310). For example, in some embodiments, thermal management system 308 can comprise one or more heat sinks, one or more thermoelectric coolers, one or more forced air devices (e.g., one or more fans), etc.

In some embodiments, such as, for example, when energy source supply system 300 is similar or identical to appliance energy source supply system 114 (FIG. 1), second energy source supply subsystem 302 can be similar or identical to second appliance energy source supply subsystem 116 (FIG. 1), and vice versa. In other embodiments, such as, for example, when energy source supply system 300 is similar or identical to hub energy source supply system 118 (FIG. 1), second energy source supply subsystem 302 can be similar or identical to second hub energy source supply subsystem 120 (FIG. 1), and vice versa.

For example, in many embodiments, second energy source supply subsystem 302 can be configured to make available a second energy source to receiver vehicle 320 and/or energy source supply appliance 305. Further, the second energy source can comprise an electrical energy source (i.e., electricity). In many embodiments, receiver vehicle 320 can be similar or identical to one of receiver vehicle(s) 109 of FIG. 1 (e.g., receiver vehicle 111 (FIG. 1)). In some embodiments, second appliance energy source supply subsystem 302 can make available the second energy source to receiver vehicle 320 and/or energy source supply appliance 305 when first appliance energy source supply subsystem 301 is making available the first energy source to receiver vehicle 304 and/or energy source supply appliance 305, and vice versa.

In these or other embodiments, second energy source supply subsystem 302 can comprise second energy source supply subsystem input mechanism 314, fuel cell system 315, electric power converter 323, electrical energy storage system 316, electric power converter 317, output control system 319, second energy source supply subsystem output mechanism 318, and/or thermal management system 308. In some embodiments, electrical energy storage system 316, electric power converter 317, and/or thermal management system 308 can be omitted.

In many embodiments, second energy source supply subsystem input mechanism 314 can be configured to receive the hydrogen fuel energy source from first energy source supply subsystem output mechanism 312. Accordingly, in some embodiments, second energy source supply subsystem input mechanism 314 can be coupled (e.g., directly coupled) to first energy source supply subsystem output mechanism 312 in order to receive the hydrogen fuel energy source, such as, for example, by one or more conduits.

In implementation, second energy source supply subsystem input mechanism 314 can comprise one or more receptacles (e.g., one or more fittings) suitable to receive the hydrogen fuel energy source from first energy source supply subsystem output mechanism 312.

In many embodiments, fuel cell system 315 can be configured to receive the hydrogen fuel energy source from second energy source supply subsystem input mechanism 314 and to convert (e.g., electrochemically convert) the hydrogen fuel energy source to the electrical energy source (i.e., electricity). Accordingly, fuel cell system 315 can be coupled (e.g., directly coupled) to second energy source supply subsystem input mechanism 314 in order to receive the hydrogen fuel energy source, such as, for example, by one or more conduits.

In implementation, fuel cell system 315 can comprise one or more fuel cells. The fuel cell(s) can be configured to convert (e.g., electrochemically convert) the hydrogen fuel energy source to the electrical energy source (i.e., electricity). In many embodiments, the fuel cell(s) can comprise one or more fuel cells suitable for converting (e.g., electrochemically converting) the hydrogen fuel energy source to the electrical energy source (i.e., electricity). For example, in some embodiments, the fuel cell(s) can comprise one or more proton exchange membrane fuel cells or one or more solid oxide fuel cells. Further, in some embodiments, the fuel cell(s) can comprise, collectively, a fuel cell power output of greater than or equal to approximately 30 kilowatts and less than or equal to approximately 60 kilowatts.

Further, fuel cell system 315 can comprise a fuel cell input regulator, a fuel cell controller, and/or a fuel cell system packaging. In these or other embodiments, the fuel cell input regulator can control how much of the hydrogen fuel energy source is received by the fuel cell(s) from second energy source supply subsystem input mechanism 314, and the fuel cell controller can control the output voltage of the fuel cell(s). For example, in some embodiments, the fuel cell input regulator can comprise a regulator valve. Further, the fuel cell controller can comprise a microcontroller configured to monitor and control one or more conditions (e.g., humidity, temperature, etc.) of the fuel cell(s). Further still, fuel cell system packaging can comprise any suitable enclosure configured to protect fuel cell system 315 and/or to aid in thermally managing fuel cell system 315. In some embodiments, one or more of the fuel cell input regulator, the fuel cell controller, and/or the fuel cell system packaging can be omitted.

In many embodiments, electric power converter 323 can be configured to receive the electrical energy source (i.e., electricity) from fuel cell system 315 and to convert a voltage of the electrical energy source. Accordingly, in some embodiments, fuel cell system 315 can be coupled (e.g., directly coupled and/or electrically coupled) to electric power converter 323 in order for electric power converter 323 to receive the electrical energy source (i.e., electricity).

In implementation, electric power converter 323 can comprise a direct current to direct current converter (e.g., a voltage regulator). Further, electric power converter 323 can comprise an electric power converter packaging. The electrical power converter packaging can comprise any suitable enclosure configured to protect electric power converter 323 and/or to aid in thermally managing electric power converter 323.

In many embodiments, electrical energy storage system 316 can be configured to receive the electrical energy source (i.e., electricity) from electric power converter 323 and to store the electrical energy source. Accordingly, in some embodiments, when electrical energy storage system 316 is implemented, electrical energy storage system 316 can be coupled (e.g., directly coupled and/or electrically coupled) to electric power converter 323 in order to receive the electrical energy source (i.e., electricity).

In implementation, electrical energy storage system 316 can comprise one or more electrochemical cells. The electrochemical cell(s) can be configured to receive the electrical energy source (i.e., electricity) and to store the electrical energy source. For example, in some embodiments, the electrochemical cell(s) can comprise one or more lithium-ion electrochemical calls. Further, in some embodiments, the electrochemical cell(s) can comprise, collectively, an electrochemical cell power output of greater than or equal to approximately 50 kilowatts and less than or equal to approximately 100 kilowatts.

Further, electrical energy storage system 316 can comprise a cell framework and electrical backbone, a battery management system, and an electrical energy storage system packaging the cell framework and electrical backbone can comprise an electrical network configured to electrically couple together the electrochemical cell(s) and the battery management system. Further, the battery management system can comprise a microcontroller configured to monitor and control the electrochemical cell(s). Further still, the electrical energy storage system packaging can comprise any suitable enclosure configured to protect electrical energy storage system 316 and/or to aid in thermally managing electrical energy storage system 316. In some embodiments, one or more of the cell framework and electrical backbone, the battery management system, and the electrical energy storage system packaging the cell framework and electrical backbone can be omitted.

In many embodiments, electric power converter 317 can be configured to receive the electrical energy source (i.e., electricity) from electrical energy storage system 316 and to convert a voltage and/or type of current of the electrical energy source (i.e., electricity). Accordingly, in some embodiments, when electric power converter 317 is implemented, electric power converter 317 can be coupled (e.g., directly coupled and/or electrically coupled) to electrical energy storage system 316 in order to receive the electrical energy source (i.e., electricity).

In implementation, electric power converter 317 can comprise a direct current to alternating current converter (e.g., a power inverter). In these or other embodiments, electric power converter 317 can comprise a direct current to direct current converter (e.g., a voltage regulator). Further, in these or other embodiments, electric power converter 317 can be configured to operate over a range of greater than or equal to approximately 48 volts and less than or equal to approximately 480 volts. Further, electric power converter 317 can comprise an electric power converter packaging. The electrical power converter packaging can comprise any suitable enclosure configured to protect electric power converter 317 and/or to aid in thermally managing electric power converter 317.

In many embodiments, output control system 319 can be configured to receive the electrical energy source (i.e., electricity) from one of electric power converter 323, electrical energy storage system 316, or electric power converter 317 and to condition or produce the electrical energy source (i.e., electricity) to comply with the electric charging protocol applying to receiver vehicle 320 and/or energy source supply appliance 305. Accordingly, in some embodiments, when electric power converter 317 is implemented, output control system 319 can be coupled (e.g., directly coupled and/or electrically coupled) to electric power converter 317. In other embodiments, when electrical energy storage system 316 is implemented and electric power converter 317 is omitted, output control system 319 can be coupled (e.g., directly coupled and/or electrically coupled) to electrical energy storage system 316. In still other embodiments, when electrical energy storage system 316 and electrical power converter 317 are omitted, output control system 319 can be coupled (e.g., directly coupled and/or electrically coupled) to electric power converter 323.

In implementation, output control system 319 can comprise a battery electric vehicle charging system.

In many embodiments, second energy source supply subsystem output mechanism 318 can be configured to receive the electrical energy source (i.e., electricity) from output control system 319 and to make available the electrical energy source to receiver vehicle 320 and/or energy source supply appliance 305. Accordingly, in some embodiments, second energy source supply subsystem output mechanism 318 can be coupled (e.g., directly coupled and/or electrically coupled) to output control system 319.

In implementation, second energy source supply subsystem output mechanism 318 can comprise one or more electrical connectors suitable to receive the electrical energy source (i.e., electricity) and to make available the electrical energy source to receiver vehicle 320 and/or energy source supply appliance 305. In some embodiments, the electrical connector(s) can comprise one or more electrical lines configured to convey the electrical energy source (i.e., electricity) to electrical energy source to receiver vehicle 320 and/or energy source supply appliance 305. In these or other embodiments, the electrical connector(s) can comprise one or more data lines configured to transfer data between energy source supply system 300 and receiver vehicle 320 and/or energy source supply appliance 305. In many embodiments, the electrical connector(s) can be configured to operate according to any suitable charging protocol or charging protocols. For example, exemplary charging protocols can include the J1772 charging protocol established by the Society of Automotive Engineers of Warrendale, Pennsylvania, United States of America, the CHAdeMO charging protocol established by the CHAdeMO Association of Paris, France, the Tesla charging protocol established by Tesla, Inc. of Palo Alto, California, United States of America, etc.

In some embodiments, when the electrical connector(s) comprise multiple electrical connectors, two or more of the multiple electrical connectors can be configured with the same charging protocols. In these or other embodiments, when the electrical connector(s) comprise multiple electrical connectors, two or more of the multiple electrical connectors can be configured with different charging protocols. In further embodiments, when the electrical connector(s) comprise multiple electrical connectors, and when two or more of the multiple electrical connectors are configured with different charging protocols, output control system 319 can adaptively condition or produce the electrical energy source (i.e., electricity) to comply with the different charging protocols, as needed.

In many embodiments, thermal management system 308 can be configured to thermally manage (e.g., cool) at least part of second energy source supply subsystem 302 (e.g., fuel cell system 315, electric power converter 323, electrical energy storage system 316, electric power converter 317, and/or output control system 319). Thermally managing second energy source supply subsystem 302 (e.g., fuel cell system 315, electric power converter 323, electrical energy storage system 316, electric power converter 317, and/or output control system 319) can improve an operating efficiency of second energy source supply subsystem 302 (e.g., fuel cell system 315, electrical energy storage system 316, electric power converter 317, and/or output control system 319). Further, thermally managing electric power converter 317 can advantageously help to dissipate heat generated by operating electric power converter 317 over a wide operating voltage range. For example, in many embodiments, thermal management system 308 can be in thermal communication with fuel cell system 315, electric power converter 323, electrical energy storage system 316, electric power converter 317, and/or output control system 319.

In implementation, thermal management system 308 can comprise any suitable device or devices configured to thermally manage (e.g., cool) at least part of second energy source supply subsystem 302 (e.g., fuel cell system 315, electric power converter 323, electrical energy storage system 316, electric power converter 317, and/or output control system 319). For example, in some embodiments, thermal management system 308 can comprise one or more heat sinks, one or more thermoelectric coolers, one or more forced air devices (e.g., one or more fans), etc.

In some embodiments, implementing fuel cell system 315 and electrical energy storage system 316 can permit second energy source supply subsystem 302 to make available the electrical energy source (i.e., electricity) to receiver vehicle 320 and/or energy source supply appliance 305 in a direct current to direct current fast charging mode that can approximately fully charge one or more rechargeable energy storage systems of a receiver vehicle drive system of receiver vehicle 320 and/or one or more rechargeable energy storage systems of an appliance energy source supply system of energy source supply appliance 305 in less than or equal to approximately 5 or 10 minutes.

In these or other embodiments, fuel cell system 315 advantageously can be configured to operate in a load-following manner such that fuel cell system 315 can convert the hydrogen fuel energy source to the electrical energy source (i.e., electricity) on an as-needed basis. For example, being able to operate fuel cell system 315 in a load-following manner can be advantageous because energy source supply system 300 can store more energy in the form of the hydrogen fuel energy source rather than in the form of the electrical energy source (i.e., electricity). As a result, degradation of the electrochemical cell(s) of electrical energy storage system 316 can be minimized. Also, in some embodiments, being able to operate fuel cell system 315 in a load-following manner can be advantageous because fuel cell system 315 can be operated to maximize a speed with which the electrical energy source (i.e., electricity) is provided by second energy source supply subsystem 302 to receiver vehicle 320 and/or energy source supply appliance 305. Although, in some embodiments, operating fuel cell system 315 in a load-following manner can degrade the service life of fuel cell system 315, the wear on fuel cell system 315 can be offset by cooling fuel cell system 315 and avoiding fast activation sequences, such as, for example, by implementing predictive command algorithms which avoid fast changes (e.g., gas line pressurizations, sensor resets, flow control, etc.) to the balance of plant of the fuel cell system 315.

Further, by implementing electric power converter 323, a quantity and/or electric power capacity of the fuel cell(s) of fuel cell system 315 advantageously can be scaled up or down, as desired. For example, a quantity and/or electric power capacity of the fuel cell(s) of fuel cell system 315 can be scaled up or down, such as, for example, to provide a desired electric power output of fuel cell system 315, because electric power converter 323 can adjust the voltage of the electric energy source (i.e., electricity), as needed. Also, because electric power converter 323 can adjust the voltage of the electric energy source (i.e., electricity), as needed, the fuel cell(s) of fuel cell system 315 can be implemented with off-the-shelf fuel cell(s). Implementing the fuel cell(s) of fuel cell system 315 with off-the-shelf fuel cell(s) advantageously can permit specifications of the fuel cell(s) of fuel cell system 315 to be known without further testing by the operator of system 300.

Further, by implementing electric power converter 317 and/or output control system 319, second energy source supply subsystem output mechanism 318 can advantageously make available the electrical energy source (i.e., electricity) to receiver vehicle 320 and/or energy source supply appliance 305 with multiple charging modes (e.g., one or more of Modes 1-4 established by the International Electrotechnical Commission of London, England, United Kingdom, direct current to direct current fast charging, etc.) and/or with multiple charging protocols. Meanwhile, implementing electric power converter 317 to comprise a direct current to direct current converter can be advantageous to eliminate a need to rectify the electrical energy source (i.e., electricity) being provided to receiver vehicle 320 and/or energy source supply appliance 305.

In many embodiments, SDT subsystem 303 can be configured to log performance data of energy source supply system 300. In these or other embodiments, SDT subsystem 303 can be configured to monitor energy source supply system 300 (e.g., first energy source supply subsystem 301 and/or second energy source supply subsystem 302) and diagnose problems affecting energy source supply system 300 (e.g., first energy source supply subsystem 301 and/or second energy source supply subsystem 302). For example, in some embodiments, SDT subsystem 303 can compare measured parameters (e.g., voltage, current, pressure, temperature, etc.) applying to energy source supply system 300 (e.g., first energy source supply subsystem 301 and/or second energy source supply subsystem 302) to predetermined boundary conditions to determine if the measured parameters are outside of the boundary conditions (e.g., over/under voltage, over/under current, over/under pressure, over/under temperature, etc.) or are trending toward an out-of-bounds condition. Based on the severity of the out-of-bounds condition and/or the criticality of the affected portion or portions of energy source supply system 300 (e.g., first energy source supply subsystem 301 and/or second energy source supply subsystem 302) can identify an out-of-bounds condition as being non-impactful, as requiring attention within a designated time frame (i.e., an alert condition), as requiring immediate attention (i.e., an alarm condition), or as being a system failure. In many embodiments, SDT subsystem 303 can deactivate energy source supply system 300 (e.g., first energy source supply subsystem 301 and/or second energy source supply subsystem 302) or the affected portion or portions of energy source supply system 300 (e.g., first energy source supply subsystem 301 and/or second energy source supply subsystem 302) in the event of an alarm condition or system failure.

In implementation, SDT subsystem 303 can comprise one or more sensors configured to measure one or more parameters (e.g., voltage, current, pressure, temperature, etc.) applying to energy source supply system 300 (e.g., first energy source supply subsystem 301 and/or second energy source supply subsystem 302). Further, SDT subsystem 303 can comprise one or more microcontrollers configured to log performance data of energy source supply system 300 and/or to analyze the one or more parameters measured by the sensor(s) and compare the parameters to the predetermined boundary conditions. Further still, SDT subsystem 303 can comprise one or more safety devices configured to prevent propagation and/or amplification of failures in energy source supply system 300 (e.g., first energy source supply subsystem 301 and/or second energy source supply subsystem 302). Exemplary safety device(s) can include fuses, circuit breakers, stop valves, blow-off valves, etc. In these embodiments, SDT subsystem 303 (e.g., the microcontroller(s) of SDT subsystem 303) can activate one or more of the safety device(s) of SDT subsystem 303 to prevent propagation and/or amplification of failures in energy source supply system 300, such as, for example, in response to one or more parameters measured by the sensor(s) of SDT subsystem 303 and/or analyzed by the microcontroller(s) of SDT subsystem 303. Further, in some embodiments, in determining when to activate one or more of the safety device(s) of SDT subsystem 303, SDT subsystem 303 (e.g., the microcontroller(s) of SDT subsystem 303) can use adaptive logic and/or machine learning to build upon a failure mode effect criticality analysis (FMECA) of energy source supply system 300. For example, the FMECA can be based on one or more look-up tables of potential faults and the associated consequences, severity, and/or probability of the potential faults. In further embodiments, the look-up tables can establish where the sensor(s) and/or safety device(s) of SDT subsystem 303 are located within energy source supply system 300. In some embodiments, SDT subsystem 303 (e.g., the microcontroller(s) of SDT subsystem 303) can confirm the presences of faults using anomaly test logic prior to activating one or more of the safety device(s) of SDT subsystem 303.

In some embodiments, SDT subsystem 303 can be configured to implement a learning logic flow. For example, SDT subsystem 303 can characterize the sensor(s) of SDT subsystem 303, rate the sensor(s) of SDT subsystem 303 for criticality, implement a baseline operation, poll the sensor(s) of SDT subsystem 303 for operational data, compare the operational data to alert and alarm lookup tables, and trigger alert and alarm notifications when operational data is outside accepted tolerances of the alert and alarm lookup tables. Polling frequency and comparisons can be added or modified based on occurrences of the operational data being outside accepted tolerance of the alert and alarm lookup tables.

Figure 22:
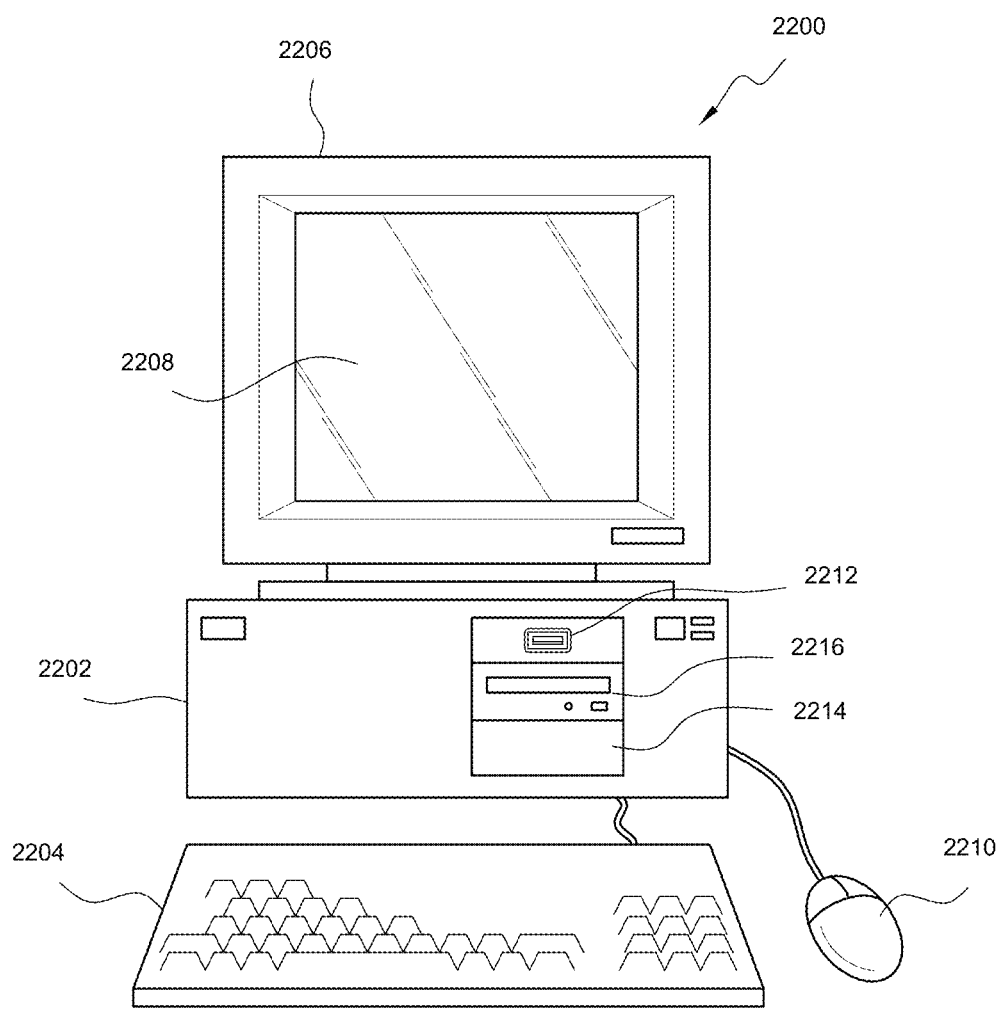
FIG. 22 illustrates a front elevational view of an exemplary computer system that is suitable to implement at least part of a control subsystem of the system of FIG. 3 and/or FIG. 14, or at least part of one or more of the methods described herein.

In many embodiments, control subsystem 324 can be configured to control energy source supply system 300 (e.g., first energy source supply subsystem 301, second energy source supply subsystem 302, SDT subsystem 303, communication subsystem 321, and/or electric power subsystem 325). For example, in many embodiments, control subsystem 324 can comprise a computer system. In some embodiments, the computer system can be similar or identical to computer system 2200 (FIG. 22).

In many embodiments, communication subsystem 321 can be configured to provide communication between first energy source supply subsystem 301, second energy source supply subsystem 302, SDT subsystem 303, control subsystem 324, and/or electric power subsystem 325, and/or within first energy source supply subsystem 301, second energy source supply subsystem 302, SDT subsystem 303, control subsystem 324, and/or electric power subsystem 325. In implementation, communication subsystem 321 can comprise a control area network vehicle bus (CAN bus).

In some embodiments, communication subsystem 321 can accept cellular network communication (via a cellular network transponder), which may include deployment directions for energy source supply system 300. In some embodiments, deployment directions for energy source supply system 300 can be provided based on a location of receiver vehicle 304 and/or receiver vehicle 320, and/or a time to on-site energy transfer (service) calculation. The location and timing information can be relayed by communication subsystem 321 to control subsystem 324 to initiate a system readiness polling of SDT subsystem 303 and electric power subsystem 325. Based on confirmation of acceptable polling results (e.g., functionality and safety checklist), control subsystem 324 can instruct second energy source supply subsystem 302 to initiate preparatory actions necessary to transfer energy to receiver vehicle 304 and/or receiver vehicle 320 within the timeframe of the expected arrival at location or locations of receiver vehicle 304 and/or receiver vehicle 320. Based on confirmation of acceptable polling results control subsystem 324 also can instruct thermal management subsystem 308 to initiate a pre-cool down procedure of second energy source supply subsystem 302. Implementing a pre-cool down procedure can avoid thermal and mechanical stresses to equipment, thereby increasing equipment life, decreasing a probability of thermal related failure modes/safety events, and/or more efficiently applying on-platform cooling potential energy, such as, for example, by avoiding steady state environmental temperature maintenance. In some embodiments, the pre-cool down procedure can be implemented without using energy from second energy source supply subsystem 302, and/or with minimum propagation delay because it can be performed with solid state thermal management.

In many embodiments, electric power subsystem 325 can be configured to electrically power one or more (e.g., all) electrical components of energy source supply system 300, first energy source supply subsystem 301, second energy source supply subsystem 302, SDT subsystem 303, control subsystem 324, and/or communication subsystem 321. Accordingly, in these embodiments, electric power subsystem 325 can be coupled (e.g., electrically coupled) to any electrical components of energy source supply system 300, first energy source supply subsystem 301, second energy source supply subsystem 302, SDT subsystem 303, control subsystem 324, and/or communication subsystem 321 that electric power subsystem 325 is configured to electrically power.

In implementation, electric power subsystem 325 can comprise one or more rechargeable energy storage systems. For example, in these embodiments, the rechargeable energy storage system(s) can store an electrical energy source (i.e., electricity) and make available the electrical energy source to one or more (e.g., all) electrical components of energy source supply system 300, first energy source supply subsystem 301, second energy source supply subsystem 302, SDT subsystem 303, control subsystem 324, and/or communication subsystem 321. Further, in these embodiments, the rechargeable energy storage system(s) can comprise (a) one or more electrochemical cells (e.g., one or more batteries), (b) one or more capacitive energy storage systems (e.g., super capacitors such as electric double-layer capacitors), and/or (c) one or more inertial energy storage systems (e.g., one or more flywheels).

Further, electric power subsystem 325 can comprise a battery charger. The battery charger can be configured to receive an electrical energy source (i.e., electricity), such as, for example, from a utility electric grid, and to make available the electrical energy source to the rechargeable energy storage system(s) of electric power subsystem 325. In some embodiments, the battery charger also can be configured to make available the electrical energy source to electrical energy storage system 316. In some embodiments, fuel cell system 315 can make available the electrical energy source (i.e., electricity) generated by fuel cell system 315 to the rechargeable energy storage system(s) of electric power subsystem 325.

In many embodiments, thermal management system 308 can be configured to thermally manage (e.g., cool) at least part of electric power subsystem 325. Thermally managing electric power subsystem 325 can improve an operating efficiency of electric power subsystem 325. For example, in many embodiments, thermal management system 308 can be in thermal communication with electric power subsystem 325.

In these or other embodiments, electrical energy storage system 316 can be configured to electrically power one or more (e.g., all) electrical components of energy source supply system 300, first energy source supply subsystem 301, second energy source supply subsystem 302, SDT subsystem 303, control subsystem 324, and/or communication subsystem 321. Accordingly, in these embodiments, electrical energy storage system 316 can be coupled (e.g., electrically coupled) to any electrical components of energy source supply system 300, first energy source supply subsystem 301, second energy source supply subsystem 302, SDT subsystem 303, control subsystem 324, and/or communication subsystem 321 that electrical energy storage system 316 is configured to electrically power.

In some embodiments, thermal management system 308 can comprise a reservoir of coolant, a distribution circuit configured to deliver the coolant to the part or parts of energy source supply system 300 that thermal management system 308 is thermally managing, a heat exchanger subsystem to accept and vent heat transferred to the coolant by the part or parts of energy source supply system 300 that thermal management system 308 is thermally managing, a coolant distribution controller configured to control distribution of the coolant through the distribution circuit, distributed temperature sensors to provide temperature data to the coolant distribution controller about the part or parts of energy source supply system 300 that thermal management system 308 is thermally managing, and end cooling plates configured to put the coolant in thermal contact with any part or parts of energy source supply system 300 that thermal management system 308 is thermally managing.

In many embodiments, one or more of the elements of energy source supply system 300 can be positioned to minimize thermal and/or electromagnetic interference at energy source supply system 300. Positioning of one or more elements of energy source supply system 300 can be determined in view of a volume available to house the elements of energy source supply system 300, a shared thermal stress of the elements of energy source supply system 300, and/or a risk of electromagnetically induced cross talk or interference. In some embodiments, one or more of the elements of energy source supply system 300 can be positioned such that high power electrical pathways are separate from data, sensor, and low voltage electrical signals. In further embodiments, coolant for thermal management system 308 can be separately routed to maximize volume for modular expansion of energy source supply system 300. In many embodiments, separating high power electrical pathways from data, sensor, and low voltage electrical signals and/or separately routing coolant for thermal management system 308 can permit optimal access to the elements of energy source supply system 300 for repair and maintenance of energy source supply system 300. In some embodiments, one or more of the elements of energy source supply system 300 can be positioned to support a directional flow of heat generated by energy source supply system 300 rather than unidirectional heat radiation, and to minimize the formation of hot spots in energy source supply system 300. In further embodiments, one or more elements of energy source supply system 300 can be positioned to permit modularity of one or more elements of energy source supply system 300.

Although energy source supply system 300 is generally described for embodiments where the first energy source comprises a hydrogen fuel energy source, in some embodiments, first energy source can comprise another fuel energy source, such as, for example, a natural gas fuel energy source. In these embodiments, for example, fuel cell system 315 can be implemented with solid oxide fuel cells. Further, in some of these embodiments, holding storage vessel(s) 310 can act as a heat sink for fuel cell system 315.

Figure 4:
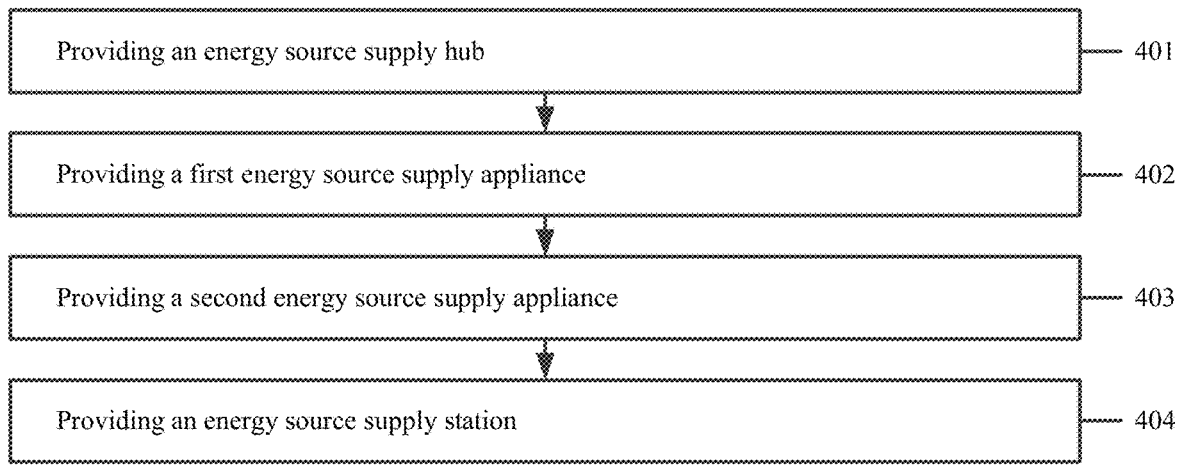
FIG. 4 illustrates a flow chart for an embodiment of a method of providing (e.g., manufacturing) a system.

Turning ahead in the drawings, FIG. 4 illustrates a flow chart for an embodiment of method 400 of providing (e.g., manufacturing) a system. Method 400 is merely exemplary and is not limited to the embodiments presented herein. Method 400 can be employed in many different embodiments or examples not specifically depicted or described herein. In some embodiments, the procedures, the activities of method 400 can be performed in the order presented. In other embodiments, the procedures, the activities of the method 400 can be performed in any other suitable order. In still other embodiments, one or more of the activities in method 400 can be combined or skipped. In many embodiments, the system can be similar or identical to system 100 (FIG. 1).

Figure 5:
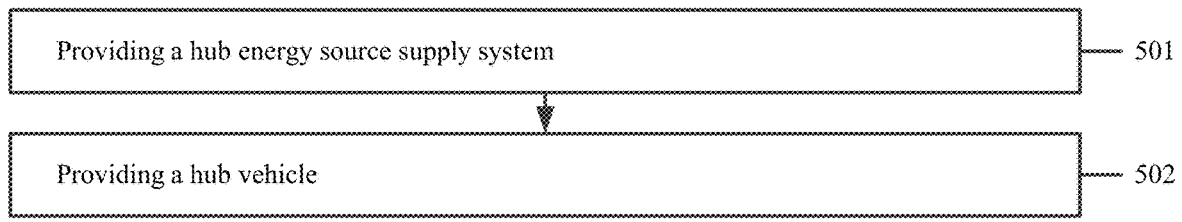
FIG. 5 illustrates an exemplary activity of providing an energy source supply hub, according to the embodiment of FIG. 4.

In many embodiments, method 400 can comprise activity 401 of providing an energy source supply hub. In some embodiments, the energy source supply hub can be similar or identical to one of energy source supply hub(s) 105 of FIG. 1 (e.g., energy source supply hub 106 (FIG. 1)). FIG. 5 illustrates an exemplary activity 401, according to the embodiment of FIG. 4.

Figure 6:
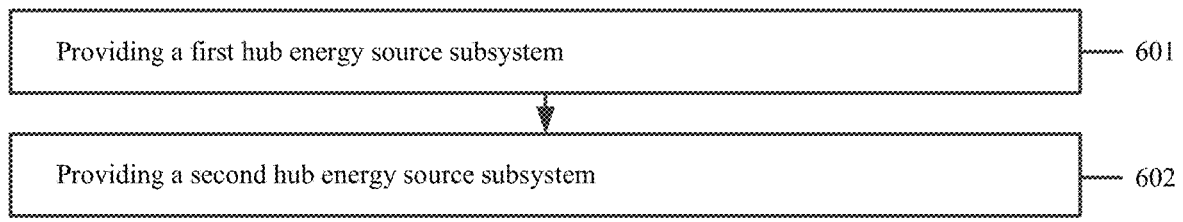
FIG. 6 illustrates an exemplary activity of providing a hub energy source supply system, according to the embodiment of FIG. 4.

For example, in many embodiments, activity 401 can comprise activity 501 of providing a hub energy source supply system. In some embodiments, the hub energy source supply system can be similar or identical to hub energy source supply system 118 (FIG. 1) and/or energy source supply system 300 (FIG. 3). FIG. 6 illustrates an exemplary activity 501, according to the embodiment of FIG. 4.

For example, in many embodiments, activity 501 can comprise activity 601 of providing a first hub energy source supply subsystem. In some embodiments, the first hub energy source supply subsystem can be similar or identical to first hub energy source supply subsystem 119 (FIG. 1) and/or first energy source supply subsystem 301 (FIG. 3).

In further embodiments, activity 501 can comprise activity 602 of providing a second hub energy source supply subsystem. In some embodiments, the second hub energy source supply subsystem can be similar or identical to second hub energy source supply subsystem 120 (FIG. 1) and/or second energy source supply subsystem 302 (FIG. 3). In other embodiments, activity 602 can be omitted.

Turning again to FIG. 5, in some embodiments, activity 401 can comprise activity 502 of providing a hub vehicle. In some embodiments, the hub vehicle can be similar or identical to hub vehicle 121 (FIG. 1). In other embodiments, activity 502 can be omitted.

Figure 7:
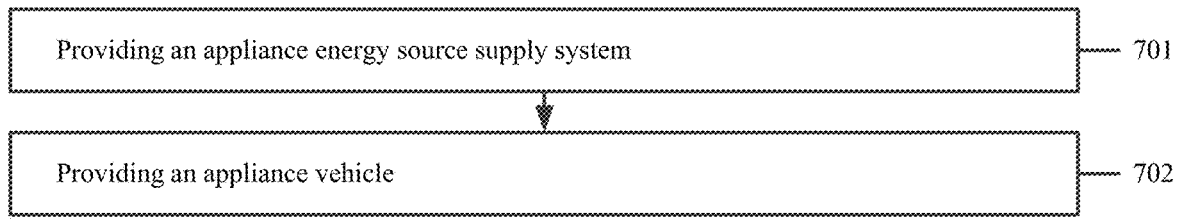
FIG. 7 illustrates an exemplary activity of providing a first energy source supply appliance, according to the embodiment of FIG. 4.

Turning now back to FIG. 4, in many embodiments, method 400 can comprise activity 402 of providing a first energy source supply appliance. In some embodiments, the first energy source supply appliance can be similar or identical to one of energy source supply appliance(s) 102 of FIG. 1 (e.g., energy source supply appliance 103 (FIG. 1) and/or energy source supply appliance 104 (FIG. 1)). In some embodiments, one of activity 401 or activity 402 can be omitted. FIG. 7 illustrates an exemplary activity 402, according to the embodiment of FIG. 4.

Figure 8:
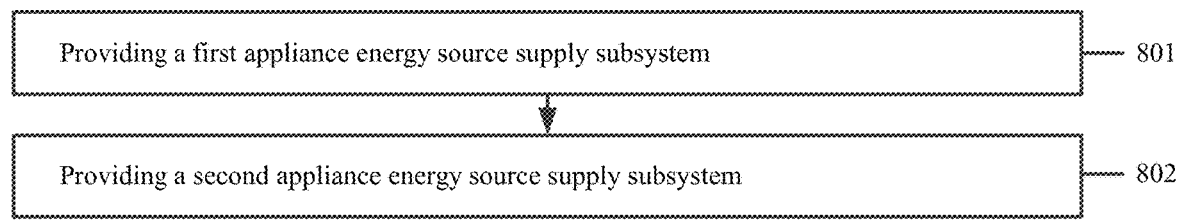
FIG. 8 illustrates an exemplary activity of providing an appliance energy source supply system, according to the embodiment of FIG. 4.

For example, in many embodiments, activity 402 can comprise activity 701 of providing an appliance energy source supply system. In some embodiments, the appliance energy source supply system can be similar or identical to appliance energy source supply system 114 (FIG. 1) and/or energy source supply system 300 (FIG. 3). FIG. 8 illustrates an exemplary activity 701, according to the embodiment of FIG. 4.

For example, in many embodiments, activity 701 can comprise activity 801 of providing a first appliance energy source supply subsystem. In some embodiments, the first appliance energy source supply subsystem can be similar or identical to first appliance energy source supply subsystem 115 (FIG. 1) and/or first energy source supply subsystem 301 (FIG. 3).

In further embodiments, activity 701 can comprise activity 802 of providing a second appliance energy source supply subsystem. In some embodiments, the second appliance energy source supply subsystem can be similar or identical to second appliance energy source supply subsystem 116 (FIG. 1) and/or second energy source supply subsystem 302 (FIG. 3). In other embodiments, activity 802 can be omitted.

Turning again to FIG. 7, in some embodiments, activity 402 can comprise activity 702 of providing an appliance vehicle. In some embodiments, the appliance vehicle can be similar or identical to appliance vehicle 117 (FIG. 1). In other embodiments, activity 702 can be omitted.

Turning now back to FIG. 4, in many embodiments, method 400 can comprise activity 403 of providing a second energy source supply appliance. In some embodiments, the second energy source supply appliance can be similar or identical to the first energy source supply appliance, one of energy source supply appliance(s) 102 of FIG. 1 (e.g., energy source supply appliance 103 (FIG. 1) and/or energy source supply appliance 104 (FIG. 1)). Further, in many embodiments, performing activity 403 can be similar or identical to performing activity 402. In some embodiments, activity 403 can be omitted.

In some embodiments, method 400 can comprise activity 404 of providing an energy source supply station. In some embodiments, the second energy source supply station can be similar or identical to one of energy source supply station(s) 107 of FIG. 1 (e.g., energy source supply station 108 (FIG. 1)). In other embodiments, activity 404 can be omitted.

Figure 9:
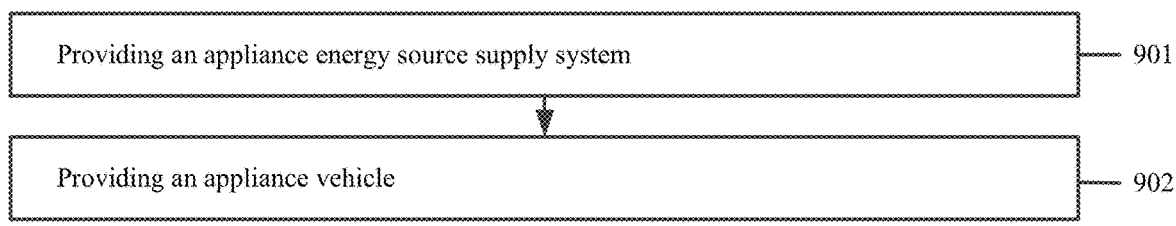
FIG. 9 illustrates a flow chart for an embodiment of a method of providing (e.g., manufacturing) an energy source supply device.

Turning ahead in the drawings, FIG. 9 illustrates a flow chart for an embodiment of method 900 of providing (e.g., manufacturing) an energy source supply device. Method 900 is merely exemplary and is not limited to the embodiments presented herein. Method 900 can be employed in many different embodiments or examples not specifically depicted or described herein. In some embodiments, the activities of method 900 can be performed in the order presented. In other embodiments, the activities of the method 900 can be performed in any other suitable order. In still other embodiments, one or more of the activities in method 900 can be combined or skipped. In many embodiments, the energy source supply device can be similar or identical to one of energy source supply device(s) 101 of FIG. 1 (e.g., one of energy source supply hub(s) 105 (FIG. 1) and/or one of energy source supply appliance(s) 102 (FIG. 1)).

Figure 10:
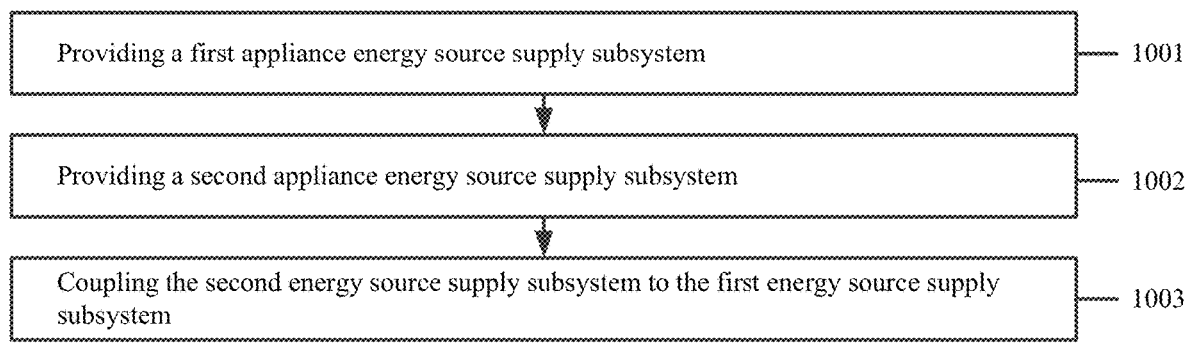
FIG. 10 illustrates an exemplary activity of providing an appliance energy source supply system, according to the embodiment of FIG. 9.

In many embodiments, method 900 can comprise activity 901 of providing an appliance energy source supply system. In many embodiments, the appliance energy source supply system can be similar or identical to appliance energy source supply system 114 (FIG. 1) and/or energy source supply system 300 (FIG. 3). FIG. 10 illustrates an exemplary activity 901, according to the embodiment of FIG. 9.

For example, in many embodiments, activity 901 can comprise activity 1001 of providing a first appliance energy source supply subsystem. In some embodiments, the first appliance energy source supply subsystem can be similar or identical first appliance energy source supply subsystem 115 (FIG. 1) and/or first energy source supply subsystem 301 (FIG. 3).

Figure 11:
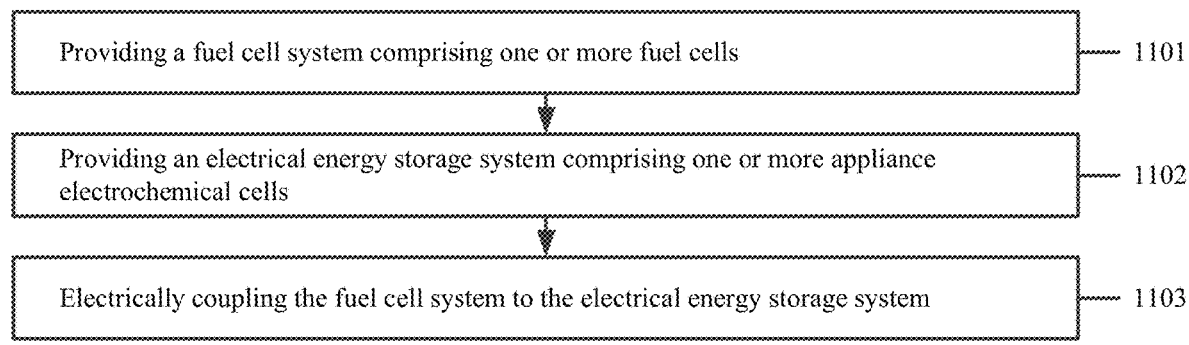
FIG. 11 illustrates an exemplary activity of providing a second appliance energy source supply subsystem, according to the embodiment of FIG. 9.

Further, in some embodiment, activity 901 can comprise activity 1002 of providing a second appliance energy source supply subsystem. In some embodiments, the second appliance energy source supply subsystem can be similar or identical second appliance energy source supply subsystem 116 (FIG. 1) and/or second energy source supply subsystem 302 (FIG. 3). In other embodiments, the second appliance energy source supply subsystem can be omitted. FIG. 11 illustrates an exemplary activity 1002, according to the embodiment of FIG. 10.

For example, in many embodiments, activity 1002 can comprise activity 1101 of providing a fuel cell system comprising one or more fuel cells. In some embodiments, the fuel cell system can be similar or identical to fuel cell system 315 (FIG. 3).

In many embodiments, activity 1002 can comprise activity 1102 of providing an electrical energy storage system comprising one or more appliance electrochemical cells. In some embodiments, the electrical energy storage system can be similar or identical to electrical energy storage system 316 (FIG. 3).

In many embodiments, activity 1002 can comprise activity 1103 of electrically coupling the fuel cell system to the electrical energy storage system. In some embodiments, performing activity 1103 can be similar or identical to electrically coupling the fuel cell system 315 (FIG. 3) to electrical energy storage system 316 (FIG. 3).

Referring back to FIG. 10, in many embodiments, activity 901 can comprise activity 1003 of coupling the second appliance energy source supply subsystem to the first appliance energy source supply subsystem. For example, in some embodiments, performing activity 1003 can be similar or identical to coupling second appliance energy source supply subsystem 302 (FIG. 3) to first appliance energy source supply subsystem 301 (FIG. 3) as described above with respect to energy source supply system 300 (FIG. 3). In other embodiments, activity 1003 can be omitted.

Turning again back to FIG. 9, in many embodiments, method 900 can comprise activity 902 of providing an appliance vehicle. In some embodiments, the appliance vehicle can be similar or identical to appliance vehicle 117 (FIG. 1). In other embodiments, activity 902 can be omitted.

Figure 12:
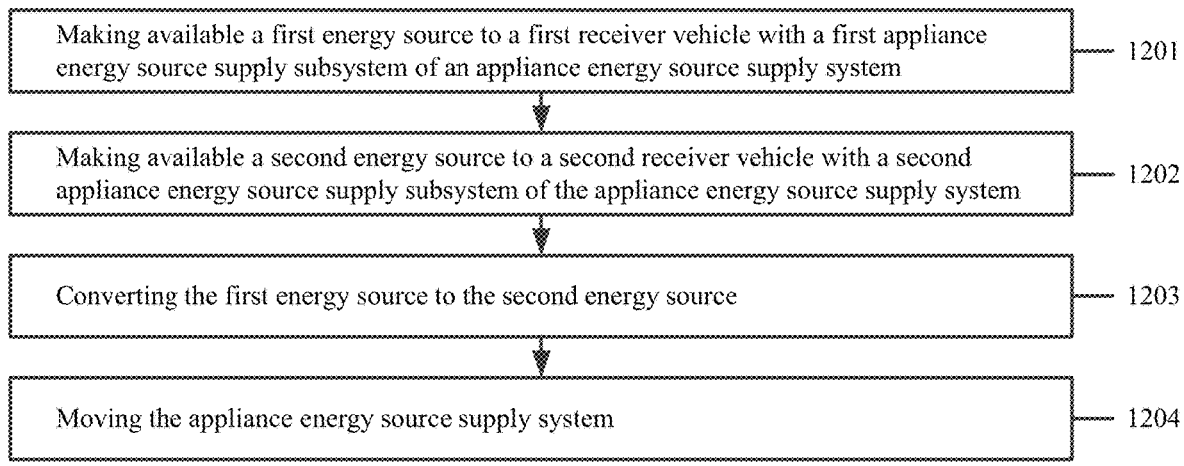
FIG. 12 illustrates a flow chart for an embodiment of a method.

Turning ahead in the drawings, FIG. 12 illustrates a flow chart for an embodiment of method 1200. Method 1200 is merely exemplary and is not limited to the embodiments presented herein. Method 1200 can be employed in many different embodiments or examples not specifically depicted or described herein. In some embodiments, the procedures, the activities of method 1200 can be performed in the order presented. In other embodiments, the procedures, the activities of the method 1200 can be performed in any other suitable order. In still other embodiments, one or more of the activities in method 1200 can be combined or skipped. In many embodiments, method 1200 can comprise a method of using an energy source supply device. In many embodiments, the energy source supply device can be similar or identical to one of energy source supply device(s) 101 of FIG. 1 (e.g., one of energy source supply hub(s) 105 (FIG. 1) and/or one of energy source supply appliance(s) 102 (FIG. 1)).

In many embodiments, method 1200 can comprise activity 1201 of making available a first energy source to a first receiver vehicle with a first appliance energy source supply subsystem of an appliance energy source supply system. In some embodiments, the first receiver vehicle can be similar or identical to one of receiver vehicle(s) 109 of FIG. 1 (e.g., receiver vehicle 110 (FIG. 1) and/or receiver vehicle 111 (FIG. 1)). Further, the first appliance energy source supply subsystem can be similar or identical to first appliance energy source supply subsystem 115 (FIG. 1). Further still, the appliance energy source supply system can be similar or identical to appliance energy source supply system 114 (FIG. 1). In many embodiments, the first energy source can comprise a hydrogen fuel energy source. In some embodiments, activity 1201 can be omitted.

In many embodiments, method 1200 can comprise activity 1202 of making available a second energy source to a second receiver vehicle with a second appliance energy source supply subsystem of the appliance energy source supply system. In some embodiments, the second receiver vehicle can be similar or identical to one of receiver vehicle(s) 109 of FIG. 1 (e.g., receiver vehicle 110 (FIG. 1) and/or receiver vehicle 111 (FIG. 1)). Further, the second appliance energy source supply subsystem can be similar or identical to second appliance energy source supply subsystem 116 (FIG. 1). In many embodiments, activity 1202 can be performed before, after, or simultaneously with activity 1201. In some embodiments, the second energy source can be different than the first energy source. For example, the second energy source can comprise an electrical energy source (i.e., electricity).

When the second energy source comprises an electrical energy source, in some embodiments, performing activity 1202 can comprise an activity of approximately fully charging one or more vehicle electrochemical cells of a second drive system of the second receiver vehicle with the electrical energy source in less than or equal to approximately 5 or 10 minutes. In some embodiments, the second drive system can be similar or identical to receiver vehicle drive system 113 (FIG. 1).

In many embodiments, method 1200 can comprise activity 1203 of converting (e.g., electrochemically converting) the first energy source to the second energy source. In many embodiments, performing activity 1203 can be similar or identical to converting (e.g., electrochemically converting) the first energy source to the second energy source as described above with respect to system 100 (FIG. 1) and/or energy source supply system 300 (FIG. 3). In further embodiments, activity 1203 can be performed before or simultaneously with activity 1202. For example, in some embodiments, performing activity 1203 can comprise an activity of using a fuel cell system to convert (e.g., electrochemically convert) the first energy source to the second energy source. In these embodiments, the fuel cell system can be similar or identical to fuel cell system 315 (FIG. 3).

In many embodiments, method 1200 can comprise activity 1204 of moving the appliance energy source supply system. In some embodiments, performing activity 1204 can be similar or identical to moving the appliance energy source supply system as described above with respect to system 100 (FIG. 1) and/or energy source supply system 300 (FIG. 3). For example, in some embodiments, performing activity 1204 can comprise an activity of moving the appliance energy source supply system with an appliance vehicle. In these embodiments, the appliance vehicle can be similar or identical to appliance vehicle 117 (FIG. 1).

Figure 13:
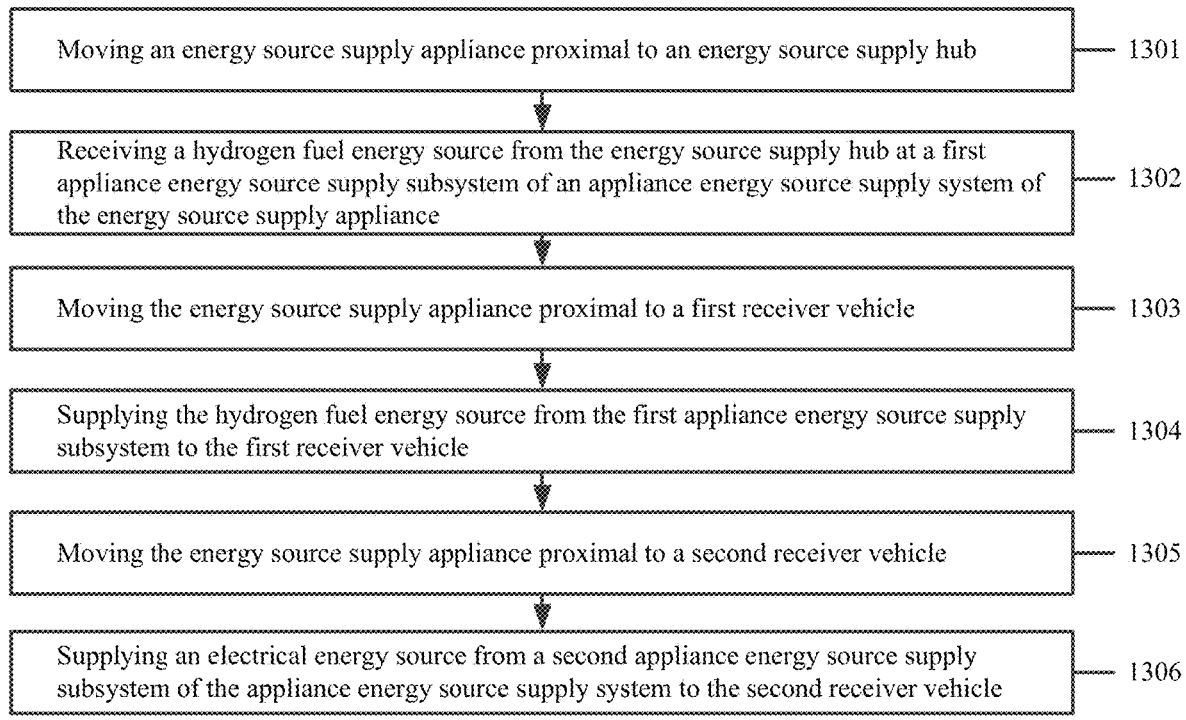
FIG. 13 illustrates a flow chart for an embodiment of a method.

Skipping ahead in the drawings, FIG. 13 illustrates a flow chart for an embodiment of method 1300. Method 1300 is merely exemplary and is not limited to the embodiments presented herein. Method 1300 can be employed in many different embodiments or examples not specifically depicted or described herein. In some embodiments, the procedures, the activities of method 1300 can be performed in the order presented. In other embodiments, the procedures, the activities of the method 1300 can be performed in any other suitable order. In still other embodiments, one or more of the activities in method 1300 can be combined or skipped. In many embodiments, method 1300 can comprise a method of using a system. In some embodiments, the system can be similar or identical to system 100 (FIG. 1).

In many embodiments, method 1300 can comprise activity 1301 of moving an energy source supply appliance proximal to an energy source supply hub. In some embodiments, the energy source supply hub can be similar or identical to energy source supply hub 106 (FIG. 1). In these or other embodiments, the energy source supply appliance can be similar or identical to one of energy source supply appliance(s) 102 of FIG. 1 (e.g., energy source supply appliance 103 and/or energy source supply appliance 104).

In many embodiments, method 1300 can comprise activity 1302 of receiving a hydrogen fuel energy source from the energy source supply hub at a first appliance energy source supply subsystem of an appliance energy source supply system of the energy source supply appliance. In some embodiments, the first appliance energy source supply subsystem can be similar or identical to first appliance energy source supply subsystem 115 (FIG. 1). Further, the appliance energy source supply system can be similar or identical to appliance energy source supply system 114 (FIG. 1). In some embodiments, activity 1302 can be performed after activity 1301.

In many embodiments, method 1300 can comprise activity 1303 of moving the energy source supply appliance proximal to a first receiver vehicle. In some embodiments, the first receiver vehicle can be similar or identical to one of receiver vehicle(s) 109 of FIG. 1 (e.g., receiver vehicle 110 and/or receiver vehicle 111). In further embodiments, activity 1303 can be performed after activity 1302.

In many embodiments, method 1300 can comprise activity 1304 of supplying the hydrogen fuel energy source from the first appliance energy source supply subsystem to the first receiver vehicle. In some embodiments, activity 1304 can be performed after activity 1303. In other embodiments, activity 1303 and/or activity 1304 can be omitted.

In many embodiments, method 1300 can comprise activity 1305 of moving the energy source supply appliance proximal to a second receiver vehicle. In some embodiments, the second receiver vehicle can be similar or identical to one of receiver vehicle(s) 109 of FIG. 1 (e.g., receiver vehicle 110 and/or receiver vehicle 111). In further embodiments, activity 1305 can be performed after one or more of activity 1302, activity 1303, and activity 1304.

In many embodiments, method 1300 can comprise activity 1306 of supplying an electrical energy source from a second appliance energy source supply subsystem of the appliance energy source supply system to the second receiver vehicle. In some embodiments, the second appliance energy source supply subsystem can be similar or identical to second appliance energy source supply subsystem 116 (FIG. 1). In some embodiments, activity 1306 can be performed after activity 1304 and/or activity 1305. In other embodiments, activity 1306 can be performed before or simultaneously with activity 1304. In further embodiments, activity 1305 and/or activity 1306 can be omitted.

Some embodiments of method 1300 can be implemented with a natural gas fuel energy source instead of a hydrogen fuel energy source.

Figure 14:
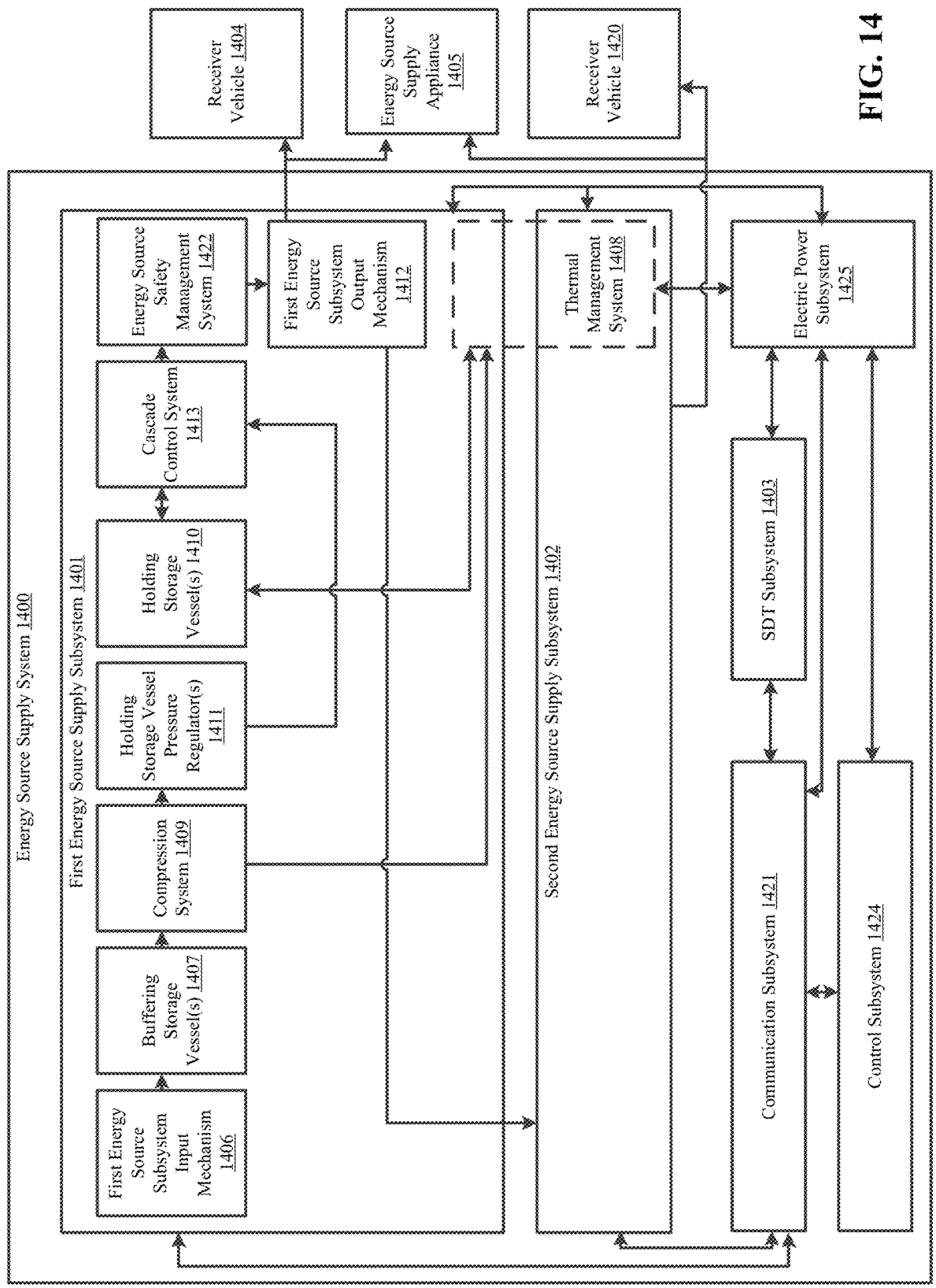
FIG. 14 illustrates an exemplary block diagram for an energy source supply system, according to an embodiment.

Turning ahead in the drawings, FIG. 14 illustrates an exemplary block diagram for energy source supply system 1400, according to an embodiment. Energy source supply system 1400 is merely exemplary and is not limited to the embodiments presented herein. Energy source supply system 1400 can be employed in many different embodiments or examples not specifically depicted or described herein.

In some embodiments, energy source supply system 1400 can be similar or identical to appliance energy source supply system 114 (FIG. 1), and vice versa. Accordingly, in these embodiments, energy source supply system 1400 can be used to implement appliance energy source supply system 114 (FIG. 1) in system 100 (FIG. 1). In other embodiments, energy source supply system 1400 can be similar or identical to hub energy source supply system 118 (FIG. 1), and vice versa. According, in these embodiments, energy source supply system 1400 can be used to implement hub energy source supply system 118 (FIG. 1) in system 100 (FIG. 1).

In these or other embodiments, energy source supply system 1400 can be similar or identical to energy source supply system 300 (FIG. 3), and vice versa. For example, in many embodiments, energy source supply system 1400 can comprise first energy source supply subsystem 1401. In further embodiments, energy source supply system 1400 can comprise second energy source supply subsystem 1402, safety, diagnostic, and telemetry (SDT) subsystem 1403, communication subsystem 1421, control subsystem 1424, and/or electric power subsystem 1425. However, in other embodiments, second energy source supply subsystem 1402, SDT subsystem 1403, communication subsystem 1421, control subsystem 1424, and/or electric power subsystem 1425 can be omitted. Further, in some embodiments, part or all of second energy source supply subsystem 1402 can be part of first energy source supply subsystem 1401, and vice versa.

In some embodiments, such as, for example, when energy source supply system 1400 is similar or identical to appliance energy source supply system 114 (FIG. 1), first energy source supply subsystem 1401 can be similar or identical to first appliance energy source supply subsystem 115 (FIG. 1), and vice versa. In other embodiments, such as, for example, when energy source supply system 1400 is similar or identical to hub energy source supply system 118 (FIG. 1), first energy source supply subsystem 1401 can be similar or identical to first hub energy source supply subsystem 119 (FIG. 1), and vice versa.

For example, in some embodiments, first energy source supply subsystem 1401 can be configured to make available a first energy source to second energy source supply subsystem 1402, receiver vehicle 1404, and/or energy source supply appliance 1405. Further, the first energy source can comprise a hydrogen fuel energy source (e.g., a gaseous or liquid hydrogen fuel energy source), and the second energy source can comprise an electrical energy source. In many embodiments, receiver vehicle 1404 can be similar or identical to one of receiver vehicle(s) 109 of FIG. 1 (e.g., receiver vehicle 110 (FIG. 1)). In these or other embodiments, energy source supply appliance 1405 can be similar or identical to one of energy source supply appliances 102 of FIG. 1 (e.g., energy source supply appliance 103 (FIG. 1) and/or energy source supply appliance 104 (FIG. 1)). In other embodiments, first energy source supply subsystem 1401 can make available the first energy source to second energy source supply subsystem 1402 but not to receiver vehicle 1404 and/or energy source supply appliance 1405.

In these or other embodiments, first energy source supply subsystem 1401 can comprise first energy source supply subsystem input mechanism 1406, one or more buffering storage vessels 1407, thermal management system 1408, compression system 1409, one or more holding storage vessels 1410, one or more holding storage vessel pressure regulators 1411, first energy source supply subsystem output mechanism 1412, cascade control system 1413, and energy source safety management system 1422. In some embodiments, as described further herein, buffering storage vessel(s) 1407, thermal management system 1408, compression system 1409, holding storage vessel pressure regulator(s) 1411, and/or cascade control system 1413 can be omitted.

In many embodiments, first energy source supply subsystem input mechanism 1406 can be similar or identical to first energy source supply subsystem input mechanism 306 (FIG. 3). For example, first energy source supply subsystem input mechanism 1406 can be configured to receive the hydrogen fuel energy source. In implementation, first energy source supply subsystem input mechanism 1406 can comprise one or more receptacles (e.g., one or more fittings) suitable to receive the hydrogen fuel energy source. In many embodiments, such as, for example, when energy source supply system 1400 is similar or identical to hub energy source supply system 118 (FIG. 1), first energy source supply subsystem input mechanism 1406 can receive the hydrogen fuel energy source from an energy storage supply station.

Further, the energy storage supply station can be similar or identical to one of energy storage supply station(s) 107 of FIG. 1 (e.g., energy storage supply station 108 (FIG. 1)). In some embodiments, such as, for example, when energy source supply system 1400 is similar or identical to appliance energy source supply system 114 (FIG. 1), first energy source supply subsystem input mechanism 1406 can receive the hydrogen fuel energy source from an energy storage supply hub and/or the energy source supply station. Further, the energy storage supply hub can be similar or identical to one of energy storage supply hub(s) 105 of FIG. 1 (e.g., energy storage supply hub 106 (FIG. 1)).

In some embodiments, first energy source supply subsystem input mechanism 1406 can comprise an input mechanism pressure sensor. For example, the input mechanism pressure sensor can detect a pressure of the hydrogen fuel energy source received by first energy source supply subsystem input mechanism 1406. In some embodiments, the input mechanism pressure sensor can be part of SDT subsystem 1403, as described below.

In many embodiments, buffering storage vessel(s) 1407 can be similar or identical to buffering storage vessel(s) 307 (FIG. 3). For example, buffering storage vessel(s) 1407 can be configured to receive the hydrogen fuel energy source from first energy source supply subsystem input mechanism 1406 and to store the hydrogen fuel energy source. Accordingly, in some embodiments, buffering storage vessel(s) 1407 can be coupled to first energy source supply subsystem input mechanism 1406, such as, for example, by one or more conduits. Further, the conduit(s) can comprise one or more valves configured to control, direct, and/or regulate flow of the hydrogen fuel energy source through the conduit(s). In implementation, buffering storage vessel(s) 1407 can comprise one or more tanks configured to store the hydrogen fuel energy source. In further embodiments, buffering storage vessel(s) 1407 can store (e.g., temporarily store) the hydrogen fuel energy source until the hydrogen fuel energy source can be received by compression system 1409.

In many embodiments, compression system 1409 can be similar or identical to compression system 309 (FIG. 3). For example, compression system 1409 can be configured to receive the hydrogen fuel energy source from buffering storage vessel(s) 1407. Accordingly, in some embodiments, compression system 1409 can be coupled to buffering storage vessel(s) 1407, such as, for example, by one or more conduits. Further, the conduit(s) can comprise one or more valves configured to control, direct, and/or regulate flow of the hydrogen fuel energy source through the conduit(s). Meanwhile, compression system 1409 can be configured to compress the hydrogen fuel energy source to increase a pressure of the hydrogen fuel energy source and to provide the compressed hydrogen fuel energy source to holding storage vessel(s) 1410. In implementation, compression system 1409 can comprise a hydrogen compressor.

In many embodiments, holding storage vessel(s) 1410 can be similar or identical to holding storage vessel(s) 310 (FIG. 3). For example, holding storage vessel(s) 1410 can be configured to receive and store the hydrogen fuel energy source. When buffering storage vessel(s) 1407 and compression system 1409 are implemented, holding storage vessel(s) 1410 can be coupled to compression system 1409, such as, for example, by one or more conduits, to receive the hydrogen fuel energy source from compression system 1409 (e.g., after the hydrogen fuel energy source is compressed by compression system 1409). Further, the conduit(s) can comprise one or more valves configured to control, direct, and/or regulate flow of the hydrogen fuel energy source through the conduit(s). Meanwhile, when buffering storage vessel(s) 1407 and compression system 1409 are omitted, holding storage vessel(s) 1410 can be coupled (e.g., directly coupled) to first energy source supply subsystem input mechanism 1406, such as, for example, by one or more conduits, to receive the hydrogen fuel energy source from first energy source supply subsystem input mechanism 1406. Further, the conduit(s) can comprise one or more valves configured to control, direct, and/or regulate flow of the hydrogen fuel energy source through the conduit(s). Nonetheless, in many embodiments, implementing buffering storage vessel(s) 1407 and compression system 1409 can advantageously permit holding storage vessel(s) 1410 to store more of the hydrogen fuel energy source.

In implementation, holding storage vessel(s) 1410 can comprise one or more tanks configured to store the hydrogen fuel energy source. In many embodiments, holding storage vessel(s) 1410 can comprise an aggregate storage capacity, and in some embodiments, each holding storage vessel of holding storage vessel(s) 1410 can be configured to store the hydrogen fuel energy source approximately at or below a predetermined storage pressure. In some embodiments, the aggregate storage capacity of holding storage vessel(s) 1410 can be greater than or equal to approximately 8 kilograms and less than or equal to approximately 73 kilograms. For example, the aggregate storage capacity of holding storage vessel(s) 310 can be approximately 8.4 kilograms. Further, in these or other embodiments, the predetermined storage pressure of holding storage vessel(s) 1410 can be greater than or equal to approximately 34.47 Megapascals (gauge) and less than or equal to approximately 68.95 Megapascals (gauge).

In many embodiments, first energy source supply subsystem output mechanism 1412 can be similar or identical to first energy source supply subsystem output mechanism 312 (FIG. 3). For example, first energy source supply subsystem output mechanism 1412 can be configured to receive the hydrogen fuel energy source from holding storage vessel(s) 1410 and to make available the hydrogen fuel energy source to second energy source supply subsystem 1402, receiver vehicle 1404, and/or energy source supply appliance 1405. Accordingly, in some embodiments, first energy source supply subsystem output mechanism 1412 can be coupled to holding storage vessel(s) 1410, such as, for example, by one or more conduits. Further, the conduit(s) can comprise one or more valves configured to control, direct, and/or regulate flow of the hydrogen fuel energy source through the conduit(s).

In implementation, first energy source supply subsystem output mechanism 1412 can comprise one or more hoses and/or nozzles suitable to receive the hydrogen fuel energy source and to make available the hydrogen fuel energy source to receiver vehicle 1404 and/or energy source supply appliance 1405. In some embodiments, the hose(s) can comprise one or more bonding cables to electrically ground the hose(s). Further, when energy source supply system 1400 comprises second energy source supply subsystem input 1414, first energy source supply subsystem output mechanism 1412 can comprise one or more conduits configured to make available the hydrogen fuel energy source to a second energy source supply subsystem input of second energy source supply subsystem 1402. For example, the second energy source supply subsystem input can be similar or identical to second energy source supply subsystem input 314 (FIG. 3). Further, the conduit(s) can comprise one or more valves configured to control, direct, and/or regulate flow of the hydrogen fuel energy source through the conduit(s). In some embodiments, first energy source supply subsystem output mechanism 1412 can be configured to make available the hydrogen fuel energy source to second energy source supply subsystem 1402 but not to receiver vehicle 1404 and/or energy source supply appliance 1405.

In some embodiments, first energy source supply subsystem output mechanism 1412 can comprise one or more safety release mechanisms. In these embodiments, the safety release mechanism(s) can couple the hose(s) and/or the nozzle(s) of first energy source supply subsystem output mechanism 1412 to energy source supply system 1400 and can permit the hose(s) and/or the nozzle(s) to decouple (e.g., break away) from energy source supply system 1400 when a force exceeding a predetermined force acts upon the safety release mechanism(s), the hose(s), and/or the nozzle(s). For example, the safety release mechanism(s) can prevent damage to part or all of energy source supply system 1400 in the event that the receiver vehicle 1404 and/or energy source supply appliance 1405 drive or otherwise move away from energy source supply system 1400 while the hose(s) and/or nozzle(s) remain coupled to receiver vehicle 1404 and/or energy source supply appliance 1405. In some embodiments, the safety release mechanism(s) can permit the hose(s) and/or the nozzle(s) to be recoupled to energy source supply system 1400 after the hose(s) and/or the nozzle(s) have been decoupled from energy source supply system 1400. In implementation, the safety release mechanism(s) can comprise any suitable breakaway connector.

In many embodiments, holding storage vessel pressure regulator(s) 1411 can be similar or identical to holding storage vessel pressure regulator(s) 311 (FIG. 3). For example, holding storage vessel pressure regulator(s) 1411 can be configured to limit a pressure of the hydrogen fuel energy source that is provided by compression system 1409 to holding storage vessel(s) 1410, such as, for example, via cascade control system 1413. In implementation, holding storage vessel pressure regulator(s) 1411 can comprise one or more pressure regulation valves. Further, holding storage vessel pressure regulator(s) 1411 can be between compression system 1409 and holding storage vessel(s) 1410. Accordingly, in some embodiments, holding storage vessel pressure regulator(s) 1411 can be coupled to compression system 1409, such as, for example, by one or more conduits, and to cascade control system 1413 or holding storage vessel(s) 1410, such as, for example, by one or more conduits. Further, the conduit(s) can comprise one or more valves configured to control, direct, and/or regulate flow of the hydrogen fuel energy source through the conduit(s). In these or other embodiments, holding storage vessel pressure regulator(s) 1411 can be implemented to prevent the pressure of the hydrogen fuel energy source being provided to holding storage vessel(s) 1410 from exceeding the predetermined storage pressure of holding storage vessel(s) 1410, thereby preventing damage to holding storage vessel(s) 1410 and/or injury to the operator of energy source supply system 1400. Nonetheless, in some embodiments, holding storage vessel pressure regulator(s) 1411 can be omitted, such as, for example, when compression system 1409 is omitted.

In many embodiments, cascade control system 1413 can be similar or identical to cascade control system 313 (FIG. 3). For example, cascade control system 1413 can be implemented when holding storage vessel(s) 1410 comprise multiple holding storage vessels. In particular, cascade control system 1413 can be configured to control filling (e.g., by compression system 1409 or first energy source supply subsystem input mechanism 1406) of the multiple holding storage vessels with the hydrogen fuel energy source in a cascading manner and/or dispensing of the hydrogen fuel energy source (e.g., to first energy source supply subsystem output mechanism 1412) from the multiple holding storage vessels in a cascading manner. In other embodiments, cascade control system 1413 can be omitted, such as, for example, when holding storage vessel(s) 1410 comprise only one holding storage vessel.

Although not illustrated in FIG. 14, in many embodiments, when energy source supply system 1400 comprises cascade control system 1413, cascade control system 1413 can be between holding storage vessel(s) 1410 and one of first energy source subsystem input mechanism 1406, buffering storage vessel(s) 1407, compression system 1409, or holding storage vessel pressure regulator(s) 1411. Accordingly, in some embodiments, cascade control system 1413 can be coupled to holding storage vessel(s) 1410 and at least one of first energy source subsystem input mechanism 1406, buffering storage vessel(s) 1407, compression system 1409, or holding storage vessel pressure regulator(s) 1411, such as, for example, by one or more conduits. Further, the conduit(s) can comprise one or more valves configured to control, direct, and/or regulate flow of the hydrogen fuel energy source through the conduit(s).

In these or other embodiments, when energy source supply system 1400 comprises cascade control system 1413, cascade control system 1413 can be between holding storage vessel(s) 1410 and one or more of energy source safety management system 1422 or first energy source subsystem output mechanism 1412. Accordingly, in some embodiments, cascade control system 1413 can be coupled to holding storage vessel(s) 1410, such as, for example, by one or more conduits, and to energy source safety management system 1422 or first energy source subsystem output mechanism 1412, such as, for example, by one or more conduits. Further, the conduit(s) can comprise one or more valves configured to control, direct, and/or regulate flow of the hydrogen fuel energy source through the conduit(s).

In many embodiments, energy source safety management system 1422 can be configured to receive the hydrogen fuel energy source from one of holding storage vessel(s) 1410 or cascade control system 1413 and to reduce a temperature of the hydrogen fuel energy source that is made available by first energy source supply subsystem output mechanism 1412 to second energy source supply subsystem 1402, receiver vehicle 1404, and/or energy source supply appliance 1405 (e.g., before the hydrogen fuel energy source is made available by first energy source supply subsystem output mechanism 1412 to second energy source supply subsystem 1402, receiver vehicle 1404, and/or energy source supply appliance 1405). For example, energy source safety management system 1422 can reduce a temperature of the hydrogen fuel energy source that is made available by first energy source supply subsystem output mechanism 1412 to second energy source supply subsystem 1402, receiver vehicle 1404, and/or energy source supply appliance 1405 such that the temperature of the hydrogen fuel energy source does not exceed a predetermined maximum delivery temperature. Reducing the temperature of the hydrogen fuel energy source that is made available by first energy source supply subsystem output mechanism 1412 to second energy source supply subsystem 1402, receiver vehicle 1404, and/or energy source supply appliance 1405 such that the temperature of the hydrogen fuel energy source does not exceed the predetermined maximum delivery temperature can prevent damage to second energy source supply subsystem 1402, receiver vehicle 1404, and/or energy source supply appliance 1405. In many embodiments, the predetermined maximum delivery temperature can be any suitable temperature. However, in some embodiments, the predetermined maximum delivery temperature can be selected to be less than a melting temperature of part or all of second energy source supply subsystem 1402, receiver vehicle 1404, and/or energy source supply appliance 1405. For example, in further embodiments, the predetermined maximum delivery temperature can be selected to be less than a melting temperature of a plastic liner of a fuel tank of receiver vehicle 1404.

In many embodiments, energy source safety management system 1422 can be between one of holding storage vessel(s) 1410 or cascade control system 1413 and first energy source supply subsystem output mechanism 1412. Accordingly, in some embodiments, energy source safety management system 1422 can be coupled to at least one of holding storage vessel(s) 1410 or cascade control system 1413, such as, for example, by one or more conduits, and to first energy source supply subsystem output mechanism 1412, such as, for example, by one or more conduits. Further, the conduit(s) can comprise one or more valves configured to control, direct, and/or regulate flow of the hydrogen fuel energy source through the conduit(s).

Figure 15:
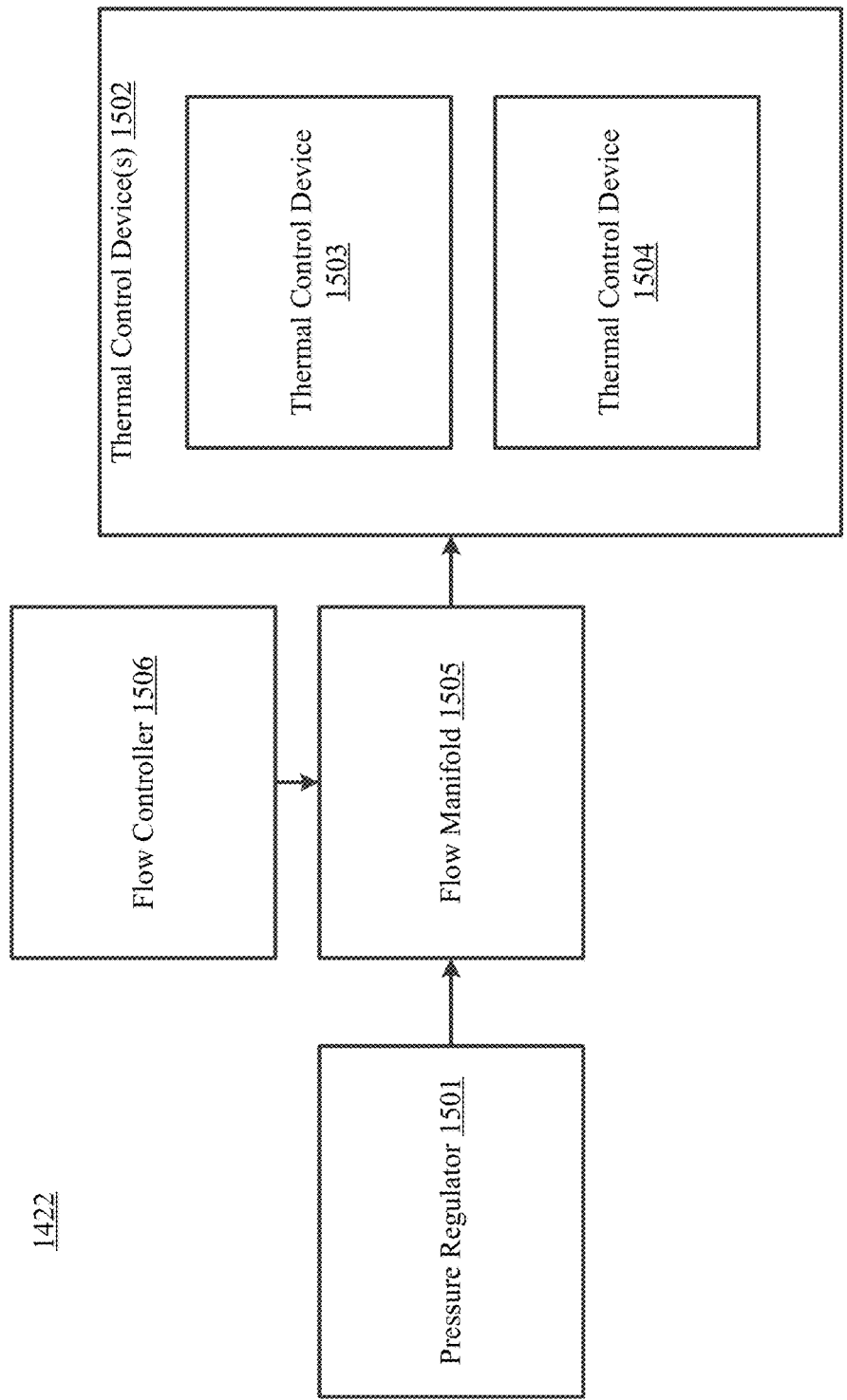
FIG. 15 illustrates an exemplary block diagram for an energy source safety management system, according to the embodiment of FIG. 14.

Turning ahead in the drawings, FIG. 15 illustrates an exemplary block diagram for energy source safety management system 1422, according to the embodiment of FIG. 14. In many embodiments, energy source safety management system 1422 comprises pressure regulator 1501 and one or more thermal control devices 1502. For example, thermal control device(s) 1502 can comprise thermal control device 1503. Further, when thermal control device(s) 1502 comprise multiple thermal control devices, thermal control device(s) 1502 also can comprise thermal control device 1504, and energy source safety management system 1422 can comprise flow manifold 1505. In some embodiments, when thermal control device(s) 1502 comprise multiple thermal control devices, energy source safety management system 1422 also can comprise flow controller 1506. In other embodiments, thermal control device 1504, flow manifold 1505, and/or flow controller 1506 can be omitted.

In many embodiments, pressure regulator 1501 can be configured to receive the hydrogen fuel energy source received by energy source safety management system 1422 and to limit a pressure of the hydrogen fuel energy source received by pressure regulator 1501 to a predetermined pressure (e.g., before the hydrogen fuel energy source is made available by first energy source supply subsystem output mechanism 1412 (FIG. 14) to second energy source supply subsystem 1402 (FIG. 14), receiver vehicle 1404 (FIG. 14), and/or energy source supply appliance 1405 (FIG. 14)). For example, in some embodiments, pressure regulator 1501 can be configured to receive the hydrogen fuel energy source from one of holding storage vessel(s) 1410 (FIG. 4) or cascade control system 1413 (FIG. 4). Accordingly, in some embodiments, pressure regulator 1501 can be coupled to at least one of holding storage vessel(s) 1410 (FIG. 4) or cascade control system 1413 (FIG. 4), such as, for example, by one or more conduits (e.g., the conduit(s) coupling energy source safety management system 1422 to at least one of holding storage vessel(s) 1410 (FIG. 14) or cascade control system 1413 (FIG. 14)). Meanwhile, in many embodiments, the predetermined pressure can be any suitable pressure. However, in some embodiments, the predetermined pressure can be greater than or equal to approximately 12.4 Megapascals (gauge). In implementation, pressure regulator 1501 can comprise a pressure regulation valve.

In many embodiments, thermal control device(s) 1502 (e.g., thermal control device 1503 and/or thermal control device 1504) each can be configured to receive the hydrogen fuel energy source from pressure regulator 1501 and to reduce a temperature of the hydrogen fuel energy source when that thermal control device receives the hydrogen fuel energy source (e.g., after pressure regulator 1501 has limited the pressure of the hydrogen fuel energy source received by pressure regulator 1501 to the predetermined pressure, and/or before the hydrogen fuel energy source is made available by first energy source supply subsystem output mechanism 1412 to second energy source supply subsystem 1402, receiver vehicle 1404, and/or energy source supply appliance 1405). For example, in some embodiments, thermal control device(s) 1502 (e.g., thermal control device 1503 and/or thermal control device 1504) can be configured to receive the hydrogen fuel energy source from pressure regulator 1501. Accordingly, in some embodiments, thermal control device(s) 1502 (e.g., thermal control device 1503 and/or thermal control device 1504) can be coupled to pressure regulator 1501, such as, for example, by one or more conduits. Further, the conduit(s) can comprise one or more valves configured to control, direct, and/or regulate flow of the hydrogen fuel energy source through the conduit(s). In some embodiments, the conduit(s) can comprise a blow off valve. In these or other embodiments, the conduit(s) can comprise a vent configured to permit an operator of energy source supply system 1400 (FIG. 14) to vent the conduit(s).

Further, each of thermal control device(s) 1502 (e.g., thermal control device 1503 and/or thermal control device 1504) can be configured to provide the hydrogen fuel energy source to first energy source supply subsystem output mechanism 1412 (FIG. 14) (e.g., after reducing the temperature of the hydrogen fuel energy source). Accordingly, in some embodiments, thermal control device(s) 1502 (e.g., thermal control device 1503 and/or thermal control device 1504) can be coupled to first energy source supply subsystem output mechanism 1412 (FIG. 14), such as, for example, by one or more conduits (e.g., the conduit(s) coupling energy source safety management system 1422 to first energy source supply subsystem output mechanism 1412 (FIG. 14)).

In many embodiments, thermal control device 1503 can be configured to receive the hydrogen fuel energy source and to converge a flow of the hydrogen fuel energy source to cause a temperature reduction of the hydrogen fuel energy source when thermal control device 1503 receives the hydrogen fuel energy source. For example, by converging the flow of the hydrogen fuel energy source, as a result of the Venturi effect, thermal control device 1503 can cause a velocity of the hydrogen fuel energy source to increase, a pressure and a temperature of the hydrogen fuel energy source to decrease, and a mass flow rate of the hydrogen fuel energy source to remain constant. Further, the increase in velocity and the decrease in pressure and temperature of the hydrogen fuel energy source can be mathematically calculated as a function of the magnitude by which the flow of the hydrogen fuel energy source is converged. As described in greater detail below, the decrease in temperature also can be mathematically calculated as a function of an inlet temperature of the hydrogen fuel energy source (i.e., a temperature of the hydrogen fuel energy source before the flow of the hydrogen fuel energy source is converged). In many embodiments, the inlet temperature can be approximately equal to an ambient temperature at or near energy source supply system 1400 (FIG. 14).

In implementation, thermal control device 1503 can comprise a restrictive flow orifice. As used herein, the term "restrictive flow orifice" refers to an orifice plate comprising an orifice and an orifice diameter of the orifice. Accordingly, the restrictive flow orifice can receive the hydrogen fuel energy source at the orifice, which can converge the flow of the hydrogen fuel energy source as the hydrogen fuel energy source passes through the orifice. Meanwhile, the magnitude by which the flow of the hydrogen fuel energy source is converged can be a function of the orifice diameter of the orifice.

In many embodiments, implementing thermal control device 1503 as a restrictive flow orifice can be advantageous when thermal control device 1503 is also implemented with pressure regulator 1501 because, for a particular orifice diameter of the orifice and when the hydrogen fuel energy source is limited to the predetermined pressure by pressure regulator 1501, a temperature reduction of the hydrogen fuel energy source caused by thermal control device 1503 can be known, specific, and consistent. Accordingly, the orifice diameter of the restrictive flow orifice can be optimized to a diameter that results in a highest mass flow rate of the hydrogen fuel energy source (e.g., permitting the hydrogen fuel energy source to be provided by first energy source supply subsystem output mechanism 1412 (FIG. 14) to second energy source supply subsystem 1402 (FIG. 14), receiver vehicle 1404 (FIG. 14), and/or energy source supply appliance 1405 (FIG. 14) as quickly as possible) but that also ensures that a temperature increase in the hydrogen fuel energy source resulting from first energy source supply subsystem output mechanism 1412 (FIG. 14) providing the hydrogen fuel energy source to second energy source supply subsystem 1402 (FIG. 14), receiver vehicle 1404 (FIG. 14), and/or energy source supply appliance 1405 (FIG. 14) does not exceed the temperature reduction of the hydrogen fuel energy source caused by thermal control device 1503 or exceed the temperature reduction by more than a predetermined amount (e.g., for a predetermined mass of the hydrogen fuel energy source provided). As a result, thermal control device 1503 can prevent the temperature of the hydrogen fuel energy source from exceeding the predetermined maximum delivery temperature, as described above. Further, because the mass flow rate through the restrictive flow orifice also can be known, specific, and consistent, a time for a predetermined mass of the hydrogen fuel energy source to be provided by first energy source supply subsystem output mechanism 1412 (FIG. 14) to second energy source supply subsystem 1402 (FIG. 14), receiver vehicle 1404 (FIG. 14), and/or energy source supply appliance 1405 (FIG. 14) can be calculated, thereby permitting an operator of energy source supply system 1400 (FIG. 14) to provide the predetermined mass of the hydrogen fuel energy source as a function of time, and permitting confirmation that the calculated time is not long enough to cause a temperature increase in the hydrogen fuel energy source to exceed the temperature reduction of the hydrogen fuel energy source caused by thermal control device 1503 or to exceed the temperature reduction by the predetermined amount. For example, the predetermined mass of the hydrogen fuel energy source can comprise approximately 1 kilogram. Further, in some embodiments, the time for the predetermined mass of the hydrogen fuel energy source to be provided by first energy source supply subsystem output mechanism 1412 (FIG. 14) to second energy source supply subsystem 1402 (FIG. 14), receiver vehicle 1404 (FIG. 14), and/or energy source supply appliance 1405 (FIG. 14) can depend on a change (e.g., increase) in pressure at second energy source supply subsystem 1402 (FIG. 14), receiver vehicle 1404 (FIG. 14), and/or energy source supply appliance 1405 (FIG. 14) as second energy source supply subsystem 1402 (FIG. 14), receiver vehicle 1404 (FIG. 14), and/or energy source supply appliance 1405 (FIG. 14) receive the hydrogen fuel energy source. Meanwhile, because an operator of energy source supply system 1400 (FIG. 14) can be confident that a temperature increase in the hydrogen fuel energy source is not exceeding the temperature reduction of the hydrogen fuel energy source caused by thermal control device 1503 or exceeding the temperature reduction by the predetermined amount, first energy source supply subsystem output mechanism 1412 (FIG. 14) can make available the hydrogen fuel energy source to second energy source supply subsystem 1402 (FIG. 14), receiver vehicle 1404 (FIG. 14), and/or energy source supply appliance 1405 (FIG. 14) without receiving temperature data therefrom (e.g., to monitor a temperature at second energy source supply subsystem 1402 (FIG. 14), receiver vehicle 1404 (FIG. 14), and/or energy source supply appliance 1405 (FIG. 14)).

In many embodiments, thermal control device 1503 can be devoid of moving parts, such as, for example, when thermal control device 1503 comprises a restrictive flow orifice. Implementing thermal control device 1503 to be devoid of moving parts advantageously can mitigate or eliminate operational error by an operator of energy source supply system 1400 (FIG. 14) incorrectly operating thermal control device 1503. Further, implementing thermal control device 1503 to be devoid of moving parts advantageously can mitigate mechanical failure of thermal control device 1503.

In many embodiments, when thermal control device(s) 1502 (e.g., thermal control device 1503 and/or thermal control device 1504) comprise multiple thermal control devices, each of the thermal control devices of the multiple thermal control devices can be similar to each other but can cause a different temperature reduction of the hydrogen fuel energy source, and in some embodiments, can pass the hydrogen fuel energy source with different mass flow rates. For example, when thermal control device(s) 1502 (e.g., thermal control device 1503 and/or thermal control device 1504) comprise multiple thermal control devices, and when the multiple thermal control devices comprise multiple restrictive flow orifices, the multiple restrictive flow orifices can comprise different orifice diameters.

In these or other embodiments, thermal control device(s) 1502 (e.g., thermal control device 1503 and/or thermal control device 1504) can comprise any suitable orifice diameter or orifice diameters. In many embodiments, the orifice diameter(s) of thermal control device 1503 and/or thermal control device 1504 can be greater than or equal to approximately 0.0178 centimeter and less than or equal to approximately 0.102 centimeter. For example, the orifice diameter of thermal control device 1503 can comprise one of approximately 0.0178 centimeter, approximately 0.0381 centimeter, approximately 0.0457 centimeter, approximately 0.0508 centimeter, approximately 0.0635 centimeter, approximately 0.0762 centimeter, or approximately 0.102 centimeter. Meanwhile, when thermal control device(s) 1502 (e.g., thermal control device 1503 and/or thermal control device 1504) comprise multiple thermal control devices, an orifice diameter of another thermal control device of the multiple thermal control devices (e.g., thermal control device 1504) can comprise a different one of approximately 0.0178 centimeter, approximately 0.0381 centimeter, approximately 0.0457 centimeter, approximately 0.0508 centimeter, approximately 0.0635 centimeter, approximately 0.0762 centimeter, or approximately 0.102 centimeter.

In some embodiments, when the orifice diameter of thermal control device 1503 comprises approximately 0.0178 centimeter, the mass flow rate through thermal control device 1503 can be approximately 0.176 grams per second, and the time to transfer approximately 1 kilogram of the hydrogen fuel energy source can be approximately 94.7 minutes, such as, for example, at an ambient temperature of approximately 50 degrees Celsius. In some embodiments, when the orifice diameter of thermal control device 1503 comprises approximately 0.0381 centimeter, the mass flow rate through thermal control device 1503 can be approximately 0.789 grams per second, and the time to transfer approximately 1 kilogram of the hydrogen fuel energy source can be approximately 21.1 minutes, such as, for example, at an ambient temperature of approximately 40 degrees Celsius. In some embodiments, when the orifice diameter of thermal control device 1503 comprises approximately 0.0457 centimeter, the mass flow rate through thermal control device 1503 can be approximately 1.13 grams per second, and the time to transfer approximately 1 kilogram of the hydrogen fuel energy source can be approximately 14.8 minutes, such as, for example, at an ambient temperature of approximately 35 degrees Celsius. In some embodiments, when the orifice diameter of thermal control device 1503 comprises approximately 0.0508 centimeter, the mass flow rate through thermal control device 1503 can be approximately 1.40 grams per second, and the time to transfer approximately 1 kilogram of the hydrogen fuel energy source can be approximately 11.9 minutes, such as, for example, at an ambient temperature of approximately 30 degrees Celsius. In some embodiments, when the orifice diameter of thermal control device 1503 comprises approximately 0.0635 centimeter, the mass flow rate through thermal control device 1503 can be approximately 2.19 grams per second, and the time to transfer approximately 1 kilogram of the hydrogen fuel energy source can be approximately 7.6 minutes, such as, for example, at an ambient temperature of approximately 25 degrees Celsius. In some embodiments, when the orifice diameter of thermal control device 1503 comprises approximately 0.0762 centimeter, the mass flow rate through thermal control device 1503 can be approximately 3.16 grams per second, and the time to transfer approximately 1 kilogram of the hydrogen fuel energy source can be approximately 5.3 minutes, such as, for example, at an ambient temperature of approximately 20 degrees Celsius. In some embodiments, when the orifice diameter of thermal control device 1503 comprises approximately 0.102 centimeter, the mass flow rate through thermal control device 1503 can be approximately 5.61 grams per second, and the time to transfer approximately 1 kilogram of the hydrogen fuel energy source can be approximately 3.0 minutes, such as, for example, at an ambient temperature of approximately 10 degrees Celsius.

Further, in many embodiments, when thermal control device(s) 1502 (e.g., thermal control device 1503 and/or thermal control device 1504) comprise multiple thermal control devices, the multiple thermal control devices can be configured to receive the hydrogen fuel energy source at different times. For example, in these or other embodiments, the multiple thermal control devices (e.g., thermal control device 1503 and/or thermal control device 1504) can be coupled to pressure regulator 1501 and/or to first energy source supply subsystem output mechanism 1412 (FIG. 14) in parallel. Further, in these or other embodiments, when thermal control device(s) 1502 (e.g., thermal control device 1503 and/or thermal control device 1504) comprise multiple thermal control devices, the hydrogen fuel energy source can be selectively received by one of the multiple thermal control devices, such as, for example, when energy source safety management system 1422 comprises flow manifold 1505.

When thermal control device(s) 1502 (e.g., thermal control device 1503 and/or thermal control device 1504) comprise multiple thermal control devices, flow manifold 1505 can receive the hydrogen fuel energy source and can permit the hydrogen fuel energy source to be selectively provided to one of the multiple thermal control devices at different times. Selectively providing the hydrogen fuel energy source to one of the multiple thermal control devices at different times advantageously can permit the thermal control device of the multiple thermal control devices having a largest orifice diameter that will not cause a temperature increase in the hydrogen fuel energy source resulting from first energy source supply subsystem output mechanism 1412 (FIG. 14) providing the hydrogen fuel energy source to second energy source supply subsystem 1402 (FIG. 14), receiver vehicle 1404 (FIG. 14), and/or energy source supply appliance 1405 (FIG. 14) to exceed the temperature reduction of the hydrogen fuel energy source caused by the thermal control device or exceed the temperature reduction by more than a predetermined amount to be used to provide the hydrogen fuel energy source to first energy source supply subsystem output mechanism 1412 (FIG. 14).

As noted above, the temperature reduction can depend on an ambient temperature at or near energy source supply system 1400 (FIG. 14). Accordingly, in many embodiments, when thermal control device(s) 1502 (e.g., thermal control device 1503 and/or thermal control device 1504) comprise multiple thermal control devices, the thermal control device of thermal control device(s) 1502 selected to receive the hydrogen fuel energy source can be selected based on a current ambient temperature at or near energy source supply system 1400 (FIG. 14). For example, in some embodiments, when thermal control device(s) 1502 (e.g., thermal control device 1503 and/or thermal control device 1504) comprise multiple thermal control devices, one thermal control device of the multiple thermal control devices (e.g., thermal control device 1503) can be selected when the current ambient temperature is less than or equal to a predetermined ambient temperature, and another thermal control device of the multiple thermal control devices (e.g., thermal control device 1504) can be selected when the current ambient temperature is greater than the predetermined ambient temperature. For example, in some embodiments, the predetermined ambient temperature can be one of approximately 10 degrees Celsius, approximately 20 degrees Celsius, approximately 25 degrees Celsius, approximately 30 degrees Celsius, approximately 35 degrees Celsius, approximately 40 degrees Celsius, or approximately 50 degrees Celsius. In some embodiments, when the predetermined ambient temperature is approximately 25 degrees Celsius, one thermal control device of the multiple thermal control devices (e.g., thermal control device 1503) can comprise an orifice diameter of approximately 0.0635 centimeter, and another thermal control device of the multiple thermal control devices (e.g., thermal control device 1504) can comprise an orifice diameter of approximately 0.0457 centimeter.

In these or other embodiments, when thermal control device(s) 1502 (e.g., thermal control device 1503 and/or thermal control device 1504) comprise multiple thermal control devices, the thermal control device of thermal control device(s) 1502 selected to receive the hydrogen fuel energy source can be selected based on a current clock time and/or a current clock date. For example, the current ambient temperature can be a function of the current clock time and/or the current clock date.

In many embodiments, flow manifold 1505 can be between pressure regulator 1501 and thermal control device(s) 1502. Accordingly, in some embodiments, flow manifold 1505 can be coupled to pressure regulator 1501, such as, for example, by one or more conduits, and to thermal control device(s) 1502, such as, for example, by one or more conduits. In implementation, flow manifold 1505 can comprise a multi-directional valve. In some embodiments, flow manifold 1505 can be manually operated to select which one of the multiple thermal control devices of thermal control device(s) 1502 (e.g., thermal control device 1503 and/or thermal control device 1504) receives the hydrogen fuel energy source. In other embodiments, flow manifold 1505 can be automatically operated to select which one of the multiple thermal control devices of thermal control device(s) 1502 (e.g., thermal control device 1503 and/or thermal control device 1504) receives the hydrogen fuel energy source, such as, for example, when energy source safety management system 1422 comprises flow controller 1506. In some embodiments, flow manifold 1505 can be omitted, such as, for example, when thermal control device(s) 1502 comprise one thermal control device (e.g., thermal control device 1503).

Flow controller 1506 can comprise a microcontroller configured to automatically operate flow manifold 1505 to select which one of the multiple thermal control devices of thermal control device(s) 1502 (e.g., thermal control device 1503 and/or thermal control device 1504) receives the hydrogen fuel energy source. In many embodiments, as explained above, the microcontroller can determine which one of the multiple thermal control devices of thermal control device(s) 1502 (e.g., thermal control device 1503 and/or thermal control device 1504) receives the hydrogen fuel energy source based on a current ambient temperature at or near energy source supply system 1400 (FIG. 14), a current clock time, and/or a current clock date. In some embodiments, flow controller 1506 can be electrically coupled to flow manifold 1505.

In many embodiments, energy source safety management system 1422 can comprise an ambient temperature sensor. The ambient temperature sensor can detect a current ambient temperature at or near energy source supply system 1400 (FIG. 14). In some embodiments, the ambient temperature sensor can be part of SDT subsystem 1403 (FIG. 14), as described below. Further, when thermal control device(s) 1502 (e.g., thermal control device 1503 and/or thermal control device 1504) comprise multiple thermal control devices, when energy source safety management system 1422 comprises flow controller 1506, and when flow controller 1506 determines which one of the multiple thermal control devices receives the hydrogen fuel energy source based on a current ambient temperature at or near energy source supply system 1400 (FIG. 14), flow controller 1506 can receive the current ambient temperature from the ambient temperature sensor. In other embodiments, when thermal control device(s) 1502 (e.g., thermal control device 1503 and/or thermal control device 1504) comprise multiple thermal control devices, and when the thermal control device of the multiple thermal control devices is determined manually based on a current ambient temperature at or near energy source supply system 1400 (FIG. 14), an operator of energy source supply system 1400 (FIG. 14) can review the current ambient temperature detected by the ambient temperature sensor.

In many embodiments, energy source safety management system 1422 can comprise a pressure regulator pressure sensor. The pressure regulator pressure sensor can detect a pressure of the hydrogen fuel energy source after the hydrogen fuel energy source has been limited to the predetermined pressure by pressure regulator 1501. Accordingly, when pressure regulator 1501 is operating properly, the pressure detected by pressure regulator pressure sensor is approximately equal to the predetermined pressure of pressure regulator 1501. In some embodiments, the pressure regulator pressure sensor can be part of SDT subsystem 1403 (FIG. 14), as described below.

In some embodiments, energy source safety management system 1422 can comprise an inlet pressure sensor and/or an inlet temperature sensor upstream of thermal control device(s) 1502. In these or other embodiments, energy source safety management system 1422 can comprise an outlet pressure sensor and/or an outlet temperature sensor downstream of thermal control device(s) 1502. The inlet pressure sensor can detect a pressure of the hydrogen fuel energy source upstream of thermal control device(s) 1502, and the inlet temperature sensor can detect a temperature of the hydrogen fuel energy source upstream of thermal control device(s) 1502. Meanwhile, the outlet pressure sensor can detect a pressure of the hydrogen fuel energy source downstream of thermal control device(s) 1502, and the outlet temperature sensor can detect a temperature of the hydrogen fuel energy source downstream of thermal control device(s) 1502. In some embodiments, the inlet pressure sensor, the inlet temperature sensor, the outlet pressure sensor, and/or the outlet temperature sensor can be part of SDT subsystem 1403 (FIG. 14), as described below.

In many embodiments, thermal control device(s) 1502 (e.g., thermal control device 1503 and/or thermal control device 1504) can be interchangeable with one or more other thermal control devices at different times, and when thermal control device(s) 1502 comprise multiple thermal control devices, can be interchangeable with each other. For example, interchanging a thermal control device of thermal control device(s) 1502 (e.g., thermal control device 1503) with another thermal control device can permit a different temperature reduction to be applied to the hydrogen fuel energy source, as desired. In these or other embodiments, the thermal control device of thermal control device(s) 1502 (e.g., thermal control device 1503) can be decoupled from energy source safety management system 1422 and replaced with the other thermal control device (e.g., thermal control device 1504 or another thermal control device) in order to interchange the thermal control device with the other thermal control device.

Referring now back to FIG. 14, in many embodiments, thermal management system 1408 can be configured to thermally manage (e.g., cool) at least part of first energy source supply subsystem 1401 (e.g., holding storage vessel(s) 1410) to prevent or mitigate thermal stress on energy source supply system 1400. In some embodiments, thermally managing (e.g., cooling) holding storage vessel(s) 1410 can prevent holding storage vessel(s) 1410 from overheating when holding storage vessel(s) 1410 are supplying the hydrogen fuel energy source to first energy source supply subsystem output mechanism 1412. For example, in many embodiments, thermal management system 1408 can be in thermal communication with holding storage vessel(s) 1410.

In implementation, thermal management system 1408 can comprise any suitable device or devices configured to thermally manage (e.g., cool) at least part of first energy source supply subsystem 1401 (e.g., holding storage vessel(s) 1410). For example, in some embodiments, thermal management system 1408 can comprise one or more heat sinks, one or more thermoelectric coolers, one or more forced air devices (e.g., one or more fans), etc.

In some embodiments, such as, for example, when energy source supply system 1400 is similar or identical to appliance energy source supply system 114 (FIG. 1), second energy source supply subsystem 1402 can be similar or identical to second appliance energy source supply subsystem 116 (FIG. 1), and vice versa. In other embodiments, such as, for example, when energy source supply system 1400 is similar or identical to hub energy source supply system 118 (FIG. 1), second energy source supply subsystem 1402 can be similar or identical to second hub energy source supply subsystem 120 (FIG. 1), and vice versa.

Further, in some embodiments, second energy source supply subsystem 1402 can be similar or identical to second energy source supply subsystem 302 (FIG. 3). For example, in some embodiments, second energy source supply subsystem 1402 can be configured to make available a second energy source to receiver vehicle 1420 and/or energy source supply appliance 1405, and the second energy source can comprise an electrical energy source (i.e., electricity). In many embodiments, receiver vehicle 1420 can be similar or identical to one of receiver vehicle(s) 109 of FIG. 1 (e.g., receiver vehicle 111 (FIG. 1)). In many embodiments, second appliance energy source supply subsystem 1402 can make available the electrical energy source (i.e., electricity) to receiver vehicle 1420 and/or energy source supply appliance 1405 when first appliance energy source supply subsystem 1401 is making available the hydrogen fuel energy source to receiver vehicle 1404 and/or energy source supply appliance 1405.

In many embodiments, SDT subsystem 1403 can be similar or identical to SDT subsystem 303 (FIG. 3). For example, SDT subsystem 1403 can be configured to log performance data of energy source supply system 1400. In these or other embodiments, SDT subsystem 1403 can be configured to monitor energy source supply system 1400 (e.g., first energy source supply subsystem 1401 and/or second energy source supply subsystem 1402) and diagnose problems affecting energy source supply system 1400 (e.g., first energy source supply subsystem 1401 and/or second energy source supply subsystem 1402). For example, in some embodiments, SDT subsystem 1403 can compare measured parameters (e.g., voltage, current, pressure, temperature, etc.) applying to energy source supply system 1400 (e.g., first energy source supply subsystem 1401 and/or second energy source supply subsystem 1402) to predetermined boundary conditions to determine if the measured parameters are outside of the boundary conditions (e.g., over/under voltage, over/under current, over/under pressure, over/under temperature, etc.) or are trending toward an out-of-bounds condition. Based on the severity of the out-of-bounds condition and/or the criticality of the affected portion or portions of energy source supply system 1400 (e.g., first energy source supply subsystem 1401 and/or second energy source supply subsystem 1402) can identify an out-of-bounds condition as being non-impactful, as requiring attention within a designated time frame (i.e., an alert condition), as requiring immediate attention (i.e., an alarm condition), or as being a system failure. In many embodiments, SDT subsystem 1403 can deactivate energy source supply system 1400 (e.g., first energy source supply subsystem 1401 and/or second energy source supply subsystem 1402) or the affected portion or portions of energy source supply system 1400 (e.g., first energy source supply subsystem 1401 and/or second energy source supply subsystem 1402) in the event of an alarm condition or system failure.

In implementation, SDT subsystem 1403 can comprise one or more sensors configured to measure one or more parameters (e.g., voltage, current, pressure, temperature, etc.) applying to energy source supply system 1400 (e.g., first energy source supply subsystem 1401 and/or second energy source supply subsystem 1402). Further, SDT subsystem 1403 can comprise one or more microcontrollers configured to log performance data of energy source supply system 1400 and/or to analyze the one or more parameters measured by the sensor(s) and compare the parameters to the predetermined boundary conditions. Further still, SDT subsystem 1403 can comprise one or more safety devices configured to prevent propagation and/or amplification of failures in energy source supply system 1400 (e.g., first energy source supply subsystem 1401 and/or second energy source supply subsystem 1402). Exemplary safety device(s) can include fuses, circuit breakers, stop valves, blow-off valves, etc. In these embodiments, SDT subsystem 1403 (e.g., the microcontroller(s) of SDT subsystem 1403) can activate one or more of the safety device(s) of SDT subsystem 1403 to prevent propagation and/or amplification of failures in energy source supply system 1400, such as, for example, in response to one or more parameters measured by the sensor(s) of SDT subsystem 1403 and/or analyzed by the microcontroller(s) of SDT subsystem 1403. Further, in some embodiments, in determining when to activate one or more of the safety device(s) of SDT subsystem 1403, SDT subsystem 1403 (e.g., the microcontroller(s) of SDT subsystem 1403) can use adaptive logic and/or machine learning to build upon a failure mode effect criticality analysis (FMECA) of energy source supply system 1400. For example, the FMECA can be based on one or more look-up tables of potential faults and the associated consequences, severity, and/or probability of the potential faults. In further embodiments, the look-up tables can establish where the sensor(s) and/or safety device(s) of SDT subsystem 1403 are located within energy source supply system 1400. In some embodiments, SDT subsystem 1403 (e.g., the microcontroller(s) of SDT subsystem 1403) can confirm the presences of faults using anomaly test logic prior to activating one or more of the safety device(s) of SDT subsystem 1403.

In some embodiments, SDT subsystem 1403 can be configured to implement a learning logic flow. For example, SDT subsystem 1403 can characterize the sensor(s) of SDT subsystem 1403, rate the sensor(s) of SDT subsystem 1403 for criticality, implement a baseline operation, poll the sensor(s) of SDT subsystem 1403 for operational data, compare the operational data to alert and alarm lookup tables, and trigger alert and alarm notifications when operational data is outside accepted tolerances of the alert and alarm lookup tables. Polling frequency and comparisons can be added or modified based on occurrences of the operational data being outside accepted tolerance of the alert and alarm lookup tables.

In many embodiments, control subsystem 1424 can be similar or identical to control subsystem 324 (FIG. 3). For example, in many embodiments, control subsystem 1424 can be configured to control energy source supply system 1400 (e.g., first energy source supply subsystem 1401, second energy source supply subsystem 1402, SDT subsystem 1403, communication subsystem 1421, and/or electric power subsystem 1425). For example, in many embodiments, control subsystem 1424 can comprise a computer system. In some embodiments, the computer system can be similar or identical to computer system 2200 (FIG. 22).

In many embodiments, communication subsystem 1421 can be similar or identical to communication subsystem 321 (FIG. 3). For example, in many embodiments, communication subsystem 1421 can be configured to provide communication between first energy source supply subsystem 1401, second energy source supply subsystem 1402, SDT subsystem 1403, control subsystem 1424, and/or electric power subsystem 1425, and/or within first energy source supply subsystem 1401, second energy source supply subsystem 1402, SDT subsystem 1403, control subsystem 1424, and/or electric power subsystem 1425. In implementation, communication subsystem 1421 can comprise a control area network vehicle bus (CAN bus).

In some embodiments, communication subsystem 1421 can accept cellular network communication (via a cellular network transponder), which may include deployment directions for energy source supply system 1400. In some embodiments, deployment directions for energy source supply system 1400 can be provided based on a location of receiver vehicle 1404 and/or receiver vehicle 1420, and/or a time to on-site energy transfer (service) calculation. The location and timing information can be relayed by communication subsystem 1421 to control subsystem 1424 to initiate a system readiness polling of SDT subsystem 1403 and electric power subsystem 1425. Based on confirmation of acceptable polling results (e.g., functionality and safety checklist), control subsystem 1424 can instruct second energy source supply subsystem 1402 to initiate preparatory actions necessary to transfer energy to receiver vehicle 1404 and/or receiver vehicle 1420 within the timeframe of the expected arrival at location or locations of receiver vehicle 1404 and/or receiver vehicle 1420. Based on confirmation of acceptable polling results control subsystem 1424 also can instruct thermal management subsystem 1408 to initiate a pre-cool down procedure of second energy source supply subsystem 1402. Implementing a pre-cool down procedure can avoid thermal and mechanical stresses to equipment, thereby increasing equipment life, decreasing a probability of thermal related failure modes/safety events, and/or more efficiently applying on-platform cooling potential energy, such as, for example, by avoiding steady state environmental temperature maintenance. In some embodiments, the pre-cool down procedure can be implemented without using energy from second energy source supply subsystem 1402, and/or with minimum propagation delay because it can be performed with solid state thermal management.

In many embodiments, electric power subsystem 1425 can be similar or identical to electric power subsystem 325 (FIG. 3). For example, in many embodiments, electric power subsystem 1425 can be configured to electrically power one or more (e.g., all) electrical components of energy source supply system 1400, first energy source supply subsystem 1401, second energy source supply subsystem 1402, SDT subsystem 1403, control subsystem 1404, and/or communication subsystem 1421. Accordingly, in these embodiments, electric power subsystem 1425 can be coupled (e.g., electrically coupled) to any electrical components of energy source supply system 1400, first energy source supply subsystem 1401, second energy source supply subsystem 1402, SDT subsystem 1403, control subsystem 1404, and/or communication subsystem 1421 that electric power subsystem 1425 is configured to electrically power.

In implementation, electric power subsystem 1425 can comprise one or more rechargeable energy storage systems. For example, in these embodiments, the rechargeable energy storage system(s) can store an electrical energy source (i.e., electricity) and make available the electrical energy source to one or more (e.g., all) electrical components of energy source supply system 1400, first energy source supply subsystem 1401, second energy source supply subsystem 1402, SDT subsystem 1403, control subsystem 1404, and/or communication subsystem 1421. Further, in these embodiments, the rechargeable energy storage system(s) can comprise (a) one or more electrochemical cells (e.g., one or more batteries), (b) one or more capacitive energy storage systems (e.g., super capacitors such as electric double-layer capacitors), and/or (c) one or more inertial energy storage systems (e.g., one or more flywheels).

Further, electric power subsystem 1425 can comprise a battery charger. The battery charger can be configured to receive an electrical energy source (i.e., electricity), such as, for example, from a utility electric grid, and to make available the electrical energy source to the rechargeable energy storage system(s) of electric power subsystem 1425.

In many embodiments, thermal management system 1408 can be configured to thermally manage (e.g., cool) at least part of electric power subsystem 1425. Thermally managing electric power subsystem 1425 can improve an operating efficiency of electric power subsystem 1425. For example, in many embodiments, thermal management system 1408 can be in thermal communication with electric power subsystem 1425.

In some embodiments, thermal management system 1408 can comprise a reservoir of coolant, a distribution circuit configured to deliver the coolant to the part or parts of energy source supply system 1400 that thermal management system 1408 is thermally managing, a heat exchanger subsystem to accept and vent heat transferred to the coolant by the part or parts of energy source supply system 1400 that thermal management system 1408 is thermally managing, a coolant distribution controller configured to control distribution of the coolant through the distribution circuit, distributed temperature sensors to provide temperature data to the coolant distribution controller about the part or parts of energy source supply system 1400 that thermal management system 1408 is thermally managing, and end cooling plates configured to put the coolant in thermal contact with any part or parts of energy source supply system 1400 that thermal management system 1408 is thermally managing.

In many embodiments, one or more of the elements of energy source supply system 1400 can be positioned to minimize thermal and/or electromagnetic interference at energy source supply system 1400. Positioning of one or more elements of energy source supply system 1400 can be determined in view of a volume available to house the elements of energy source supply system 1400, a shared thermal stress of the elements of energy source supply system 1400, and/or a risk of electromagnetically induced cross talk or interference. In some embodiments, one or more of the elements of energy source supply system 1400 can be positioned such that high power electrical pathways are separate from data, sensor, and low voltage electrical signals. In further embodiments, coolant for thermal management system 1408 can be separately routed to maximize volume for modular expansion of energy source supply system 1400. In many embodiments, separating high power electrical pathways from data, sensor, and low voltage electrical signals and/or separately routing coolant for thermal management system 1408 can permit optimal access to the elements of energy source supply system 1400 for repair and maintenance of energy source supply system 1400. In some embodiments, one or more of the elements of energy source supply system 1400 can be positioned to support a directional flow of heat generated by energy source supply system 1400 rather than unidirectional heat radiation, and to minimize the formation of hot spots in energy source supply system 1400. In further embodiments, one or more elements of energy source supply system 1400 can be positioned to permit modularity of one or more elements of energy source supply system 1400.

Although energy source supply system 1400 is generally described for embodiments where the first energy source comprises a hydrogen fuel energy source, in some embodiments, first energy source can comprise another fuel energy source, such as, for example, a natural gas fuel energy source.

Figure 16:
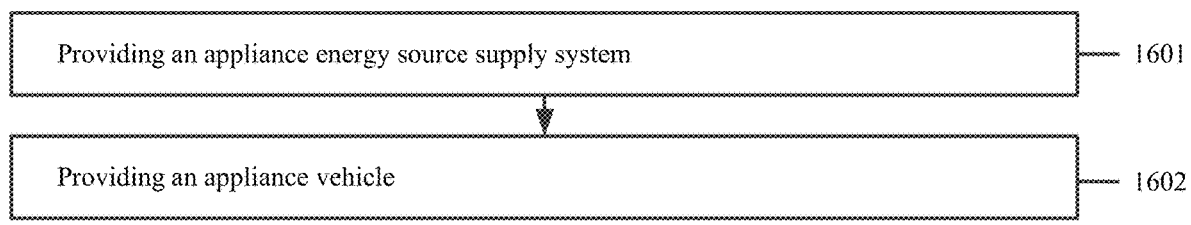
FIG. 16 illustrates a flow chart for an embodiment of a method of providing (e.g., manufacturing) an energy source supply device.

Turning ahead in the drawings, FIG. 16 illustrates a flow chart for an embodiment of method 1600 of providing (e.g., manufacturing) an energy source supply device. Method 1600 is merely exemplary and is not limited to the embodiments presented herein. Method 1600 can be employed in many different embodiments or examples not specifically depicted or described herein. In some embodiments, the activities of method 1600 can be performed in the order presented. In other embodiments, the activities of the method 1600 can be performed in any other suitable order. In still other embodiments, one or more of the activities in method 1600 can be combined or skipped. In many embodiments, the energy source supply device can be similar or identical to one of energy source supply device(s) 101 of FIG. 1 (e.g., one of energy source supply hub(s) 105 (FIG. 1) and/or one of energy source supply appliance(s) 102 (FIG. 1)).

Figure 17:
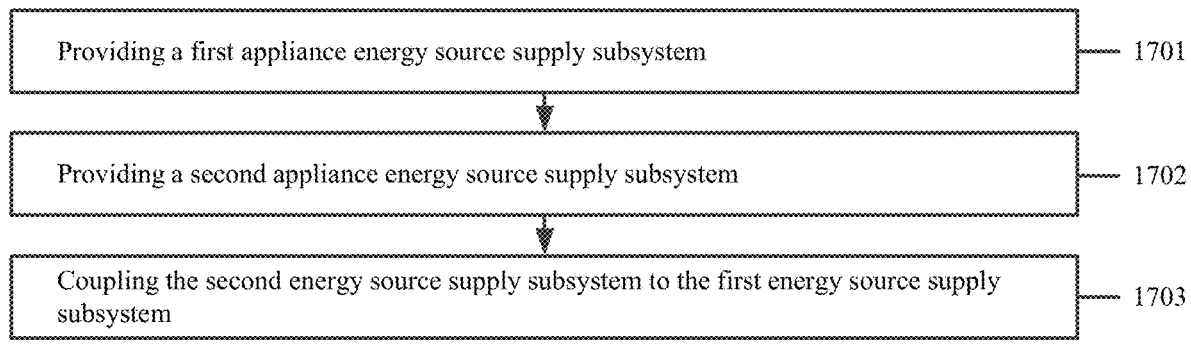
FIG. 17 illustrates an exemplary activity of providing an appliance energy source supply system, according to the embodiment of FIG. 16.

In many embodiments, method 1600 can comprise activity 1601 of providing an appliance energy source supply system. In many embodiments, the appliance energy source supply system can be similar or identical to appliance energy source supply system 114 (FIG. 1), energy source supply system 300 (FIG. 3), and/or energy source supply system 1400 (FIG. 14). FIG. 17 illustrates an exemplary activity 1601, according to the embodiment of FIG. 16.

Figure 18:
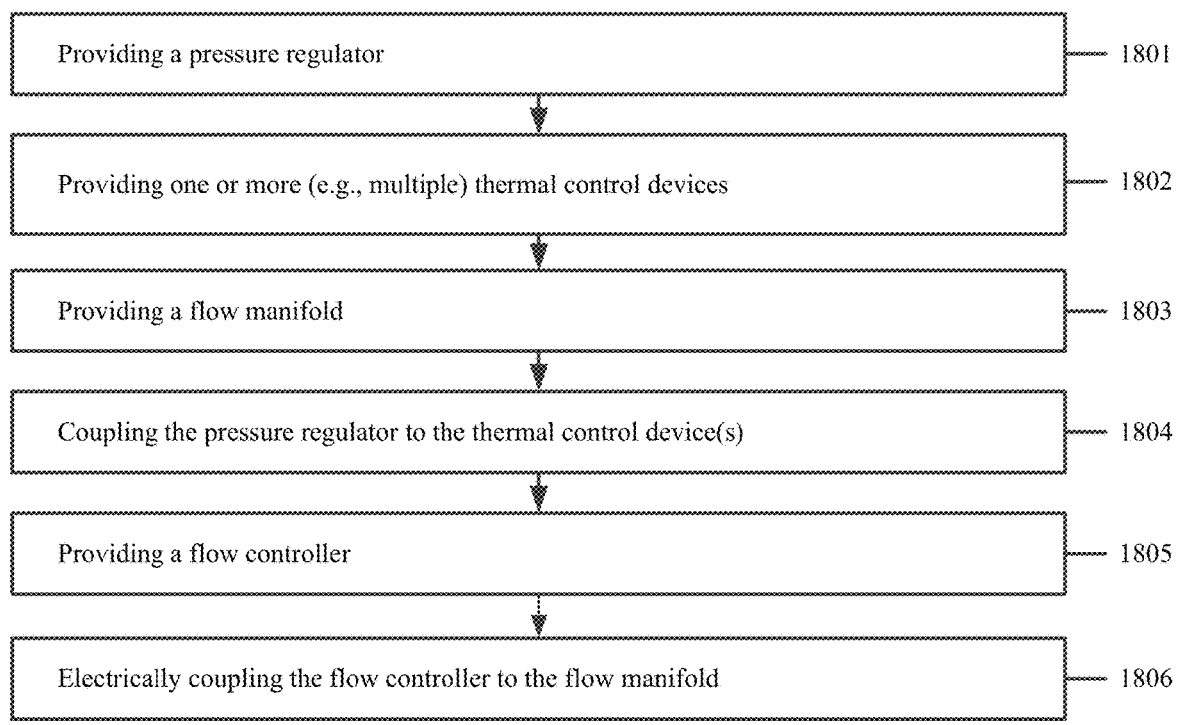
FIG. 18 illustrates an exemplary activity of providing a first appliance energy source supply subsystem, according to the embodiment of FIG. 16.

For example, in many embodiments, activity 1601 can comprise activity 1701 of providing a first appliance energy source supply subsystem. In some embodiments, the first appliance energy source supply subsystem can be similar or identical to first appliance energy source supply subsystem 115 (FIG. 1), first energy source supply subsystem 301 (FIG. 3), and/or first energy source supply subsystem 1401 (FIG. 14). FIG. 18 illustrates an exemplary activity 1701, according to the embodiment of FIG. 16.

In many embodiments, activity 1701 can comprise activity 1801 of providing a pressure regulator. In some embodiments, the pressure regulator can be similar or identical to pressure regulator 1501 (FIG. 15).

In many embodiments, activity 1701 can comprise activity 1802 of providing one or more (e.g., multiple) thermal control devices. In some embodiments, the thermal control device(s) can be similar or identical to thermal control device(s) 1502 (FIG. 15).

In many embodiments, activity 1701 can comprise activity 1803 of providing a flow manifold. In some embodiments, the flow manifold can be similar or identical to flow manifold 1505 (FIG. 15). In other embodiments, activity 1803 can be omitted.

Figure 19:
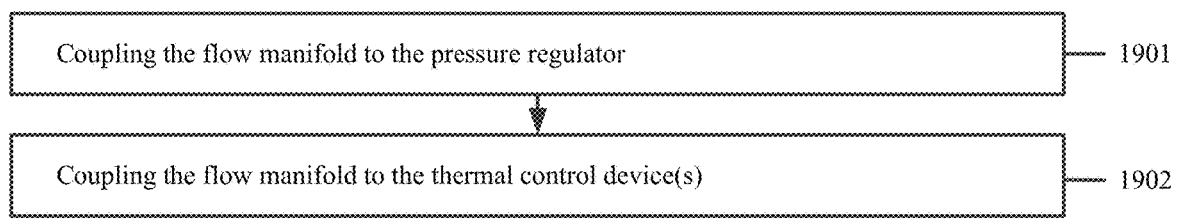
FIG. 19 illustrates an exemplary activity of coupling a pressure regulator to one or more thermal control devices, according to the embodiment of FIG. 16.

In many embodiments, activity 1701 can comprise activity 1804 of coupling the pressure regulator to the thermal control device(s). For example, in some embodiments, performing activity 1804 can be similar or identical to coupling pressure regulator 1501 (FIG. 15) to thermal control device(s) 1502 (FIG. 15) as described above with respect to energy source supply system 1400 (FIG. 14). FIG. 19 illustrates an exemplary activity 1804, according to the embodiment of FIG. 16.

In many embodiments, activity 1804 can comprise activity 1901 of coupling the flow manifold to the pressure regulator. For example, in some embodiments, performing activity 1901 can be similar or identical to coupling flow manifold 1505 (FIG. 15) to pressure regulator 1501 (FIG. 15) as described above with respect to energy source supply system 1400 (FIG. 14). In some embodiments, activity 1901 can be omitted, such as, for example, when activity 1803 is omitted.

In many embodiments, activity 1804 can comprise activity 1902 of coupling the flow manifold to the thermal control device(s). For example, in some embodiments, performing activity 1902 can be similar or identical to coupling flow manifold 1505 (FIG. 15) to thermal control device(s) 1502 (FIG. 15) as described above with respect to energy source supply system 1400 (FIG. 14). In some embodiments, activity 1902 can be omitted, such as, for example, when activity 1803 is omitted.

Referring back to FIG. 18, in many embodiments, activity 1701 can comprise activity 1805 of providing a flow controller. In some embodiments, the flow controller can be similar or identical to flow controller 1506 (FIG. 15). In other embodiments, activity 1805 can be omitted, such as, for example, when activity 1803 is omitted.

In many embodiments, activity 1701 can comprise activity 1806 of electrically coupling the flow controller to the flow manifold. For example, in some embodiments, performing activity 1806 can be similar or identical to electrically coupling flow controller 1506 (FIG. 15) to flow manifold 1505 (FIG. 15) as described above with respect to energy source supply system 1400 (FIG. 14). In some embodiments, activity 1806 can be omitted, such as, for example, when activity 1805 is omitted.

Referring back to FIG. 17, in some embodiment, activity 1601 can comprise activity 1702 of providing a second appliance energy source supply subsystem. In some embodiments, the second appliance energy source supply subsystem can be similar or identical second appliance energy source supply subsystem 116 (FIG. 1), second energy source supply subsystem 302 (FIG. 3), and/or second energy source supply subsystem 1402 (FIG. 14). In some embodiments, activity 1702 can be omitted.

In many embodiments, activity 1601 can comprise activity 1703 of coupling the second appliance energy source supply subsystem to the first appliance energy source supply subsystem. For example, in some embodiments, performing activity 1703 can be similar or identical to coupling second energy source supply subsystem 1401 (FIG. 14) to first energy source supply subsystem 1402 (FIG. 14) as described above with respect to energy source supply system 1400 (FIG. 14). In other embodiments, activity 1703 can be omitted.

Referring back to FIG. 16, in many embodiments, method 1600 can comprise activity 1602 of providing an appliance vehicle. In some embodiments, the appliance vehicle can be similar or identical to appliance vehicle 117 (FIG. 1). In other embodiments, activity 1602 can be omitted.

Figure 20:
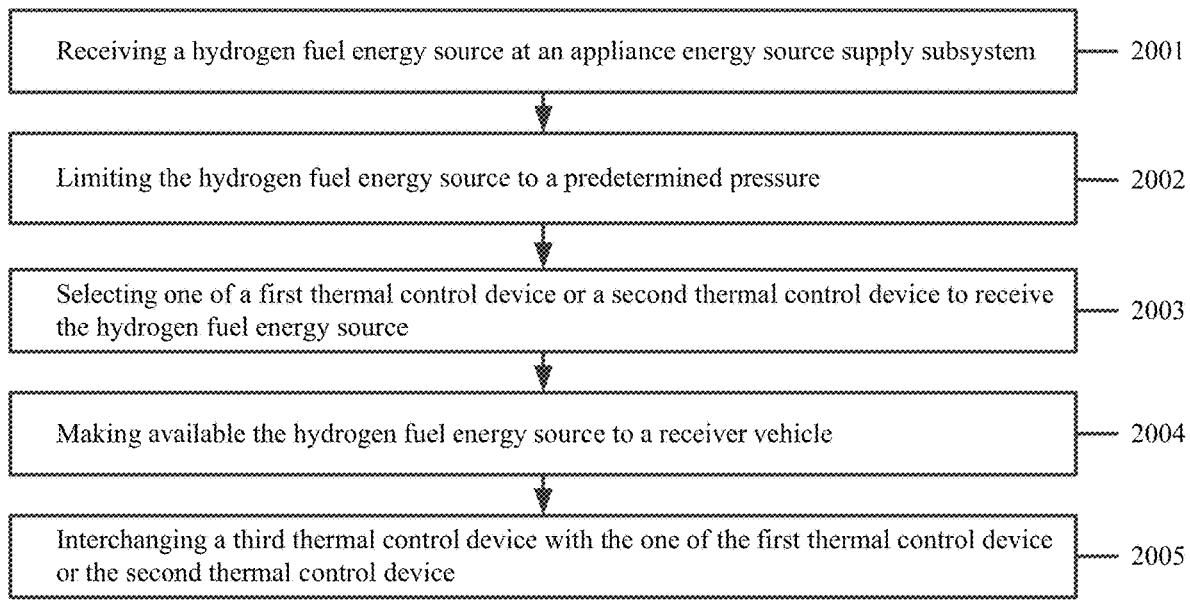
FIG. 20 illustrates a flow chart for an embodiment of a method.

Turning ahead in the drawings, FIG. 20 illustrates a flow chart for an embodiment of method 2000. Method 2000 is merely exemplary and is not limited to the embodiments presented herein. Method 2000 can be employed in many different embodiments or examples not specifically depicted or described herein. In some embodiments, the procedures, the activities of method 2000 can be performed in the order presented. In other embodiments, the procedures, the activities of the method 2000 can be performed in any other suitable order. In still other embodiments, one or more of the activities in method 2000 can be combined or skipped.

In many embodiments, method 2000 can comprise activity 2001 of receiving a hydrogen fuel energy source at an appliance energy source supply subsystem. For example, in some embodiments, performing activity 2001 can be similar or identical to receiving a hydrogen fuel energy source at appliance energy source supply subsystem 1401 (FIG. 14) as described above with respect to energy source supply system 1400 (FIG. 14). Further, the appliance energy source supply subsystem can be similar or identical to appliance energy source supply subsystem 1401 (FIG. 14). In further embodiments, performing activity 2001 can comprise receiving the hydrogen fuel energy source at the appliance energy source supply subsystem when the appliance energy supply subsystem is located at a first location.

In many embodiments, method 2000 can comprise activity 2002 of limiting the hydrogen fuel energy source to a predetermined pressure. For example, in some embodiments, performing activity 2002 can be similar or identical to limiting the hydrogen fuel energy source to a predetermined pressure as described above with respect to energy source supply system 1400 (FIG. 14). In further embodiments, activity 2002 can be performed after activity 2001.

Figure 21:
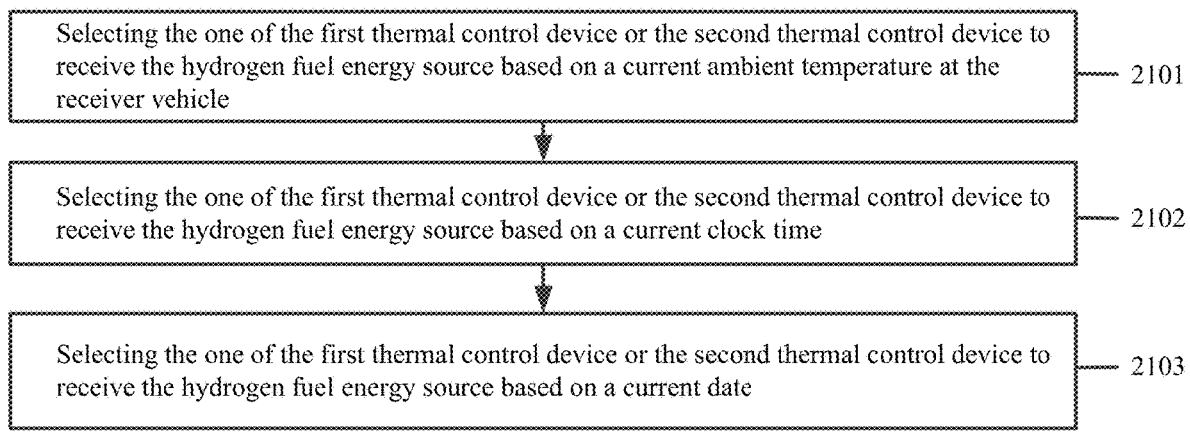
FIG. 21 illustrates a flow chart for an exemplary activity of selecting one of a first thermal control device or a second thermal control device to receive the hydrogen fuel energy source, according to the embodiment of FIG. 20.

In many embodiments, method 2000 can comprise activity 2003 of selecting one of a first thermal control device or a second thermal control device to receive the hydrogen fuel energy source. For example, in some embodiments, performing activity 2003 can be similar or identical to selecting one of first thermal control device 1503 (FIG. 15) or second thermal control device 1504 (FIG. 15) to receive the hydrogen fuel energy source as described above with respect to energy source supply system 1400 (FIG. 14). Further, the first thermal control device can be similar or identical to first thermal control device 1503 (FIG. 15); and/or the second thermal control device can be similar or identical to second thermal control device 1504 (FIG. 15). FIG. 21 illustrates an exemplary activity 2003, according to the embodiment of FIG. 20.

In many embodiments, activity 2003 can comprise activity 2101 of selecting the one of the first thermal control device or the second thermal control device to receive the hydrogen fuel energy source based on a current ambient temperature at the receiver vehicle. In some embodiments, performing activity 2101 can be similar or identical to selecting the one of the first thermal control device or the second thermal control device to receive the hydrogen fuel energy source based on a current ambient temperature at the receiver vehicle as described above with respect to energy source supply system 1400 (FIG. 14). In other embodiments, activity 2101 can be omitted.

In many embodiments, activity 2003 can comprise activity 2102 of selecting the one of the first thermal control device or the second thermal control device to receive the hydrogen fuel energy source based on a current clock time. In some embodiments, performing activity 2102 can be similar or identical to selecting the one of the first thermal control device or the second thermal control device to receive the hydrogen fuel energy source based on a current clock time as described above with respect to energy source supply system 1400 (FIG. 14). In other embodiments, activity 2102 can be omitted.

In many embodiments, activity 2003 can comprise activity 2103 of selecting the one of the first thermal control device or the second thermal control device to receive the hydrogen fuel energy source based on a current date. In some embodiments, performing activity 2103 can be similar or identical to selecting the one of the first thermal control device or the second thermal control device to receive the hydrogen fuel energy source based on a current date as described above with respect to energy source supply system 1400 (FIG. 14). In other embodiments, activity 2103 can be omitted.

Referring back to FIG. 20, in many embodiments, method 2000 can comprise activity 2004 of making available the hydrogen fuel energy source to a receiver vehicle. For example, in some embodiments, performing activity 2004 can be similar or identical to making available the hydrogen fuel energy source to a receiver vehicle as described above with respect to energy source supply system 1400 (FIG. 14). Further, the receiver vehicle can be similar or identical to one of receiver vehicle(s) 109 (FIG. 1) and/or receiver vehicle 1404 (FIG. 3). In further embodiments, activity 2004 can be performed after activity 2001, activity 2002, and/or activity 2003. In many embodiments, performing activity 2004 can comprise receiving the hydrogen fuel energy source at the one of the first thermal control device or the second thermal control device. In these or other embodiments, performing activity 2004 can comprise making available the hydrogen fuel energy source to the receiver vehicle when the appliance energy supply subsystem is located at a second location different than the first location at which the appliance energy supply subsystem receives the hydrogen fuel energy source.

In many embodiments, method 2000 can comprise activity 2005 of interchanging a third thermal control device with the one of the first thermal control device or the second thermal control device. For example, in some embodiments, performing activity 2005 of interchanging a third thermal control device with the one of the first thermal control device or the second thermal control device as described above with respect to energy source supply system 1400 (FIG. 14). Further, the third thermal control device can be similar or identical to one of thermal control device(s) 1502 (FIG. 15). In some embodiments, activity 2005 can be performed before activity 2003.

Some embodiments of method 2000 can be implemented with a natural gas fuel energy source instead of a hydrogen fuel energy source.

Turning ahead in the drawings, FIG. 22 illustrates an exemplary embodiment of a computer system 2200, all of which or a portion of which can be suitable for implementing part or all of one or more embodiments of the techniques, methods, and systems described herein. For example, in some embodiments, all or a portion of computer system 2200 can be suitable for implementing part or all of one or more embodiments of the techniques, methods, and/or systems described herein. Furthermore, one or more elements of computer system 2200 (e.g., a refreshing monitor 2206, a keyboard 2204, and/or a mouse 2210, etc.) also can be appropriate for implementing part or all of one or more embodiments of the techniques, methods, and/or systems described herein.

In many embodiments, computer system 2200 can comprise chassis 2202 containing one or more circuit boards (not shown), a Universal Serial Bus (USB) port 2212, a hard drive 2214, and an optical disc drive 2216. Meanwhile, for example, optical disc drive 2216 can comprise a Compact Disc Read-Only Memory (CD-ROM), a Digital Video Disc (DVD) drive, or a Blu-ray drive. Still, in other embodiments, a different or separate one of a chassis 2202 (and its internal components) can be suitable for implementing part or all of one or more embodiments of the techniques, methods, and/or systems described herein.

Figure 23:
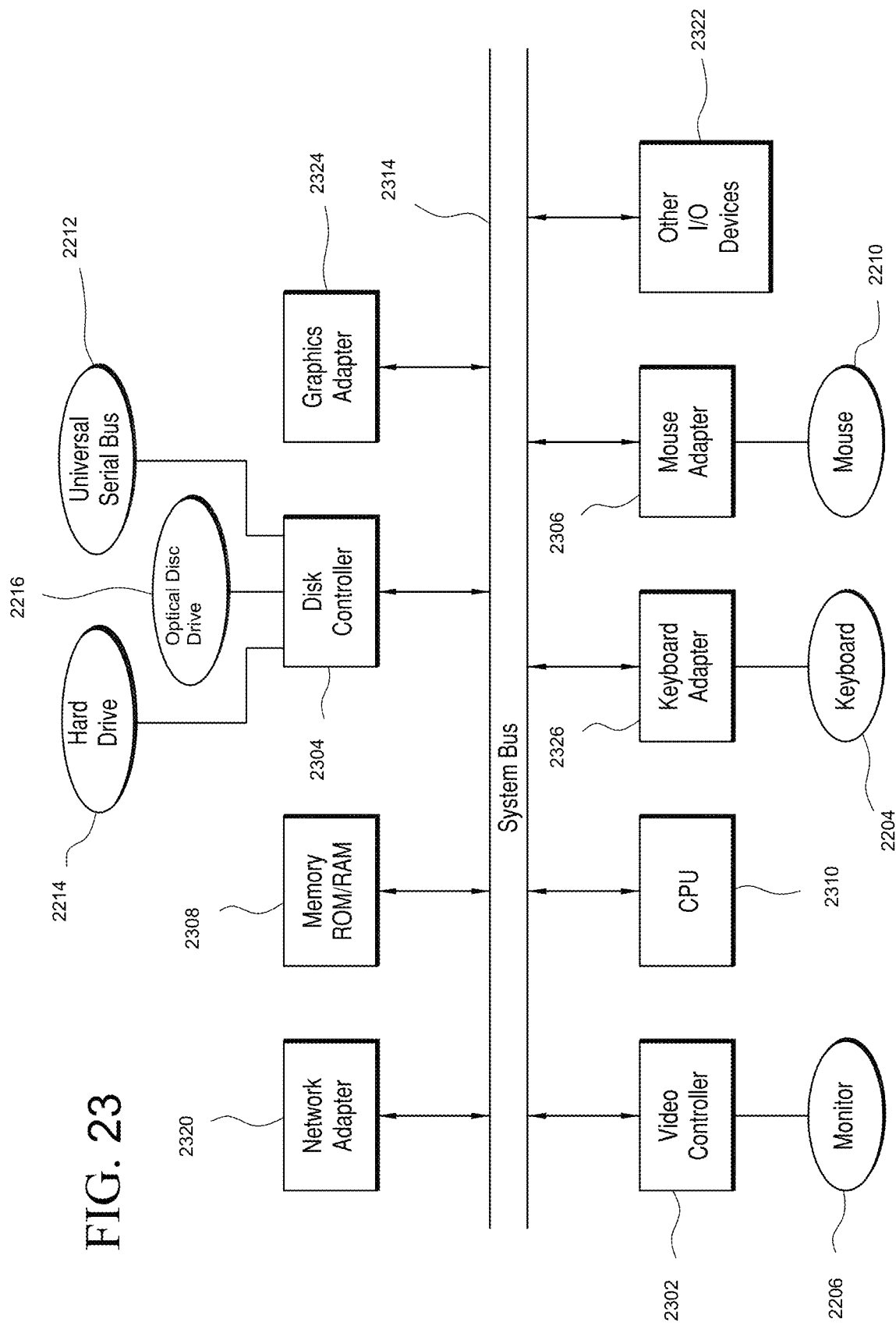
FIG. 23 illustrates a representative block diagram of exemplary elements included on the circuit boards inside a chassis of the computer system of FIG. 22.

Turning ahead in the drawings, FIG. 23 illustrates a representative block diagram of exemplary elements included on the circuit boards inside chassis 2202 (FIG. 23). For example, a central processing unit (CPU) 2310 is coupled to a system bus 2314. In various embodiments, the architecture of CPU 2310 can be compliant with any of a variety of commercially distributed architecture families.

In many embodiments, system bus 2314 also is coupled to a memory storage unit 2308, where memory storage unit 2308 can comprise (i) non-volatile memory, such as, for example, read only memory (ROM) and/or (ii) volatile memory, such as, for example, random access memory (RAM). The non-volatile memory can be removable and/or non-removable non-volatile memory. Meanwhile, RAM can include dynamic RAM (DRAM), static RAM (SRAM), etc. Further, ROM can include mask-programmed ROM, programmable ROM (PROM), one-time programmable ROM (OTP), erasable programmable read-only memory (EPROM), electrically erasable programmable ROM (EEPROM) (e.g., electrically alterable ROM (EAROM) and/or flash memory), etc. In these or other embodiments, memory storage unit 2308 can comprise (i) non-transitory memory and/or (ii) transitory memory.

The memory storage device(s) of the various embodiments disclosed herein can comprise memory storage unit 2308, an external memory storage drive (not shown), such as, for example, a USB-equipped electronic memory storage drive coupled to universal serial bus (USB) port 2212 (FIGS. 22 & 23), hard drive 2214 (FIGS. 22 & 23), optical disc drive 2216 (FIGS. 22 & 23), a floppy disk drive (not shown), etc. As used herein, non-volatile and/or non-transitory memory storage device(s) refer to the portions of the memory storage device(s) that are non-volatile and/or non-transitory memory.

In various examples, portions of the memory storage device(s) of the various embodiments disclosed herein (e.g., portions of the non-volatile memory storage device(s)) can be encoded with a boot code sequence suitable for restoring computer system 2200 (FIG. 22) to a functional state after a system reset. In addition, portions of the memory storage device(s) of the various embodiments disclosed herein (e.g., portions of the non-volatile memory storage device(s)) can comprise microcode such as a Basic Input-Output System (BIOS) or Unified Extensible Firmware Interface (UEFI) operable with computer system 2200 (FIG. 22). In the same or different examples, portions of the memory storage device(s) of the various embodiments disclosed herein (e.g., portions of the non-volatile memory storage device(s)) can comprise an operating system, which can be a software program that manages the hardware and software resources of a computer and/or a computer network. Meanwhile, the operating system can perform basic tasks such as, for example, controlling and allocating memory, prioritizing the processing of instructions, controlling input and output devices, facilitating networking, and managing files. Exemplary operating systems can comprise (i) Microsoft® Windows® operating system (OS) by Microsoft Corp. of Redmond, Washington, United States of America, (ii) Mac® OS by Apple Inc. of Cupertino, California, United States of America, (iii) UNIX® OS, and (iv) Linux® OS. Further, as used herein, the term "computer network" can refer to a collection of computers and devices interconnected by communications channels that facilitate communications among users and allow users to share resources (e.g., an internet connection, an Ethernet connection, etc.). The computers and devices can be interconnected according to any conventional network topology (e.g., bus, star, tree, linear, ring, mesh, etc.).

As used herein, the term "processor" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. In some examples, the one or more processors of the various embodiments disclosed herein can comprise CPU 2310.

In the depicted embodiment of FIG. 23, various I/O devices such as a disk controller 2304, a graphics adapter 2324, a video controller 2302, a keyboard adapter 2326, a mouse adapter 2306, a network adapter 2320, and other I/O devices 2322 can be coupled to system bus 2314. Keyboard adapter 2326 and mouse adapter 2306 are coupled to keyboard 2204 (FIGS. 22 & 23) and mouse 2210 (FIGS. 22 & 23), respectively, of computer system 2200 (FIG. 22). While graphics adapter 2324 and video controller 2302 are indicated as distinct units in FIG. 23, video controller 2302 can be integrated into graphics adapter 2324, or vice versa in other embodiments. Video controller 2302 is suitable for refreshing monitor 2206 (FIGS. 22 & 23) to display images on a screen 2208 (FIG. 22) of computer system 2200 (FIG. 22). Disk controller 2304 can control hard drive 2214 (FIGS. 22 & 23), USB port 2212 (FIGS. 22 & 23), and CD-ROM drive 2216 (FIGS. 22 & 23). In other embodiments, distinct units can be used to control each of these devices separately.

Network adapter 2320 can be suitable to connect computer system 2200 (FIG. 22) to a computer network by wired communication (e.g., a wired network adapter) and/or wireless communication (e.g., a wireless network adapter). In some embodiments, network adapter 2320 can be plugged or coupled to an expansion port (not shown) in computer system 2200 (FIG. 22). In other embodiments, network adapter 2320 can be built into computer system 2200 (FIG. 22). For example, network adapter 2320 can be built into computer system 2200 (FIG. 22) by being integrated into the motherboard chipset (not shown), or implemented via one or more dedicated communication chips (not shown), connected through a PCI (peripheral component interconnector) or a PCI express bus of computer system 2200 (FIG. 22) or USB port 2212 (FIG. 22).

Returning now to FIG. 22, although many other components of computer system 2200 are not shown, such components and their interconnection are well known to those of ordinary skill in the art. Accordingly, further details concerning the construction and composition of computer system 2200 and the circuit boards inside chassis 2202 are not discussed herein.

Meanwhile, when computer system 2200 is running, program instructions (e.g., computer instructions) stored on one or more of the memory storage device(s) of the various embodiments disclosed herein can be executed by CPU 2310 (FIG. 23). At least a portion of the program instructions, stored on these devices, can be suitable for carrying out at least part of the techniques, methods, and activities of the methods described herein. In various embodiments, computer system 2200 can be reprogrammed with one or more systems, applications, and/or databases to convert computer system 2200 from a general purpose computer to a special purpose computer.

Further, although computer system 2200 is illustrated as a desktop computer in FIG. 22, in many examples, system 2200 can have a different form factor while still having functional elements similar to those described for computer system 2200. In some embodiments, computer system 2200 may comprise a single computer, a single server, or a cluster or collection of computers or servers, or a cloud of computers or servers. Typically, a cluster or collection of servers can be used when the demand on computer system 2200 exceeds the reasonable capability of a single server or computer. In certain embodiments, computer system 2200 may comprise a laptop computer system. In certain additional embodiments, computer system 2200 may comprise an embedded system.

Although the invention has been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1-23 may be modified, and that the foregoing discussion of certain of these embodiments does not necessarily represent a complete description of all possible embodiments. For example, one or more of the activities of method 400 (FIG. 4), method 900 (FIG. 9), method 1200 (FIG. 12), method 1300 (FIG. 13), method 1600 (FIG. 16), method 2000 (FIG. 20) or one or more of the other methods described herein may include different activities and be performed by many different elements, in many different orders.

Generally, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An appliance energy source supply system for an energy source supply appliance, the appliance energy source supply system comprising:
 a first thermal control device and a second thermal control device;
 wherein:
  the appliance energy source supply system is configured so that a hydrogen fuel energy source is selectively received by one of the first thermal control device or the second thermal control device before the hydrogen fuel energy source is made available to a receiver vehicle;

the first thermal control device is configured to receive the hydrogen fuel energy source and to cause a first temperature reduction of the hydrogen fuel energy source while the hydrogen fuel energy source passes through the first thermal control device;

the second thermal control device is configured to receive the hydrogen fuel energy source and to cause a second temperature reduction of the hydrogen fuel energy source while the hydrogen fuel energy source passes through the second thermal control device; and the first temperature reduction is different than the second temperature reduction.

2. The appliance energy source supply system of claim 1 wherein:
the first thermal control device and the second thermal control device are devoid of moving parts.

3. The appliance energy source supply system of claim 1 wherein:
the first thermal control device comprises a first restrictive flow orifice, and the first restrictive flow orifice comprises a first orifice diameter;
the second thermal control device comprises a second restrictive flow orifice, and the second restrictive flow orifice comprises a second orifice diameter; and
the first orifice diameter is different than the second orifice diameter.

4. The appliance energy source supply system of claim 3 wherein:
the first orifice diameter is one of approximately 0.0178 centimeter, approximately 0.0381 centimeter, approximately 0.0457 centimeter, approximately 0.0508 centimeter, approximately 0.0635 centimeter, approximately 0.0762 centimeter, or approximately 0.102 centimeter; and
the second orifice diameter is a different one of the approximately 0.0178 centimeter, the approximately 0.0381 centimeter, the approximately 0.0457 centimeter, the approximately 0.0508 centimeter, the approximately 0.0635 centimeter, the approximately 0.0762 centimeter, or the approximately 0.102 centimeter.

5. The appliance energy source supply system of claim 1 wherein:
the appliance energy source supply system is configured such that each of the first thermal control device and the second thermal control device is able to be interchanged with a third thermal control device at different times;
the third thermal control device is configured to receive the hydrogen fuel energy source and to cause a third temperature reduction of the hydrogen fuel energy source while the hydrogen fuel energy source passes through the third thermal control device; and
the third temperature reduction is different than the first temperature reduction and the second temperature reduction.

6. The appliance energy source supply system of claim 1 further comprising:
a pressure regulator;
wherein:
the appliance energy source supply system is configured so that the hydrogen fuel energy source is received by the pressure regulator before the hydrogen fuel energy source is made available to the receiver vehicle;
the pressure regulator is configured to receive the hydrogen fuel energy source and to limit the hydrogen fuel energy source to a predetermined pressure range when the pressure regulator receives the hydrogen fuel energy source; and
the hydrogen fuel energy source is selectively received by the one of the first thermal control device or the second thermal control device after the hydrogen fuel energy source is received by the pressure regulator.

7. The appliance energy source supply system of claim 6 wherein:
the predetermined pressure range is greater than or equal to approximately 12.4 Megapascals (gauge).

8. The appliance energy source supply system of claim 1 wherein:
the appliance energy source supply system is configured to make available the hydrogen fuel energy source to the receiver vehicle without receiving temperature data from the receiver vehicle.

9. The appliance energy source supply system of claim 1 wherein:
the appliance energy source supply system is configured to be transported by an appliance vehicle of the energy source supply appliance.

10. The appliance energy source supply system of claim 9 wherein:
the first thermal control device and the second thermal control device are devoid of moving parts.

11. The appliance energy source supply system of claim 9 wherein:
the first thermal control device comprises a first restrictive flow orifice, and the first restrictive flow orifice comprises a first orifice diameter;
the second thermal control device comprises a second restrictive flow orifice, and the second restrictive flow orifice comprises a second orifice diameter; and
the first orifice diameter is different than the second orifice diameter.

12. A method comprising:
providing an appliance energy source supply system, wherein providing the appliance energy source supply system comprises:
providing a first thermal control device; and
providing a second thermal control device;
wherein:
the appliance energy source supply system is configured so that a hydrogen fuel energy source is selectively received by one of the first thermal control device or the second thermal control device before the hydrogen fuel energy source is made available to a receiver vehicle;
the first thermal control device is configured to receive the hydrogen fuel energy source and to cause a first temperature reduction of the hydrogen fuel energy source while the hydrogen fuel energy source passes through the first thermal control device;
the second thermal control device is configured to receive the hydrogen fuel energy source and to cause a second temperature reduction of the hydrogen fuel energy source while the hydrogen fuel energy source passes through the second thermal control device; and
the first temperature reduction is different than the second temperature reduction.

13. The method of claim 12 wherein:
the first thermal control device and the second thermal control device are devoid of moving parts.

14. The method of claim 12 wherein:
providing the first thermal control device comprises providing a first restrictive flow orifice;
providing the second thermal control device comprises providing a second restrictive flow orifice;
the first restrictive flow orifice comprises a first orifice diameter;
the second restrictive flow orifice comprises a second orifice diameter; and
the first orifice diameter is different than the second orifice diameter.

15. The method of claim 12 further comprising:
providing an appliance vehicle;
wherein:
the appliance energy source supply system is configured to be transported by the appliance vehicle.

16. The method of claim 15 wherein:
providing the first thermal control device comprises providing a first restrictive flow orifice;
providing the second thermal control device comprises providing a second restrictive flow orifice;
the first restrictive flow orifice comprises a first orifice diameter;
the second restrictive flow orifice comprises a second orifice diameter; and
the first orifice diameter is different than the second orifice diameter.

17. The method of claim 12 wherein:
providing the appliance energy source supply system further comprises providing a pressure regulator;
the appliance energy source supply system is configured so that the hydrogen fuel energy source is received by the pressure regulator before the hydrogen fuel energy source is made available to the receiver vehicle; and
the pressure regulator is configured to:
receive the hydrogen fuel energy source before the hydrogen fuel energy source is selectively received by the one of the first thermal control device or the second thermal control device; and
limit the hydrogen fuel energy source to a predetermined pressure range when the pressure regulator receives the hydrogen fuel energy source.

18. A method comprising:
receiving a hydrogen fuel energy source at an appliance energy source supply system, wherein the appliance energy source supply system comprises a first thermal control device and a second thermal control device;
selecting one of the first thermal control device or the second thermal control device to receive the hydrogen fuel energy source, wherein:
the first thermal control device is configured to receive the hydrogen fuel energy source and to cause a first temperature reduction of the hydrogen fuel energy source while the hydrogen fuel energy source passes through the first thermal control device;
the second thermal control device is configured to receive the hydrogen fuel energy source and to cause a second temperature reduction of the hydrogen fuel energy source while the hydrogen fuel energy source passes through the second thermal control device; and
the first temperature reduction is different than the second temperature reduction; and
after selecting the one of the first thermal control device or the second thermal control device, making available the hydrogen fuel energy source to a receiver vehicle, wherein:
making available the hydrogen fuel energy source to the receiver vehicle comprises receiving the hydrogen fuel energy source at the one of the first thermal control device or the second thermal control device, as selected, before receiving the hydrogen fuel energy source at the receiver vehicle.

19. The method of claim 18 wherein:
the first thermal control device and the second thermal control device are devoid of moving parts.

20. The method of claim 18 wherein:
the first thermal control device comprises a first restrictive flow orifice, and the first restrictive flow orifice comprises a first orifice diameter;
the second thermal control device comprises a second restrictive flow orifice, and the second restrictive flow orifice comprises a second orifice diameter; and
the first orifice diameter is different than the second orifice diameter.

21. The method of claim 18 further comprising:
before selecting the one of the first thermal control device or the second thermal control device to receive the hydrogen fuel energy source, interchanging a third thermal control device with the one of the first thermal control device or the second thermal control device such that selecting the one of the first thermal control device or the second thermal control device to receive the hydrogen fuel energy source comprises selecting the third thermal control device to receive the hydrogen fuel energy source,
wherein:
the third thermal control device is configured to receive the hydrogen fuel energy source and to cause a third temperature reduction of the hydrogen fuel energy source while the hydrogen fuel energy source passes through the third thermal control device; and
the third temperature reduction is different than the first temperature reduction and the second temperature reduction.

22. The method of claim 18 wherein:
receiving the hydrogen fuel energy source at the appliance energy source supply system comprises receiving the hydrogen fuel energy source at the appliance energy source supply system when the appliance energy source supply system is located at a first location; and
making available the hydrogen fuel energy source to the receiver vehicle comprises making available the hydrogen fuel energy source to the receiver vehicle when the appliance energy source supply system is located at a second location, wherein the first location is different than the second location.

23. The method of claim 18 wherein:
selecting the one of the first thermal control device or the second thermal control device to receive the hydrogen fuel energy source comprises selecting the one of the first thermal control device or the second thermal control device to receive the hydrogen fuel energy source based on a current ambient temperature at the receiver vehicle.

24. The method of claim 18 wherein:
selecting the one of the first thermal control device or the second thermal control device to receive the hydrogen fuel energy source comprises selecting the one of the first thermal control device or the second thermal control device to receive the hydrogen fuel energy source based on a current time of day.

25. The method of claim 18 wherein:

selecting the one of the first thermal control device or the second thermal control device to receive the hydrogen fuel energy source comprises selecting the one of the first thermal control device or the second thermal control device to receive the hydrogen fuel energy source based on a current date.

26. The method of claim 18 wherein:

after receiving the hydrogen fuel energy source at the appliance energy source supply system and before making available the hydrogen fuel energy source to the receiver vehicle, limiting the hydrogen fuel energy source to a predetermined pressure range.

* * * * *